United States Patent
Karabelas et al.

(10) Patent No.: US 6,492,406 B1
(45) Date of Patent: Dec. 10, 2002

(54) PHARMACEUTICALLY ACTIVE COMPOUNDS

(75) Inventors: Kostas Karabelas, Lund (SE); Matti Lepistö, Lund (SE); Peter Sjö, Lund (SE)

(73) Assignee: Astrazeneca AB, Sodertalje (SE)

( * ) Notice: Subject to any disclaimer, the term of this patent is extended or adjusted under 35 U.S.C. 154(b) by 0 days.

(21) Appl. No.: 09/646,972

(22) PCT Filed: Mar. 19, 2000

(86) PCT No.: PCT/SE00/01009
§ 371 (c)(1),
(2), (4) Date: Sep. 25, 2000

(87) PCT Pub. No.: WO00/71537
PCT Pub. Date: Nov. 30, 2000

(30) Foreign Application Priority Data

May 21, 1999 (SE) .............................................. 9901854
Feb. 28, 2000 (SE) .............................................. 0000645

(51) Int. Cl.$^7$ .................. C07D 403/14; A61K 31/4196
(52) U.S. Cl. .................. 514/384; 548/263.2; 548/264.6
(58) Field of Search .......................... 548/263.2, 264.6; 514/384

(56) References Cited

U.S. PATENT DOCUMENTS

| | | | |
|---|---|---|---|
| 3,642,803 A | 2/1972 | Welstead, Jr. | |
| 3,821,389 A | 6/1974 | Grivas | |
| RE28,973 E | 9/1976 | Welstead, Jr. | |
| 4,031,221 A | 6/1977 | Helsley et al. | |
| 4,062,869 A | 12/1977 | Weston | |
| 4,466,976 A | 8/1984 | Klose et al. | |
| 4,532,250 A | 7/1985 | Stout et al. | |
| 4,585,771 A | 4/1986 | Klose et al. | |
| 4,598,079 A | 7/1986 | Beyerle et al. | |
| 4,912,125 A | 3/1990 | Huebner et al. | |
| 5,057,614 A | 10/1991 | Davis et al. | |
| 5,077,293 A | 12/1991 | Smith et al. | |
| 5,192,770 A | 3/1993 | Clark et al. | |
| 5,380,746 A | 1/1995 | Barth et al. | |
| 5,399,712 A | 3/1995 | Hill | |
| 5,401,738 A | 3/1995 | Mederski et al. | |
| 5,466,699 A | 11/1995 | Robertson et al. | |
| 5,516,915 A | 5/1996 | Barth et al. | |
| 5,519,036 A | * 5/1996 | Himmelsbach | 514/530 |
| 5,545,636 A | 8/1996 | Heath et al. | |
| 5,612,362 A | 3/1997 | MacLeod | |
| 5,668,152 A | 9/1997 | Heath, Jr. et al. | |
| 5,948,907 A | 9/1999 | Faul et al. | |
| 6,015,807 A | 1/2000 | Engel et al. | |
| 6,054,590 A | 4/2000 | Piondexter et al. | |
| 6,103,712 A | 8/2000 | Ways | |
| 6,153,641 A | 11/2000 | Bergstrand et al. | |

FOREIGN PATENT DOCUMENTS

| | | |
|---|---|---|
| DE | 3141063 A1 | 4/1983 |
| EP | 0328026 A1 | 2/1989 |
| EP | 0464604 A2 | 1/1992 |
| EP | 0490263 A1 | 6/1992 |
| EP | 0540956 A1 | 11/1993 |
| EP | 0675125 A1 | 10/1995 |
| FR | 7311450 | 3/1973 |
| GB | 1500176 | 2/1978 |
| GB | 2090826 A | 7/1982 |
| SU | 389096 | 7/1973 |
| WO | WO93/18765 | 9/1993 |
| WO | WO94/19343 | 9/1994 |
| WO | WO95/17182 | 6/1995 |
| WO | WO96/01825 | 1/1996 |
| WO | WO98/13368 | 4/1998 |
| WO | WO98/43632 | 10/1998 |
| WO | WO99/32483 | 7/1999 |

OTHER PUBLICATIONS

Bergstrand et al., "Modulation of Neutrophil Superoxide Generation by Inhibitors of Protein Kinase C, . . . " The Journal of Pharmacology and Experimental Therapeutics, vol. 263, No. 3, pp. 1334–1346.

Chakravarthy et al., "The Direct Measurement of Protein Kinase C (PKC) Activity in Isolated Membranes Using a Selective Peptide Substate", Analytical Biochemistry, 1991, vol. 196, pp. 144–150.

Galvez et al., "A Conveinent Preparation of Haloaminobenzo[b]thiophene Derviatives", Communications (932–933); Nov. 1983.

Galzunov et al., "Investigation of the Riboflavine Operon of Bacillus Subtilis V11. Biochemical Study of Mutants Relating to Early Stages of Biosythesis" Translated from Genetika 10(11):83–92, 1974, see Chemical Abstracts vol. 82 No. 13 (1975) abstract 82817b.

(List continued on next page.)

Primary Examiner—Robert Gersil
(74) Attorney, Agent, or Firm—Fish & Richardson P.C.

(57) ABSTRACT

The present invention relates to novel compounds which are protein kinase C inhibitors, methods for their preparation, intermediates therefor and pharmaceutical compositions comprising them. More particularly, the present invention relates to compounds of formula (I):

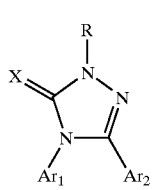

(I)

wherein: one of $Ar_1$ and $Ar_2$ is optionally substituted bicyclic heteroaryl or optionally substituted tricyclic heteroaryl and the other is optionally substituted heteroaryl or optionally substituted aryl;

X is O or S; and

R is H, OH, $NH_2$ or $C_{1-6}$ alkyl (itself optionally substituted by amino or hydroxy); or a salt or solvate thereof, or a solvate of a salt thereof; and the use of such compounds in medical therapies.

17 Claims, No Drawings

OTHER PUBLICATIONS

Gazit et al., "Tyrphostins. 5. Potent Inhibitors of Platelet–Derived Growth Factor Receptor Tyrosine Kinase: Structure–Activity Relationships . . . ", J. Med. Chem., 1996, vol. 39, pp. 2170–2177.

Granet et al., "A Microtiter Plate Assay for Protein Kinase C", Analytical Biochemistry, 1987, 163:458–463.

Hiremath et al., "Synthesis of Substituted 1', 3', 4'-Oxadiazolyl–, Thiadiazolyl–& Triazolyl– indoles", Indian Journal of Chemistry, vol. 20B, pp. 388–390, (1981).

Hiremath et al., "Synthesis of 2–Phenyl(indol–3–yl)isothiocyanates, 1–Substituted–3–(Substituted–2'–phenylindol–3'–yl) Thiosemicarbazides and Their Reactions", Indian Journal of Heterocyclic Chemistry, vol. 2, pp. 119–124, (1992).

Hiremath et al., "Synthesis of biheterocycles containing indole nucleus", Proc. Nat. Acad. Sci. India, 62(A),II, pp. 161–166, (1992).

Hiremath et al., "Synthesis of oxidiazolyl–, thiadiazolyl– and triazolylindoles and indolylthiazolidinones", Indian Journal of Chemistry, vol.: 28B, pp. 626–630, (1989).

Hiremath et al., "Syntheisis of substituted 2,5–bis(1,3,4–oxadiazolyl/thiadiazolyl/1,2,4–triazolyl)indoles and study of thier biological activities", Indian Journal of Chemistry, Bol. 29B, pp. 1118–1124, (1990).

Sonar et al., Indian Drugs (29) 13, pp. 616–619, (1992), "Pharmacolocical Screening of Triazolyindoles and Indolylthiazolidinones".

J. Bergman et al., "Synthesis And Reactions Of Some 3–(2–Haloacyl) indoles", Tetrahedron. vol. 29, pp. 971–976; Pergamon Press 1973.

Kelarev et al., "Synthesis and Properties of Azoles and Their Derivatives", Chemistry of heterocyclic compounds, 1984:9, pp. 1043–1048.

Oikawa et al., "Synthesis of Pimprinine And Related Oxazolylindole Alakaloids From N–ACYL Derivatives Of Tryptamine And Methyl Ester By DDQ Oxidation", Heterocycles, vol. 12, No. 11, 1979.

Olsson et al., Activation of Human Neutrophil Protein Kinase C in vitro by 1,2–isopropylidene–3–decanoyl–sn–glcerol (Ip (COC$_9$), Cellular Signaling, 1989, 1(4): 405–410.

Patent Abstracts of Japan: vol. 14 No. 459 (C–767) (4402): Oct. 4, 1990.

Pereira et al., "Syntheses and Antimicrobial Activities of Five membered Ring Heterocycles Coupled to Indole Moietics", The Journal of Antibiotics. Apr. 1996; vol. 49 No. 4 pp. 380–385.

Pereira et al., "Synthesis and Biological Evaluation of Monoindolyl and Indolocarbazolyl Oxazolones and Imidazolones", Chem. Pharm. Bull. 45(4) 733–736, Pharmaceutical Study Of Japan: 1997.

Sonar et al., "Synthesis Antimicrobial Activity of Triazolylindoles and Indoylthiazolidinones", Indian Journal of Heterocyclic Chemistry, vol. 5, pp. 269–272, (1996).

von Geldern et al., "Azole Endothelin Antagonists. 1. A Receptor Model Explains an Unusual Structure–Activity Profile", J. Med. Chem. 1996, 39, 957–967.

* cited by examiner

PHARMACEUTICALLY ACTIVE COMPOUNDS

FIELD OF THE INVENTION

The present invention relates to novel compounds which are protein kinase C inhibitors, methods for their preparation, intermediates therefor and pharmaceutical compositions comprising them.

BACKGROUND OF THE INVENTION

Protein kinase C (PKC) is a family of phospholipid-dependent serine/threonine-specific protein kinases which play an important role in cellular growth control, regulation and differentiation.

Since the activation of PKC has been implicated in several human disease processes, including various forms of cancer, different forms of inflammatory and/or immunological disorders as well as some neurological disorders, inhibition of PKC could be of therapeutic value in treating these conditions.

Several classes of compounds have been identified as PKC inhibitors, e.g. isoquinoline sulphonamides, sphingosine and related sphingolipids, indolocarbazoles and bisindolylmaleimides.

EP 0 328 026 describes the use of certain bisindolylmaleimides, a class of compounds related to the indolocarbazoles, in medicaments for the treatment of various conditions.

Although PKC inhibitors are described in the prior art, there is a need for specific anti-inflammatory and immuno suppressive compounds, which are suitable for oral administration, and for inhalation. Furthermore, there is a need for such compounds, which are more soluble and less colored than the presently known PKC inhibitors.

SUMMARY OF THE INVENTION

The present invention provides kinase inhibitors which are particularly PKC inhibitors. methods for their preparation and intermediates used for their preparation.

The kinase inhibitors of the present invention are surprisingly more soluble and less colored than the kinase inhibitors, especially the PKC inhibitors. known in the prior art.

The present invention also provides the use of the compounds of the present invention for the treatment of inflammatory, immunological, bronchopulmonary, cardiovascular, oncological or CNS-degenerative disorders.

Also provided by the present invention are pharmaceutical compositions comprising a compound according to the present invention, as active ingredient, together with a pharmaceutically acceptable adjuvant, diluent or carrier.

DETAILED DESCRIPTION OF THE INVENTION

The present invention provides a compound of formula (I):

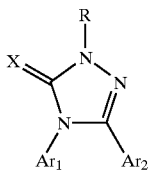

wherein: one of $Ar_1$ and $Ar_2$ is optionally substituted bicyclic heteroaryl or optionally substituted tricyclic heteroaryl and the other is optionally substituted heteroaryl or optionally substituted aryl; X is O or, when one of $Ar_1$ and $Ar_2$ is optionally substituted bicyclic heteroaryl or optionally substituted tricyclic heteroaryl and the other is optionally substituted heteroaryl then X may also be S; and R is H, OH, $NH_2$ or $C_{1-6}$ alkyl (itself optionally substituted by amino or hydroxy); or a salt or solvate thereof, or a solvate of a salt thereof; provided that when X is O, R is hydrogen and one of $Ar_1$ and $Ar_2$ is phenyl or phenyl optionally mono-substituted by halogen or $C_{1-4}$ alkyl then the other is not 3,4-methylenedioxyphenyl, unsubstituted benzthiazol-2-yl, a phthalimide or 1,8-naphthalimide.

Heteroaryl includes monocyclic, bicyclic and tricyclic heteroaryl. Heteroaryl includes pyridinyl, pyridin-2-onyl, thienyl, furyl, pyrrolyl, pyrazolyl, quinolinyl, isoquinolinyl, xanthen-9-yl, quinolizin-3-yl, benzothienyl, benzofuryl, indazolyl, 9H-pyrido[3,4-b]indolyl, 1H-pyrrolo[2,3-b]pyridinyl, 6,7,8,9-tetrahydro-pyrido[1,2-a]indolyl, 2,3-dihydro-1H-pyrrolo[1,2-a]indolyl, indolyl and benzothiophenyl. In one aspect the present invention provides a compound of formula (I) wherein $Ar_1$ and $Ar_2$ are both bicyclic heteroaryl (wherein each heteroaryl has a single heteroatom, such as a N, O or S atom).

It is preferred that aryl is phenyl or naphthyl.

In another aspect $Ar_1$ and $Ar_2$ are selected from pyridinyl, pyridin-2-onyl, thienyl, furyl, pyrrolyl, pyrazolyl, quinolinyl, isoquinolinyl, xanthen-9-yl, quinolizin-3-yl, benzothienyl, benzofuryl, indazolyl, 9H-pyrido[3,4-b]indolyl, 1H-pyrrolo[2,3-b]pyridinyl, 6,7,8,9-tetrahydro-pyrido[1,2-a]indolyl, 2,3-dihydro-1H-pyrrolo[1,2-a]indolyl, indolyl, benzothiophenyl, naphthyl and phenyl.

In a further aspect the present invention provides a compound of formula (I) wherein heteroaryl and bicyclic heteroaryl are, independently, substituted indolyl, such as substituted indol-3-yl, for example substituted at the 1 position.

In another aspect the optional substituents on the heteroaryl (such as mono-, bi- or tri-cyclic heteroaryl) and aryl groups are selected from the group comprising: halo, cyano, nitro, hydroxy, $CO_2(C_{1-4}$ alkyl), $C_{1-8}$ alkyl (optionally substituted by halo, hydroxy, cyano, $C_{1-4}$ alkoxy (optionally substituted by $NH_2$, $CO_2(C_{1-4}$ alkyl)), $NR^aR^b$, SC(=NH)$NH_2$, C(=NH)$NR^cR^d$, N=C(R$^e$)NR$^f$R$^g$, N(R$^h$)C(=O)R$^i$, NHC(=NH)$NH_2$, heterocyclyl (optionally substituted by $C_{1-4}$ alkyl or phenyl($C_{1-4}$)alkyl), phenyl (optionally substituted by $C_{1-4}$ alkyl (itself optionally substituted by amino), C(=NH)OR$^j$, C(=NH)NR$^k$R$^l$), pyridinyl (optionally substituted by $C_{1-4}$ alkyl (itself optionally substituted by amino))), $C_{5-6}$ cycloalkyl (optionally substituted by hydroxy, NR$^m$R$^n$ or alkyl (itself optionally substituted by NR$^o$R$^p$)), $C_{5-6}$ cycloalkenyl (optionally substituted by NR$^q$R$^r$ or alkyl (itself optionally substituted by NR$^s$R$^t$)), heterocyclyl (optionally substituted by $C_{1-4}$ alkyl or $C_{1-4}$ haloalkyl), phenyl (optionally substituted by halo), $C_{1-6}$ alkoxy (optionally substituted by phenyl), phenoxy and amino (optionally substituted by $C_{1-4}$ alkyl); wherein $R^a$, $R^b$, $R^m$, $R^n$, $R^o$, $R^p$, $R^q$, $R^r$, $R^s$ and $R^t$ are, independently, hydrogen or $C_{1-4}$ alkyl (itself optionally substituted by hydroxy, phenyl, $CO_2H$ or $CO_2(C_{1-4}$ alkyl)); and, $R^c$, $R^d$, $R^e$, $R^f$, $R^g$, $R^h$, $R^i$, $R^j$, $R^k$ and $R^l$ are, independently, hydrogen, $C_{1-4}$ alkyl or phenyl($C_{1-4}$)alkyl; or $R^k$ and $R^l$ join to form a heterocyclic ring (such as morpholine).

In a further aspect X is oxygen.

Salts of the compounds of formula (I) are preferably pharmaceutically acceptable salts. pharmaceutically acceptable salts of compounds of the present invention are preferably those well known in the art as being suitable for, for example, acid addition salts (such as hydrochloride, hydrobromide or acetate salts) or a salt of a compound of formula (I) with an alkyl halide (such as methyl bromide).

Solvates of the compounds or salts of the present invention are conveniently hydrates, such as monohydrates or dihydrates.

Compounds of the present invention include all stereoisomers and mixtures thereof in all proportions.

In a still further aspect the present invention provides a compound of formula (II) or (II):

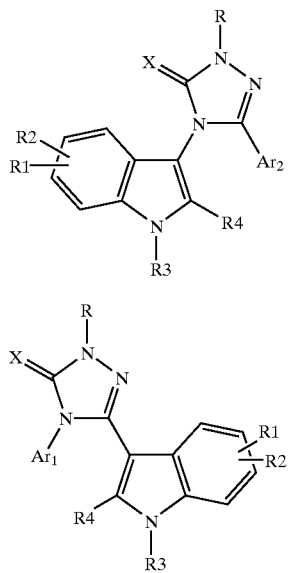

(II)

(III)

wherein: $Ar_1$ and $Ar_2$ are optionally substituted heteroaryl or optionally substituted aryl: R is hydrogen or $C_{1-3}$ alkyl; X is O or, when $Ar_1$ or $Ar_2$ is optionally substituted heteroaryl X may also be S; R1 and R2 are each independently H, $C_{1-6}$ alkyl, halogen, $C_{1-3}$ alkoxy, benzyloxy, hydroxy, cyano, fluoro substituted ($C_{1-3}$) alkyl, carboxy or carbo($C_{1-3}$) alkoxy; R3 is H, $C_{1-6}$ alkyl, benzyl, $C_{1-3}$ alkoxy substituted benzyl, hydroxy($C_{1-6}$)alkyl, hydroxy($C_{3-7}$)cycloalkyl, nitrile ($C_{1-6}$)alkyl, azido($C_{1-6}$)alkyl, amino($C_{1-6}$)alkyl, amino($C_{3-7}$)cycloalkyl, aminomethyl($C_{3-7}$)cycloalkyl, amino($C_{5-7}$) cycloalkenyl, (mono- or di- $C_{1-6}$alkyl) amino($C_{1-6}$)alkyl, benzylamino($C_{1-6}$)alkyl, (mono- or di-$C_{1-6}$alkyl) amino($C_{3-7}$)cycloalkyl, (mono- or di-$C_{1-6}$alkyl) aminomethyl($C_{3-7}$) cycloalkyl, (amino($C_{3-7}$)alkylphenyl)($C_{1-3}$)alkyl, amino($C_{1-3}$)alkylphenyl, guanidino($C_{1-6}$)alkyl, amidino($C_{1-6}$)alkyl, amidinothio($C_{1-6}$)alkyl, [N,N-di-($C_{1-6}$)alkyl]amidino($C_{1-6}$) alkyl, amidino($C_{1-3}$)alkylphenyl, [N,N-mono- or di-($C_{1-6}$) alkyl]amidino($C_{1-3}$)alkylphenyl, (N-benzyl)amidino($C_{1-3}$) alkylphenyl, (4-morpholinyl)imino($C_{1-3}$)alkylphenyl, benzimic acid methyl ester($C_{1-3}$)alkyl, hydroxy($C_{1-3}$) alkylamino ($C_{1-6}$)alkyl, carboxy($C_{1-3}$)alkylamino ($C_{1-6}$) alkyl, carboxymethyl($C_{1-3}$)alkylamino ($C_{1-6}$)alkyl, amino ($C_{1-3}$)alkyloxy ($C_{2-6}$)alkyl, formamide($C_{1-6}$)alkyl, (N,N-dimethyl)imidoformamide($C_{1-6}$)alkyl, or a group of the formula

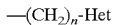
—$(CH_2)_n$-Het in which n is an integer of 0–6, and Het is an optionally substituted 5- or 6-membered heterocyclic group; R4 is H, $C_{1-3}$ alkyl or together with R3, forms an annulated ring which may be substituted by hydroxy($C_{1-3}$) alkyl or amino ($C_{1-3}$) alkyl; or a salt or a solvate thereof, or a solvate of such a salt. preferred are compounds of formula (II) and (III) in which $Ar_1$ or $Ar_2$ is optionally substituted bicyclic heteroaryl.

In another aspect the present invention provides a compound of formula (XV):

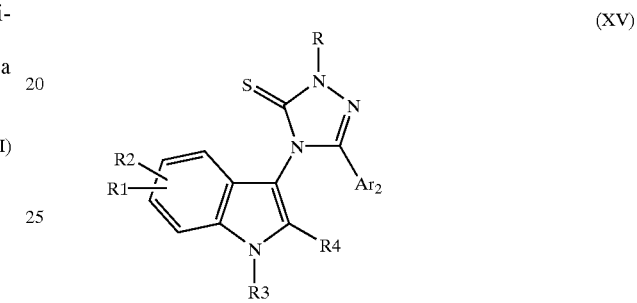

(XV)

wherein R, R1, R2, R3 and R4 are as defined above and $Ar_2$ is optionally substituted bicyclic heteroaryl or optionally substituted tricyclic heteroaryl.

In yet another aspect the present invention provides a compound of formula (IV):

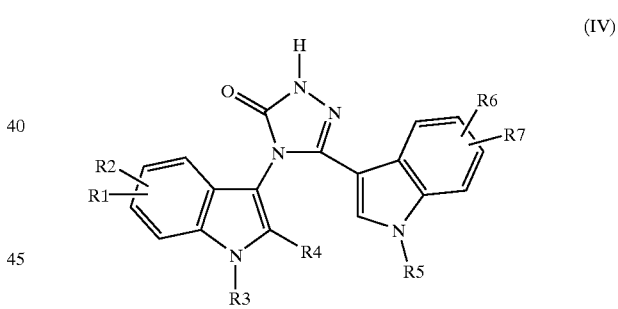

(IV)

wherein R1–R4 are as defined in formula (II) and (III); R5 is H, $C_{1-6}$ alkyl, benzyl, hydroxy($C_{1-6}$)alkyl or amino($C_{1-6}$) alkyl; R6 and R7 are each independently H, $C_{1-3}$ alkyl, halogen, fluorosubstituted $C_{1-3}$ alkyl, $C_{1-3}$ alkoxy, benzyloxy, hydroxy, cyano, carboxy or carbo($C_{1-3}$)alkoxy; or a salt or solvate thereof, or a solvate of such a salt.

For compounds of formula (IV), the following independent preferences apply: R3 or R5 is aminopropyl, aminobutyl, aminopentyl, aminocyclopentyl, aminomethylcyclopentyl, (dimethylamino) methylcyclopentyl guanidinopropyl, amidinopropyl, amidinobutyl, amidinothiopropyl, ethylaminopropyl, dimethylaminopropyl, dimethylaminobutyl, morpholinopropyl, methylpiperazinopropyl, methylpiperidinyl, piperidinomethyl, benzylpiperidinomethyl, diethylaminocyclopentyl or dimethylaminocyclopentyl;

R1, R2, R6 and R7 are each independently methyl, methoxy, cyano or halogen, preferably F or Cl.

In yet another aspect he present invention provides compounds of formula (I):

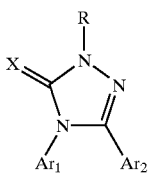

wherein:
Ar$_1$ and Ar$_2$ are
i) the same or different bicyclic heteroaromatic group (s), or
ii) independently bicyclic heteroaromatic group, and an optionally substituted aromatic or heteroaromatic group,
X is O or S, and
R is H, OH, NH$_2$, C$_{1-6}$alkyl, aminoC$_{1-6}$alkyl or hydroxyC$_{1-6}$alkyl,
and salts and solvates thereof and solvates of such salts.

In preferred embodiments of formula (I), when Ar$_1$ and/or Ar$_2$ are a bicyclic heteroaromatic or heteroaromatic group they include a single heteroatom selected from N, O and S.

In yet more preferred embodiments of formula (I), Ar$_1$ and/or Ar$_2$ are selected from benzothiophene, naphthyl, optionally substituted phenyl and optionally substituted indolyl. Optional substituents for Ar$_1$ and/or Ar$_2$ include aminopropyl, aminobutyl, ethylaminopropyl propyl, ethylaminobutyl, dimethylaminopropyl, dimethylaminobutyl, aminocyclopentyl, ethylaminocyclopentyl, dimethylaminocyclopentyl, amidinoalkyl, amidinothioalkyl and guanidinoalkyl.

Preferred embodiments of formula (I) are compounds of formula (II) and (III)

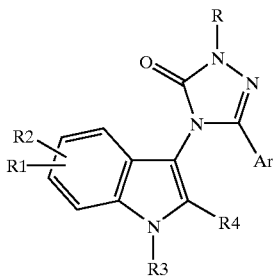

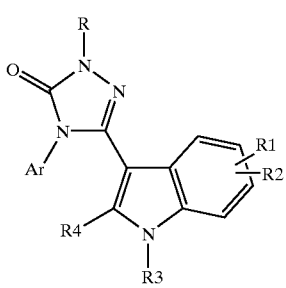

wherein:
Ar is an optionally substituted aromatic, heteroaromatic or bicyclic heteroaromatic group
R is hydrogen or C$_{1-3}$ alkyl
R1 and R2 are each independently H, C$_{1-6}$ alkyl, halogen, C$_{1-3}$ alkoxy, bensyloxy, hydroxy, carboxy, carboC1-3alkoxy, carbamoyl and C1-3 alkylcarbamoyl.

R3 is H, C$_{1-6}$alkyl, bensyl, C$_{1-3}$alkoxy substituted bensyl, hydroxyC$_{1-6}$alkyl, hydroxiC$_{3-7}$cykloalkyl, nitrileC$_{1-6}$alkyl, azidoC$_{1-6}$alkyl, aminoC$_{1-6}$alkyl, aminoC$_{3-7}$cycloalkyl, (mono- or di-C$_{1-6}$alkyl) aminoC$_{1-6}$alkyl, (mono- or di-C$_{1-6}$alkyl) aminoC$_{3-7}$cycloalkyl, (aminoC$_{1-3}$alkylphenyl)C$_{1-3}$alkyl, aminoC$_{1-3}$alkylphenyl, guanidinoC$_{1-6}$alkyl, amidinoC$_{1-6}$alkyl, amidinothioC$_{1-6}$alkyl, aminoC$_{1-6}$ alkoxy substituted alkyl, aminoC$_{1-6}$ hydroxy substituted alkyl, aminoC$_{1-6}$ amino substituted alkyl or a group of the formula —(CH$_2$)$_n$-Het in which
n is an integer of 1–6, and
Het is an optionally substituted 5- or 6-membered heterocyclic group
R4 is H, C$_{1-3}$ alkyl or together with R3, forms an annulated ring which may be substituted by hydroxyC$_{1-3}$ alkyl or aminoC$_{1-3}$ alkyl,
and salts and solvates thereof and solvates of such salts.

More preferred embodiments of formula (I) are compounds of formula (II) and (III), in which Ar is an optionally substituted bicyclic heteroaromatic group.

Even more preferred embodiments of formula (I) are compounds of formula (IV)

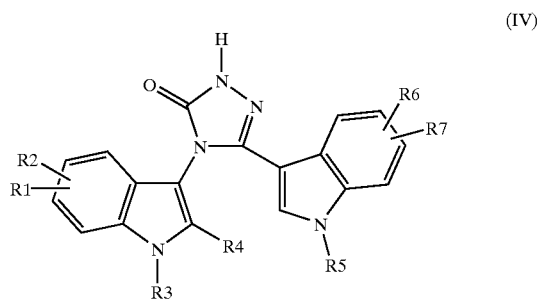

wherein
R1–R4 are as defined in formula (II) and (III),
R5 is H, C$_{1-6}$ alkyl, bensyl, hydroxyC$_{1-6}$ alkyl, aminoC$_{1-6}$ alkyl,
R6 and R7 are each independently H, C$_{1-3}$ alkyl, halogen, C$_{1-3}$ alkoxy, bensyloxy, hydroxy, carboxy, carboC1–3alkoxy, carbamoyl and C1–3 alkylcarbamoyl,
and salts and solvates thereof and solvates of such salts.

For compounds of formula (IV), the following independent preferences apply:
—R3 or R5 is aminoethyl, aminopropyl, aminobutyl, aminomethyl benzyl, aminocyclopentyl guanidinopropyl, amidinobutyl, amidinothiopropyl, ethylaminopropyl, ethylaminobutyl, dimethylaminopropyl, dimethylaminobutyl, ethylaminocyclopentyl, or dimethylaminocyclopentyl.
—R1, R2, R6 and R7 are each independently halogen, preferably F or Cl.

Preferred compounds according to the present invention include:
4-[1-(3-Aminopropyl)-5-fluoro-indol-3-yl]-5-(5-fluoro-1-methyl-indol-3-yl)-2,4dihydro-[1,2,4]triazol-3-one
4-[1-(4-Aminobutyl)-5-fluoro-indol-3-yl]-5-(5-fluoro-1-methyl-indol-3-yl)-2,4dihyro-[1,2,4]triazol-3-one
4-[1-(5-Aminopentyl)-5-fluoro-indol-3-yl]-5-(5-fluoro-1-methyl-indol-3-yl)-2,4-dihydro-[1,2,4]triazol-3-one 4-[1-(3-Dimethylamino-propyl)-5-fluoro-indol-3-yl]-5-(5-fluoro-1-methyl-indol-3-yl)-2,4-dihydro-[1,2,4]triazol-3-one 4-[1-(3-Dimethylamino-butyl)-5-fluoro-indol-3-yl]-5-(5-fluoro-1-methyl-indol-3-yl)-2,4-dihydro-[1,2,4]triazol-3-one 4-[1-(3-Ethylamino-propyl)-5-fluoro-indol-3-yl]-5-(5-fluoro-1-methyl-indol-3-yl)-2,4-dihydro-[1,2,4]triazol-3-one 4-[1-(3-Aminopropyl)-5-fluoro-indol-3-yl]-5-(1-methyl-indol-3-yl)-2,4-dihydro-[1,2,4]triazol-3-one 4-[1-(3-Aminopropyl)-5-fluoro-indol-3-yl]-5-(1H-indol-3-yl)-2,4-dihydro-[1,2,4]triazol-3-one 5-(5-Fluoro-1-methyl-indol-3-yl)-4-[5-fluoro-1-(3-morpholin-4-yl-propyl)-indol-3-yl]-2,4-dihydro-[1,2,4]triazol-3-one 5-(5-Fluoro-1-methyl-indol-3-yl)-4-{5-fluoro-1-[3-(4-methyl-piperazin-1-yl)-propyl]indol-3-yl }-2,4-dihydro-[1,2,4]triazol-3-one 2-(3-{5-Fluoro-3-[3-(5-fluoro-1-methyl-indol-3-yl)-5-oxo-1,5-dihydro-[1,2,4]triazol-4-yl]-indol-1-yl}-propyl)-isothiourea N-(3-{5-Fluoro-3-[3-(5-fluoro-1-methyl-indol-3-yl)-5-oxo-1,5-dihydro-[1,2,4]triazol-4-yl-indol-1-yl}-propyl]-guanidine 5-{5-Fluoro-3-[3-(5-fluoro-1-methyl-indol-3-yl)-5-oxo-1,5-dihydro-[1,2,4]triazol-4-yl]indol-1-yl}-butanamidine 5-{5-Fluoro-3-[3-(5-fluoro-1-methyl-indol-3-yl)-5-oxo-1,5-dihydro-[1,2,4]triazol-4-yl]indol-1-yl}-pentanamidine 4-[1(S)-(3(S)-Aminocyclopentyl)-5-fluoro-indol-3-yl]-5-(5-fluoro-1-methyl-indol-3-yl)-2,4-dihydro-[1,2,4]triazol-3-one 4-[1(R)-(3(R)-Aminocyclopentyl)-5-fluoro-indol-3-yl]-5-(5-fluoro-1-methyl-indol-3-yl)-2,4-dihydro-[1,2,4]triazol-3-one 4-[1(S)-(3(R)-Aminocyclopentyl)-5-fluoro-indol-3-yl]-5-(5-fluoro-1-methyl-indol-3yl)-2,4-dihydro-[1,2,4]triazol-3-one 4-[1(R)-(3(S)-Aminocyclopentyl)-5-fluoro-indol-3-yl]-5-(5-fluoro-1-methyl-indol-3-yl)-2,4-dihydro-[1,2,4]triazol-3-one 4-[1(S)-(3(S)-Aminocyclopentyl)-indol-3-yl]-5-(1-methyl-indol-3-yl)-2,4-dihydro-[1,2,4]triazol-3-one 4-[1(S)-(3(S)-Dimethylamino-cyclopentyl)-5-fluoro-indol-3-yl]-5-(5-fluoro-1-methyl-indol-3-yl)-2,4-dihydro-[1,2,4]triazol-3-one 4-[1(S)-(3(S)-Diethylamino-cyclopentyl)-5-fluoro-indol-3-yl]-5-(5-fluoro-1-methyl-indol-3-yl)-2,4-dihydro-[1,2,4]triazol-3-one 4-[1(S)-(3(R)-Aminomethyl-cyclopentyl)-5-fluoro-indol-3-yl]-5-(5-fluoro-1-methyl-indol-3-yl)-2,4-dihydro-[1,2,4]triazol-3-one 4-[1(S)-(3(R)-Dimethylaminomethyl-cyclopentyl)-5-fluoro-indol-3-yl]-5-(5-fluoro-1-methyl-indol-3-yl)-2,4-dihydro-[1,2,4]triazol-3-one 5-(5-Fluoro-1-methyl-indol-3-yl)-4-(5-fluoro-1-piperidin-4-ylmethyl-indol-3-yl)-2,4-dihydro-[1,2,4]triazol-3-one 5-(5-Fluoro-1-methyl-indol-3-yl)-4-[5-fluoro-1-(1-methyl-piperidin-4-yl)-indol-3-yl)-2,4dihydro-[1,2,4]triazol-3-one 4-[1-(1-Benzyl-piperidin-4-ylmethyl)-5-fluoro-indol-3-yl]-5(5-fluoro-1-methyl-indol-3yl)-2,4-dihydro-[1,2,4]triazol-3-one 4-[1-(3-Aminopropyl)-5-fluoro-indol-3-yl]-5-(1,5-dimethyl-indol-3-yl)-2,4-dihydro-[1,2,4]triazol-3-one 4-[1-(3-Aminopropyl)-5-fluoro-indol-3-yl]-5-(5-chloro-1-methyl-indol-3-yl)-2,4-dihydro-[1,2,4]triazol-3-one 4-[1-(3-Aminopropyl)-5-fluoro-indol-3-yl]-5-(5-cyano-1-methyl-indol-3-yl)-2,4-dihydro-[1,2,4]triazol-3-one 4-[1-(3-Aminopropyl)-5-fluoro-indol-3-yl]-5-(5-methoxy-1-methyl-indol-3-yl)-2,4-dihydro-[1,2,4]triazol-3-one 4-[1-(3-Aminopropyl)-5-chloro-indol-3-yl]-5-(5-chloro-1-methyl-indol-3-yl)-2,4-dihydro-[1,2,4]triazol-3-one 4-(1-Methyl-indol-3-yl)-5-(8-aminomethyl-6,7,8,9-tetrahydro-pyrido[1,2-a]indol-10-yl)-2,4-dihydro-[1,2,4]triazol-3-one or a salt or solvate thereof or a solvate of such a salt.

Preparation of the Compounds of the Invention

Compounds of formula (I) may be synthesized in the following ways:

(a) Compounds of formula (I), in which R is $C_{1-3}$ alkyl (optionally substituted by amino or hydroxy), comprising alkylating a compound of formula (I) in which R is hydrogen with the corresponding $C_{1-3}$ alkyl (optionally substituted by amino or hydroxy) alkylating agent.

(b) Compounds of formula (I), in which R is H may be synthesized by intramolecular condensation of a compound of formula (VI):

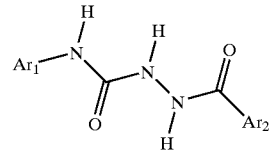

(VI)

in which $Ar_1$ and $Ar_2$ are as defined for formula (I).

(c) Compounds of formula (I) may be synthesized by converting a compound of formula (I) to a salt, especially a pharmaceutically acceptable salt thereof, or vice versa; or converting a salt, especially a pharmaceutically acceptable salt of a compound of formula (I) into a different salt, especially a pharmaceutically acceptable salt.

The condensation may be conveniently performed in the presence of trimethylsilyl triflate or bistrimethylsilyl acetamide, and a base e.g. triethylamine in dimethyl formamide at a temperature in the range of from about 100° C. to about 160° C., suitably from 115° C. to 145° C. and preferably at about 130° C., for a period of time in the range of from about 5 min to about 6 h, suitably from 15 min to 3 h, preferably for about 1h.

A compound of formula (I) wherein $Ar_1$, $Ar_2$ and/or R carries one or more functional groups which might be sensitive to, or interfere with, the reaction conditions in the processes in (a) or (b), can be prepared by using a corresponding starting material in which the functional group(s) is suitably protected and then deprotected at the end of the process of (a) or (b).

Functional groups that might be sensitive to or interfere with the reaction conditions in processes (a) or (b), as well as suitable protecting groups and deprotecting methods, are evident to those skilled in the art.

The starting materials for the above processes (a), (b) and (c) may be made by the methods described herein and particularly by those methods set out in the Examples or by methods analogous thereto. Other conventional methods for making the starting materials will be evident to those skilled in the art.

A compound of formula (II) or (III), or a salt thereof, in which at least one of R3 or Ar carries an amino or hydroxy group can be prepared by deprotecting the corresponding compound of formula (II) and (III) wherein said amino or hydroxy group is protected.

In the processes described above, the protecting groups and conditions for deprotection are well known to those skilled in the art. Suitable protecting groups for amino groups are e.g t-butoxy carbonyl groups and the deprotecting agent may be trifluoroacetic acid in a suitable solvent e.g. a mixture of acetonitrile and water. The hydroxy groups may be protected as their corresponding tert-butyldimethylsilyl (TBDMS) oxy groups and the deprotecting agent may be acetic acid in e.g. water. The deprotecting step may be carried out in a suitable solvent, e.g. tetrahydrofuran at about 60–80° C., e.g. for about 2 hours.

The use of protecting groups is fully described in "Protective Groups in Organic Chemistry", edited by J. W. F. McOmie, Plenum Press (1973) and "Protective Groups in Organic Synthesis", $2^{nd}$ edition, T. W. Greene & P. G. M. Wutz, Wiley-Interscience (1991).

Compounds of formula (II) or (III), in which R3 is an alkyl carrying an amino group, may be prepared by reduction of a compound of formula (IX) or (X) respectively:

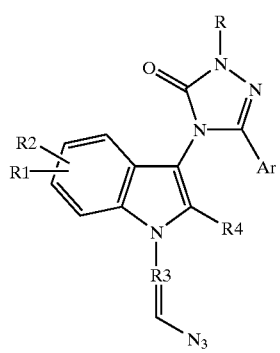
(IX)

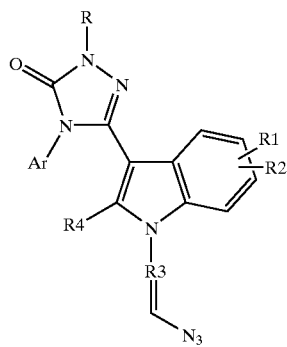
(X)

wherein R, R1, R2, R4 and Ar are as defined for formula (II) and (III), and $R3_{11}$ is an alkyl group.

In the process above, the conditions for the reduction are well known to those skilled in the art. Suitable conditions for the reduction of the azido group are e.g. hydrogenation on Pd/C at atmospheric pressure or the use of Staudinger conditions i.e. triphenyl phosphine in pyridine, followed by addition of ammonia (aq).

Compounds of formula (II) or (III), in which R3 is an alkyl carrying a thioamidino, monoalkyl amino, dialkyl amino, or a trialkyl amino group may be prepared by reaction of a compound of formula (XI) or (XII), respectively, with thiourea, or a suitable monoalkyl-, dialkyl- or trialkyl amine:

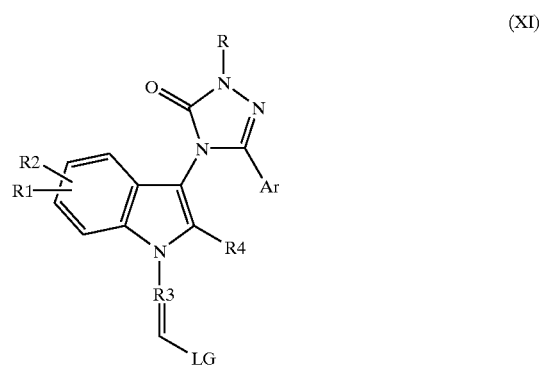
(XI)

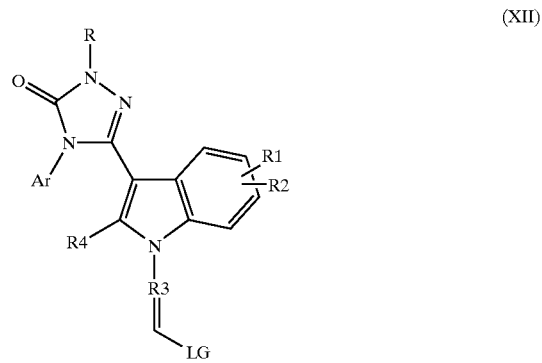
(XII)

wherein R, R1, R2, R4 and Ar are as defined in formula (II) and (III), $R3_{11}$ is an alkyl group and LG is a leaving group, e.g. mesylate or bromide.

Compounds of formula (XI) and (XII) may be synthesized by transforming under standard conditions well known to the person skilled in the art the alcohol function in compounds of formula (XIII) and (XIV):

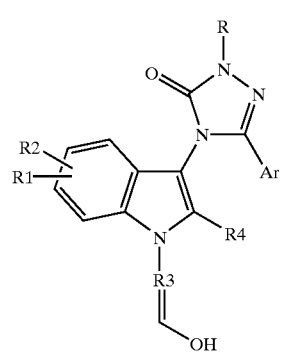
(XIII)

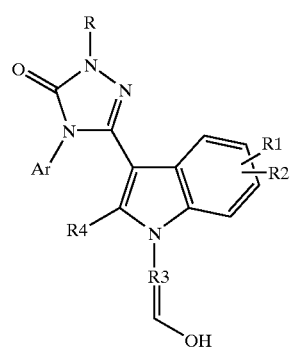
(XIV)

wherein R, R1, R2, R4 and Ar are as defined in formula (II) and (III) and R3$_{11}$ is an alkyl group.

Compounds of formula (II) in which R3 is alkyl or phenylalkyl carrying an amidino or a guanidino group may be synthesized using standard methods, from compounds of formula (XV) corresponding to formula (II), but in which R3 is alkyl carrying a nitrile or primary amine, by reacting with hydrogen chloride in ethanol followed by ammonia in methanol or by reacting with 3,5-dimethylpyrazole-1-carboxamidinium nitrate in refluxing ethanol and in the presence of a base, respectively.

Compounds of formula (II) or (III), as defined above, wherein R3 is alkyl carrying an amidino or guanidino group can be prepared by: (i) reacting a compound of formula (II) or (III), in which R3 is alkyl carrying a nitrile, with hydrogen chloride in ethanol followed by ammonia in methanol; or, (ii) reacting a compound of formula (II) or (III), in which R3 is alkyl carrying a primary amine, with 3,5-dimethylpyrazole-1-carboxamidinium nitrate in refluxing ethanol in the presence of a base.

Compounds of formula (II) or (III), as defined above, wherein R3 is alkyl or phenylalkyl carrying a N-substituted or N,N-di-substituted amidino group, can be prepared by reacting a compound of formula (II) or (III), in which R3 is alkyl or phenyl alkyl carrying a nitrile, with hydrogen chloride in methanol, followed by treatment with the appropriate amine in methanol.

Persons skilled in the art will appreciate that, in order to obtain compounds of the invention in an alternative, and, on some occasions, more convenient, manner, the individual process steps mentioned herein may be performed in a different order, and/or the individual reactions may be performed at a different stage in the overall route. This will e.g. on factors such as the nature of other functional groups present in a particular substrate, the availability of key intermediates and the protecting group strategy (if any) to be adopted.

Novel intermediates as described hereinbefore and their use in the manufacture of other compounds of the present invention also form part of the invention. Thus, according to a further aspect of the invention there is provided an intermediate compound of formula (VI), (IX), (X), (XI), (XII), (XIII) or (XIV) as defined hereinbefore, or a protected derivative of any of these compounds.

Prodrugs

It will also be appreciated by those skilled in the art that, although certain protected derivatives of compounds of formula (I), (II), (III), (IV) and (XV), which may be made prior to a final deprotection stage, may not possess pharmacological activity as such, they may be administered parenterally or orally and thereafter metabolized in the body to form compounds of the invention which are pharmacologically active. Such derivatives may therefore be described as "prodrugs". Moreover, certain compounds of formula (I), (II), (III), (IV) and (XV) may act as prodrugs of other compounds of formula (I), (II), (III), (IV) and (XV).

All prodrugs of compounds of formula (I), (II), (III), (IV) and (XV) are included within the scope of the present invention.

Medical and Pharmaceutical Use

Also provided according to the present invention are compounds of the present invention for use in medical therapy; the use of compounds of the present invention in the manufacture of medicaments for use in the treatment of the conditions described herein: and methods of medical therapy comprising the administration of a therapeutically effective amount of a compound of the present invention to an individual requiring such therapy.

The term 'medical therapy' as used herein is intended to include prophylactic, diagnostic and therapeutic regimens carried out in vivo or ex vivo on humans or other mammals.

The compounds of formula (I), (II), (III), (IV) and (XV) and pharmaceutically acceptable salts thereof, are useful because they demonstrate pharmacological activity. In particular they demonstrate activity as kinase inhibitors, especially PKC inhibitors, e.g. as is shown by their activity in the in vitro assays described in Jirousek, M. J. et al, J. Med. Chem. 1996, 39, 2664–2671; or as described in Granet, R. A. et al, Analyt. Biochem. 1987; 163, 458–463; Olsson, H. et al, Cell Signal 1989, 1, 405–410; and Chakravarthy, B. R. et al, Analyt. Biochem. 1991, 196, 144–150.

The compounds of the invention are indicated for use in the treatment of inflammatory, immunological. bronchopulmonary, cardiovascular, oncological or CNS-degenerative disorders; preferably for oral or topical treatment of inflammatory and/or immunological disorders, such as the oral or topical treatment of airway diseases involving inflammatory conditions, e.g. asthma, chronic obstructive pulmonary disease (COPD), including chronic bronchitis and emphysema; or atopic diseases, e.g. rhinitis or atopic dermatitis; inflammatory bowel diseases, e.g. Crohn's disease or colitis; autoimmune diseases e.g. multiple sclerosis, diabetes, atherosclerosis, psoriasis, systemic lupus erythematosus or rheumatoid arthritis; malignant diseases, e.g. skin or lung cancer; HIV infections or AIDS; or for inhibiting rejection of organs/transplants. The compounds of the invention are also indicated for use in treatment of heart failure, and in treatment of diabetic patients with macular edema or diabetic retinopathy.

Thus, in a further aspect the present invention provides the use of a compound of formula (I):

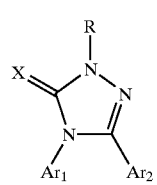

(I)

wherein: one of Ar$_1$ and Ar$_2$ is optionally substituted bicyclic heteroaryl or optionally substituted tricyclic heteroaryl and the other is optionally substituted heteroaryl or optionally substituted aryl; X is O or S; and R is H, OH, NH$_2$ or C$_{1-6}$ alkyl (itself optionally substituted by amino or hydroxy); or a salt, solvate or hydrate thereof, or a solvate or a hydrate of a salt thereof: in the manufacture of a medicament for use in the treatment of inflammatory, immunological, bronchopulmonary, cardiovascular, oncological or CNS disorders.

A method of treating a PKC mediated disease state in mammals which comprises administering to a mammal in need of such treatment an effective amount of a compound of formula (I) as defined in the preceding paragraph or a salt, solvate or hydrate thereof, or a solvate or a hydrate of a salt thereof.

Pharmaceutical Preparations

The dose of the compound to be administered will depend on the relevant indication, the age, weight and sex of the patient and may be determined by a physician. The dosage will preferably be in the range of from 0.01 mg/kg to 10 mg/kg.

The compounds may be administered topically, e.g. to the lung and/or the airways, in the form of solutions, suspensions, HFA aerosols or dry powder formulations, e.g.

formulations in the inhaler device known as the Turbuhaler®; or systemically, e.g. by oral administration in the form of tablets, pills, capsules, syrups, powders or granules, or by parenteral administration, e.g. in the form of sterile parenteral solutions or suspensions, or by rectal administration, e.g. in the form of suppositories.

The compounds of the invention may be administered on their own or as a pharmaceutical composition comprising the compound of the invention in combination with a pharmaceutically acceptable diluent, adjuvant and/or carrier. Particularly preferred are compositions not containing material capable of causing an adverse, e.g. an allergic, reaction.

Dry powder formulations and pressurized HFA aerosols of the compounds of the invention may be administered by oral or nasal inhalation. For inhalation the compound is desirably finely divided. The finely divided compound preferably has a mass median diameter of less than 10 $\mu$m, and may be suspended in a propellant mixture with the assistance of a dispersant, such as a $C_8$–$C_{20}$ fatty acid or salt thereof, (e.g. oleic acid), a bile salt. a phospholipid, an alkyl saccharide, a perfluorinated or polyethoxylated surfactant, or other pharmaceutically acceptable dispersant.

The compounds of the invention may also be administered by means of a dry powder inhaler. The inhaler may be a single or a multi dose inhaler, and may be a breath actuated dry powder inhaler.

One possibility is to mix the finely divided compound with a carrier substance, e.g. a mono-, di- or polysaccharide, a sugar alcohol, or another polyol. Suitable carriers are sugars, e.g. lactose, glucose, raffinose, melezitose, lactitol, maltitol, trehalose, sucrose, mannitol; and starch. Alternatively the finely divided compound may be coated by another substance. The powder mixture may also be dispensed into hard gelatin capsules, each containing the desired dose of the active compound.

Another possibility is to process the finely divided powder into spheres which break up during the inhalation procedure. This spheronized powder may be filled into the drug reservoir of a multidose inhaler, e.g. that known as the Turbuhaler® in which a dosing unit meters the desired dose which is then inhaled by the patient. With this system the active compound, with or without a carrier substance, is delivered to the patient.

For oral administration the active compound may be admixed with an adjuvant or a carrier, e.g. lactose, saccharose, sorbitol, mannitol; a starch, e.g. potato starch, corn starch or amylopectin; a cellulose derivative; a binder, e.g. gelatin or polyvinylpyrrolidone, and/or a lubricant, e.g. magnesium stearate, calcium stearate, polyethylene glycol, a wax, paraffin. and the like, and then compressed into tablets. If coated tablets are required, the cores, prepared as described above, may be coated with a concentrated sugar solution which may contain e.g. gum arabic, gelatin, talcum, titanium dioxide, and the like. Alternatively, the tablet may be coated with a suitable polymer dissolved in a readily volatile organic solvent.

For the preparation of soft gelatin capsules, the compound may be admixed with e.g. a vegetable oil or polyethylene glycol. Hard gelatin capsules may contain granules of the compound using either the above mentioned excipients for tablets. Also liquid or semisolid formulations of the drug may be filled into hard gelatin capsules.

Liquid preparations for oral application may be in the form of syrups or suspensions, for example solutions containing the compound, the balance being sugar and a mixture of ethanol, water, glycerol and propylene glycol. Optionally such liquid preparations may contain coloring agents. flavoring agents, saccharine and/or carboxymethylcellulose as a thickening agent or other excipients known to those skilled in art.

The compounds of the invention may also be administered in conjunction with other compounds used for the treatment of the above conditions.

The following Examples are intended to illustrate, but in no way limit the scope of the invention.

All reactions were performed in dried glassware in an argon or nitrogen atmosphere at room temperature, unless otherwise noted. Tetrahydrofuran (THF) was distilled from sodium benzophenone ketyl under $N_2$ prior to use. N,N-Dimethyl formamide (DMF) was distilled from calcium hydride and stored over molecular sieves. All other solvents and reagents were used as received.

$^1$H-NMR spectra were recorded on a Varian Inova-400 or Unity-500+ instrument. The central solvent peak of chloroform-d ($\delta_H$ 7.27 ppm), dimethylsulfoxide-$d_6$ ($\delta_H$ 2.50 ppm) or methanol-$d_4$ ($\delta_H$ 3.35 ppm) were used as internal references. Low-resolution mass spectra were recorded on an Autospec-Q, Fisons Analytical, double focusing sector instrument equipped with a LSIMS interface. Low resolution mass spectra were also obtained on a Hewlett Packard 1 100 LC-MS system equipped with an APCI ionization chamber.

Analytical HPLC was run on a Hewlett Packard LC-MS 1100, using a C-18 reversed phase column and eluting with the following general system: acetonitrile:water (20:80 to 90:10 gradient) containing 0.1% TFA. Preparative LC was run on a Kromasil KR-100-10-C18 column (250×50 mm), using different proportions of acetonitrile:water as eluent, containing 0.1% TFA.

Reversed-phased column chromatography was done with pre-packed columns (Merck, Lobar, LiChroprep RP-18 equipped with a peristaltic pump) using methanol:water and 0.1% acid (TFA, HCl. or HBr) as eluent.

Flash chromatography was performed on silica (Merck 40–63 $\mu$m) with the eluents indicated in the specific Examples.

IR was run on a Perkin Elmer 16 PC FT-IR.

EXAMPLE 1

4-[5-Fluoro-1-(3-hydroxypropyl)-indol-3-yl]-5-(5-fluoro-1-methyl-indol-3-yl)-2,4-dihydro-[1,2,4]triazol-3-one a) 5-Fluoro-indole-3-carboxylic acid methyl ester To a solution of 5-fluoroindole (2.5 g, 18.5 mmol) in dioxane (75 mL) was added pyridine (14.9 mL, 185 mmol) and trichloroacetyl chloride (10.3 mL, 92.5 mmol). The resulting mixture was stirred at 80° C. for 2.5 hours, poured into ice water and extracted with ethyl acetate. The organic phase was washed with water, brine, dried and evaporated. The residue was dissolved in dry methanol (100 mL), sodium hydroxide (0.25 g) was added and the mixture heated at 80° C. for 30 min. Most of the solvent was evaporated and the residue was partitioned between water and ethyl acetate. The organic phase was washed with brine. dried and concentrated. Purification by silica gel chromatography (heptane-ethyl acetate, 3:1/1:1) gave 3.32 g (93%) of the sub-title compound.

$^1$H NMR (400 MHz, DMSO-$d_6$): $\delta$12.02 (1H, bs,); 8.12 (1H, s); 7.62 (1H, dd); 7.46 (1H, dd); 7.04 (1H, dt); 3.78 (3H, s).

b) 1-(3-Benzyloxy-propyl)-5-fluoro-indole-3-carboxylic acid

To a solution of a) (0.86 g, 4.45 mmol) and benzyl 3-bromopropyl ether (0.78 mL, 4.45 mmol) in dry DMF (20 mL) was added potassium carbonate (2.46 g, 17.8 mmol), and the mixture was stirred under nitrogen at room temperature overnight. The mixture was partitioned between water and ethyl acetate and the organic phase was washed with water followed by brine and concentrated. The residue was dissolved in ethanol (15 mL) and sodium hydroxide in water (25%, 50 mL) was added. The reaction mixture was heated at 90° C. for 2 hours, cooled and washed with ethyl acetate. After acidification of the aqueous phase with hydrochloric acid, the product was extracted with ethyl acetate twice. The organic layers were washed with brine, dried and concentrated affording the sub-title product as an off-white solid (1.25 g, 86%).

$^1$H NMR (400 MHz, CDCl$_3$): δ7.91 (1H, s); 7.87 (1H, dd); 7.36–7.25 (6H, m); 7.01 (1H, dt); 4.46 (2H, s); 4.30 (2H, t); 3.38 (2H); 2.15–2.11 (2H, m).

c) 1-(3-Benzyloxy-propyl)-5-fluoro-indole-3-carbonyl azide

To a solution of b) (0.30 g, 0.92 mmol) in dichloromethane (20 mL) was added triethylamine (0.18 mL, 1.28 mmol) and diphenylphosphoryl azide (0.21 mL, 0.92 mmol). The mixture was stirred at room temperature overnight and then concentrated in vacuo.

The residue was purified by silica gel chromatography (heptane-ethyl acetate, 4:1) to give 0.32 g (99%) of the sub-title compound as a yellow oil.

$^1$H NMR (400 MHz, CDCl$_3$): δ0.7.90 (1H, dd); 7.81 (1H, s); 7.39–7.25 (6H, m); 7.02 (1H, dt); 4.46 (2H, s); 4.29 (2H, t); 3.38 (2H, t); 2.15–2.09 (2H, m).

d) 1-(3-Benzyloxy-propyl)-5-fluoro-3-isocyanato-indole

A solution of c) (0.17 g, 0.48 mmol) in dry toluene (10 mL) was heated at 90° C. for 6 hours. The solvent was evaporated, yielding the crude sub-title product as a yellowish oil which was immediately used in the next step without further purification.

$^1$H NMR (400 MHz, CDCl$_3$): δ7.41–7.34 (4H, m); 7.29–7.23 (3H, m); 6.99 (1H, dt); 6.90 (1H, s): 4.47 (2H, s,); 4.20 (2H, t); 3.37 (2H, t); 2.09–2.04 (2H, m).

e) 4-[1-(3-Benzyloxy-propyl)-5-fluoro-indol-3-yl]-1-(5-fluoro-1-methyl-indol-3-carbonyl)semicarbazide To a solution of d) (0.14 g, 0.44 mmol) in THF (10 mL) was added a solution of the product from Example 11e) (0.09 g, 0.44 mmol) in THF (5 mL). The reaction mixture was stirred at room temperature for 1 hour and then concentrated in vacuo. The residue was purified by chromatography on silica (dichloromethane-methanol, 98:2/9:1), furnishing the sub-title product, 0.18 g (75%), as a white solid.

$^1$H NMR (400 MHz, DMSO-d$_6$): δ9.77 (1H, bs); 8.58 (1H, bs); 8.15 (1H, s); 7.91 (1H, bs);(1H, 7.82 (1H, dd); 7.55 (1H, dd); 7.50 (1H, s); 7.40 (1H, dd); 7.33–7.23 (6H, m); 709 (1H, dt); 6.95 (1H, dt); 4.40 (2H, s); 4.19 (2H, t); 3.86 (3H, s); 3.34 (2H, t); 1.97 (2h, m).

APCI-MS m/z: 532 [MH+].

f) 4-[1-(3-Benzyloxy-propyl)-5-fluoro-indol-3-yl]-5-(5-fluoro-1-methyl-indol-3-yl)-2,4-dihydro-[1,2,4]triazol-3-one To a solution of e) (0.17 g, 0.33 mmol) in DMF (2 mL) was added triethylamine (0.21 mL, 1.48 mmol) followed by trimethylsilyl trifluoromethanesulfonate (0.24 mL, 1.32 mmol). The vial was sealed and heated at 130° C. for 50 min. After cooling, the mixture was partitioned between ethyl acetate and water. The organic phase was washed with brine twice, dried and concentrated. The residue was chromatographed on silica (dichloromethane-methanol, 98:2/95:5) giving 0.16 g (95%) of the sub-title compound.

$^1$H NMR (400 MHz, DMSO-d$_6$): δ11.89 (1H, bs); 7.70 (1H, dd); 7.65 (1H, s); 7.62 (1H, dd); 7.44 (1H, dd); 7.32–7.20 (5H, m); 7.09–7.03 (2H, m); 7.01 (1H, dd); 6.64 (1H, s); 4.35 (2H, s); 4.32 (2H, t); 3.50 (3H, s); 3.35 (2H, t); 2.04 (2H, t).

APCI-MS m/z: 514 [MH+].

Compound f) (100 mg, 0.20 mmol) was dissolved in ethanol (5 mL) and acetic acid (5 mL); palladium (10 wt. % on activated carbon, 60 mg) was then added. The mixture was hydrogenated at atmospheric pressure at room temperature overnight and was then filtered through Celite®, eluting with ethanol. The filtrate was concentrated in vacuo and the residue partitioned between ethyl acetate and water. The organic phase was washed with brine, dried and concentrated. Purification of the crude product by chromatography on silica (dichloromethane-methanol, 95:5/9:1) gave 51 mg (62%) of the title compound.

$^1$H NMR (400 MHz, DMSO-d$_6$): δ11.88 (1H, s); 7.75 (1H, s); 7.73 (1H, dd); 7.64 (1H, dd); 7.45 (1H, dd); 7.10–7.04 (2H, m); 6.99 (1H, dd); 6.66 (1H, s); 4.61 (1H, t); 4.31 (2H, t); 3.54 (3H, s); 3.37 (2H, dt); 1.92 (2H, m).

APCI-MS m/z: 424 [MH+].

EXAMPLE 2

4-[1-(3-Aminopropyl)-5-fluoro-indol-3-yl]-5-(5-fluoro-1-methyl-indol-3-yl)-2,4-dihydro-[1,2,4]triazol-3-one hydrochloride a) 2-(3-{5-Fluoro-3-[3-(5-fluoro-1-methyl-indol-3-yl)-5-oxo-1,5-dihydro-[1,2,4]triazol-4-yl-]-indol-1-yl}-propyl)-isoindole-1,3-dione To a solution of the product from Example 1 (80 mg, 0.189 mmol) in dry THF (10 mL) was added phthalimide (42 mg, 0.28 mmol) and triphenylphosphine (74 mg, 0.28 mmol). The mixture was cooled on an ice bath and diethyl azodicarboxylate (44 μL, 0.28 mmol) was added. The reaction mixture was allowed to reach room temperature and was then stirred overnight. Concentration and silica gel chromatography (dichloromethane-methanol, 99:1/98:2/95:5) gave 73 mg (70%) of the sub-title compound.

$^1$H NMR (400 MHz, CDCl$_3$): δ9.35 (1H, bs); 7.91 (1H, dd); 7.86–7.82 (2H, m); 7.76–7.71 (2H, m); 7.52 (1H, s): 7.31 (1H, dd); 7.15 (1H, dd); 7.05–6.97 (3H, m); 6.61 (1H, s); 4.24 (2H, t); 3.74 (2H, t); 3.53 (3H, s); 2.30 (2H, t).

APCI-MS m/z: 553 [MH+].

A mixture of a) (70 mg. 0.13 mmol) in THF (1.5 mL) and methylamine (40 wt % in water, 1.5 mL) was stirred at room temperature for 4.5 hours, concentrated in vacuo and cromatographed on silica (dichloromethane-methanol, 95:5/9:1 followed by dichloromethane-methanol, 9:1+1% ammonium hydroxide) giving the title compound as the free amine. The amine was dissolved in a minimum amount of methanol, hydrochloric acid (3M) in ethyl acetate (2 mL) was added and the resulting mixture was concentrated in vacuo and subsequently dried under vacuum, furnishing the title compound, 30 mg (51%), as a white solid.

$^1$H NMR (400 MHz, DMSO-d$_6$): δ11.91 (1H, s); 7.81 (1H, s); 7.79 (2H, bs); 7.75–7.70 (2H, m); 7.46 (1H, dd): 7.14–7.06 (2H, m); 7.03–7.0 (1H, m); 6.66 (1H, s); 4.36 (2H, t); 3.56 (3H, s); 2.76–2.64 (2H, m); 2.10–2.03 (2H, m).

APCI-MS m/z: 423 [MH+].

EXAMPLE 3

4-[1-((1S,3S)-3-Aminocyclopentyl)-5-fuoro-indol-3-yl]-5-(5-fluoro-1-methyl-indol-3-yl)-2,4-dihydro-[1,2,4]triazol-3-one hydrochloride

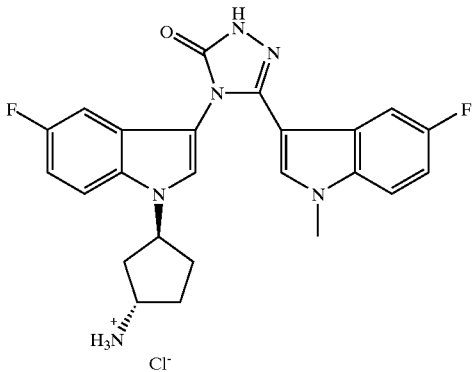

a) 1(R)-[4(S)-(tert-Butyl-dimethyl-silanyloxy)-cyclopent-2-enyl]-5-fluoro-indole-3-carboxylic acid methyl ester Sodium hydride (60% dispersion in mineral oil, 124 mg, 3.1 mmol) was weighed into a dried flask under nitrogen and mixed with dry DMF (6 mL). The product from Example 1a) (400 mg, 2.07 mmol) in dry DMF (4 mL) was added dropwise, and the resulting mixture was stirred at room temperature under nitrogen for 40 min. To this was added a mixture consisting of (1R,4S)-4-{[tert-butyl(dimethyl)silyl]oxy}-2-cyclopenten-1-yl acetate (530 mg, 2.07 mmol), tris(dibenzylideneacetone)-dipalladium(0) (104 mg, 0.11 mmol), bis(diphenylphosphino)ethane (124 mg, 0.31 mmol), lithium chloride (catalytic amount) and dry DMF (10 mL). After stirring the resulting mixture under nitrogen at room temperature overnight, ethyl acetate and water were added. The organic phase was washed with water twice followed by brine, dried and concentrated. Chromatography on silica gel (heptane-ethyl acetate. 95:5/9:1) furnished the sub-title compound, 740 mg (90%), as a yellowish oil.

$^1$H NMR (400 MHz, CDCl$_3$): δ8.00 (1H, s); 7.82 (1H, dd); 7.41 (1H, dd); 6.97 (1H, dt); 6.16–6.14 (1H, m); 5.94 (1H, dd); 5.28 (1H, m); 4.88 (1H, m); 3.86 (3H, s); 2.93–286 (1H, m); 1.82 (1H, dt); 0.89 (9H, s); 0.11 (3H, s); 0.06 (3H, s).

b) 1(S)-[3(R)-(tert-Butyl-dimethyl-silanyloxy)-cyclopentyl]-5-fluoro-indole-3-carboxylic acid methyl ester To a solution of a) (740 mg, 1.90 mmol) in ethanol (20 mL) and ethyl acetate (20 mL) was added palladium (10 wt. % on activated carbon, 70 mg). The mixture was hydrogenated at atmospheric pressure and room temperature overnight and then filtered through Celite®, eluting with ethyl acetate. The filtrate was concentrated in vacuo and then chromatographed on silica gel (heptane-ethyl acetate, 95:5), giving 510 mg (69%) of the sub-title product.

$^1$H NMR (400 MHz, CDCl$_3$): δ8.21 (1H, s); 7.82 (1H, dd); 7.37 (1H, dd); 6.97 (1H, dt); 4.85–4.78 (1H, m); 4.46–4.42 (1H, m); 3.86 (3H, s); 2.48–2.42 (1H, m); 2.27–2.21 (1H, m); 2.17–2.12 (1H, m); 2.01–1.97 (1H, m); 1.87–1.80 (2H, m); 0.92 (9H, s); 0.094 (3H, s); 0.092 (3H, s).

c) 1(S)-(3(S)-Azidocyclopentyl)-5-fluoro-indole-3-carboxylic acid methyl ester

A mixture of b) (270 mg, 0.69 mmol), THF (2.5 mL), water (2.5 mL) and acetic acid (6.5 ml) was heated at 70° C. for 3.5 hours. Ethyl acetate and water were added, the organic phase was separated and then washed with aqueous sodium hydrogen-carbonate and brine, dried and concentrated, yielding 190 mg of the crude alcohol. The alcohol was dissolved in dry THF (15 mL) under nitrogen. Diphenylphosphoryl azide (314 μL, 1.38 mmol) and triphenylphosphine (362 mg, 1.38 mmol) were added. The resulting solution was cooled on an ice bath and diethyl azodicarboxylate (0.22 mL, 1.38 mmol) was added. The reaction mixture was stirred under nitrogen at room temperature for 3.5 hours and then evaporated. Chromatography of the residue on silica (heptane-ethyl acetate, 95:5/9:1) gave 167 mg (80%) of the sub-title product.

$^1$H NMR (400 MHz, CDCl$_3$): δ7.87 (1H, s); 7.79 (1H, dd); 7.31 (1H, dd); 7.02 (1H, dt); 5.00–4.90 (1H, m); 4.32–4.26 (1H, m); 3.89 (3H, s); 2.50–2.05 (4H, m); 2.03–1.91 (2H, m).

d) 1(S)-(3(S)-Azidocyclopentyl)-5-fluoro-indole-3-carbonyl azide

A mixture of c) (164 mg, 0.54 mmol), ethanol (4 mL) and aqueous sodium hydroxide (25 wt %, 6 mL) was heated at 70° C. for 1.5 hours. After cooling, the mixture was acidified with hydrogen chloride and the product was extracted with ethyl acetate. The organic phase was washed with water twice, dried and concentrated. The residue was dissolved in dichloromethane; triethylamine (0.11 mL, 0.76 mmol) and diphenylphosphoryl azide (0.12 mL, 0.54 mmol) were added and the resulting mixture stirred at room temperature overnight. Evaporation of the solvent followed by silica gel chromatography (heptane-ethyl acetate, 95:5/9:1) yielded the sub-title compound, 144 mg (84%).

$^1$H NMR (400 MHz, CDCl$_3$): δ7.89 (1H, dd); 7.88 (1H, s); 7.32 (1H, dd); 7.05 (1H, dt); 5.00–4.90 (1H, m); 4.33–4.27 (1H, m); 2.55–2.06 (4H, m); 2.04–1.93 (2H, m).

e) 1(S)-(3(S)-Azidocyclopentyl)-5-fluoro-3-isocyanato-indole

The sub-title compound was prepared starting from d) (140 mg, 0.46 mmol) according to the procedure of Example 1d). The sub-title compound was immediately used in the next step.

$^1$H NMR (400 MHz, CDCl$_3$): δ7.31–7.23 (3H, m); 7.04 (1H, dt); 4.96–4.92 (1H, m); 4.29–4.27 (1H, m); 2.46–2.41 (1H, m); 2.37–2.25 (2H, m); 2.15–2.06 (1H, m); 1.98–1.91 (2H, m).

f) 4-[1(S)-(3(S)-Azido-cyclopentyl)-5-fluoro-indol-3-yl]-1-(5-fluoro-1-methyl-indol-3-carbonyl)semicarbazide To a solution of e) (130 mg, 0.46 mmol) in THF (15 mL) was added the product from Example 11e) (95 mg, 0.46 mmol) in portions. After stirring at room temperature for 1 h, the solvent was evaporated and the residue chromatographed on silica (dichloromethane-methanol, 98:2/95:5) giving 184 mg (81%) of the sub-title product as a white solid.

$^1$H NMR (400 MHz, DMSO-d$_6$): δ9.76 (1H, bs); 8.57 (1H, bs); 8.15 (1H, s); 7.94 (1H, bs); 7.82 (1H, dd); 7.59 (1H, s); 7.55 (1H, dd); 7.51 (1H, dd); 7.29 (1H, dd); 7.10 (1H, dt); 6.98 (1H, dt); 5.06–5.01 (1H, m); 4.40–4.38 (1H, m); 3.87 (3H, s); 2.30–2.16 (4H, m); 1.85–1.72 (2H, m).

g) 4-[1(S)-(3(S)-Azidocyclopentyl)-5-fluoro-indol-3-yl]-5-(5-fluoro-1-methyl-indol-3-yl)-2,4-dihydro-[1,2,4]triazol-3-one The sub-title compound was prepared starting from f) (180 mg, 0.36 mmol) according to the procedure of Example 1f) giving 85 mg (49%).

$^1$H NMR (400 MHz, DMSO-d$_6$): δ11.90 (1H, s); 7.93 (1H, s); 7.73–7.68 (2H, m); 7.46 (1H, dd); 7.09–6.99 (3H, m); 6.65 (1H, s); 5.19–5.14 (1H, m); 4.38–4.35 (1H, m); 3.56 (3H, s); 2.38–2.14 (4H, m); 1.88–1.70 (2H, m).

APCI-MS m/z: 447 [MH+]- N$_2$.

A mixture of g) (83 mg, 0.18 mmol), triphenylphosphine (46 mg, 0.18 mg) and pyridine (7.5 mL) was stirred at room temperature for 1.5 hours. Ammonium hydroxide (25 wt % in H$_2$O, 3 mL) was added and the reaction mixture was stirred at room temperature overnight. The solvents were evaporated and the residue was purified by silica gel chromatography (dichloromethane-methanol, 95:5/9:1/9:1+1% ammonium hydroxide). The product was dissolved in a minimum amount of methanol and hydrochloric acid (3M) in ethyl acetate (3 mL) was added. The resulting mixture was evaporated and subsequently dried under vacuum overnight, yielding 60 mg (70%) of the title compound as an off-white solid.

$^1$H NMR (400 MHz, DMSO-d$_6$): δ11.91 (1H, s); 7.96 (2H, bs); 7.93 (1H, s); 7.71–7.65 (2H, m); 7.45 (1H, dd); 7.14–7.02 (3H, m); 6.65 (1H, s); 5.27–5.23 (1H, m); 3.82–3.78 (1H, m); 3.56 (3H, s); 2.37–2.19 (4H, m); 1.96–1.91 (1H, m); 1.73–1.68 (1H, m).

APCI-MS m/z: 449 [MH+].

EXAMPLE 4

4-[1-((1S,3R)-3-Hydroxycyclopentyl)-indol-3-yl]-5-(1-methyl-indol-3-yl)-2,4-dihydro-[1,2,4]triazol-3-one

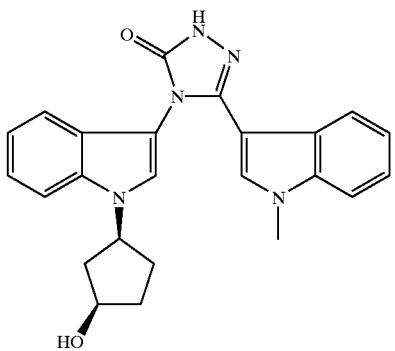

a) 1(R)-[4(S)-(tert-Butyl-dimethyl-silanyloxy)-cyclopent-2-enyl]-indole-3-carboxylic acid methyl ester The sub-title compound was prepared according to the procedure of Example 3a), starting from 1H-indole-3-carboxylic acid methyl ester (342 mg, 1.95 mmol) and acetic acid (1R,4S)-4-{[tert-butyl(dimethyl)silyl]oxy}-2-cyclopenten-1-yl acetate (500 mg, 1.95 mmol), yielding 567 mg (78%).

$^1$H NMR (400 MHz, CDCl$_3$): δ8.19–8.17 (1H, m); 7.99 (1H, s); 7.50–7.48 (1H, m); 7.26–724 (2H, m); 6.14 (1H, d); 5.95 (1H, d); 5.33–5.28 (1H, m); 4.89–4.88 (1H, m); 3.86 (3H, s); 2.94–2.87 (1H, m); 1.83 (1H, dt); 0.896 (9H, s); 0.112 (3H, s); 0.065 (3H, s).

b) 1(S)-[3(R)-(tert-Butyl-dimethyl-silanyloxy)-cyclopentyl]-1H-indole-3-carboxylic acid methyl ester The sub-title compound was prepared according to the procedure for the synthesis of Example 3b), starting from a) (630 mg, 1.69 mmol), giving 385 mg (61%).

$^1$H NMR (400 MHz, CDCl$_3$): δ8.21 (1H, s); 8.20–8.17 (1H, m); 7.46–7.43 (1H, m); 7.27–7.22 (2H, m); 4.90–4.83 (1H, m); 4.46–4.42 (1H, m); 3.87 (3H, s); 2.50–2.43 (1H, m); 2.29–2.11 (2H, m); 2.03–1.97 (1H, m); 1.90–1.80 (2H, m); 0.93 (9H, s); 0.10 (6H, s).

c) 1(S)-[3(R)-(tert-Butyl-dimethyl-silanyloxy)-cyclopentyl]-indole-3-carboxylic acid To a solution of b) (45 mg, 0.12 mmol) in dry toluene (3 mL) was added potassium trimethylsilanolate (46 mg, 0.36 mmol) and the resulting mixture was heated at 90° C. under nitrogen for 2.5 hours. After cooling, ethyl acetate and 1M acetic acid were added, the organic phase was washed with water and finally with brine, dried and evaporated. Silica gel chromatography (dichloromethane-methanol, 99:1) gave the sub-title product, 28 mg (65%).

$^1$H NMR (400 MHz, CDCl$_3$): δ8.30 (1H, s); 8.25–8.23 (1H, m); 7.50–7.47 (1H, m); 7.30–7.24 (2H, m); 4.89–4.83 (1H, m); 4.47–4.43 (1H, m); 2.52–2.45 (1H, m); 2.30–2.18 (2H, m); 2.06–2.01 (1H, m); 1.93–1.81 (2H, m); 0.937 (9H, s); 0.088 (3H, s); 0.087 (3H, s).

d) 1(S)-[3(R)-(tert-Butyl-dimethyl-silanyloxy)-cyclopentyl]-indole-3-carbonyl azide The sub-title compound was prepared according to the procedure for the synthesis of Example 1c), starting from c) (28 mg, 0.08 mmol), giving 28 mg (93%).

$^1$H NMR (400 MHz, CDCl$_3$): δ8.25–8.23 (1H, m); 8.22 (1H, s); 7.46–7.43 (1H, m); 7.28–7.20 (2H, m); 4.89–4.81 (1H, m); 4.46–4.43 (1H, m); 2.47–2.41 (1H, m); 2.30–2.22 (1H, m); 2.19–2.09 (1H, m); 2.01–1.96 (1H, m); 1.90–1.77 (2H, m); 0.920 (9H, s); 0.092 (6H, s).

e) 4-{1(S)-[3(R)-(tert-Butyl-dimethyl-silanyloxy)-cyclopentyl]-indol-3-yl}-1-(1-methyl-indol-3-carbonyl)semicarbazide A solution of d) (27 mg, 0.07 mmol) in dry toluene (3 mL) was heated at 90° C. for 6 hours. The solvent was evaporated, yielding the crude isocyanate as a yellowish oil. THF (2 mL) was added, followed by 1-methyl-indole-3-carboxylic acid hydrazide and the resulting mixture was stirred at room temperature for one hour. Evaporation of the solvent followed by silica gel chromatography (dichloromethane-methanol, 98:2) yielded the sub-title product as a white solid, 16.5 mg (43%).

$^1$H NMR (400 MHz, DMSO-d$_6$): δ9.71 (1H, bs); 8.52 (1H, bs); 8.12 (1H, d); 8.08 (1H, s); 7.90 (1H, bs); 7.56–7.47 (4H, m); 7.22 (1H, t); 7.15 (1H, t); 7.09 (1H, t); 6.98 (1H, t); 4.88–4.86 (1H, m); 4.38 (1H, m); 3.84 (3H, s); 2.07–1.67 (6H, m); 0.86 (9H, s); 0.06 (3H, s); 0.05 (3H, s).

APCI-MS m/z: 546 [MH+].

A mixture of e) (13 mg, 0.023 mmol), duisopropylethylamine (20 μL, 0.12 mmol), bis(trimethylsilyl)trifluoroacetamide (30 μL, 0.12 mmol) and DMF (2 mL) in a sealed vial was heated in a pre-heated oil bath at 130° C. for 2 hours. Ethyl acetate and water were added, the organic phase was washed with brine, dried and concentrated. The residue was chromatographed on silica gel (dichloromethane-methanol, 98:2) yielding the TBS-protected alcohol. This was dissolved in THF (200 μL), acetic acid (500 μL) and water (200 μL) and the mixture was heated at 70° C. for 2 hours. Ethyl acetate and water were added, the organic phase was washed with aqueous sodium hydrogencarbonate followed by brine, dried and concentrated in vacuo. Silica gel chromatography (dichloromethane-methanol, 99:1/98:2/95:5) gave 2.8 mg (29%) of the title compound as an off-white solid.

$^1$H NMR (400 MHz, DMSO-d$_6$): δ11.85 (1H, s); 8.08 (1H, d); 7.86 (1H, s); 7.69 (1H, d); 7.39 (1H, d); 7.21–7.17 (3H, m); 7.12 (1H, t); 7.01 (1H, t); 6.57 (1H, s); 5.25–5.02 (1H, m); 4.88 (1H, d); 4.27 (1H, m); 3.50 (3H, s); 2.21–1.78 (6H, m).

APCI-MS m/z: 414 [MH+].

EXAMPLE 5

4,5-Bis-(5-fluoro-1-methyl-indol-3-yl)-2,4-dihydro-[1,2,4]triazol-3-one a) 5-Fluoro-1-methyl-indole-3-carboxylic acid The sub-title compound was prepared according to the procedure of Example 1b), starting from the product of Example 1a) (1.4 g, 7.25 mmol) and iodomethane (0.680 mL, 10.9 mmol), yielding 1.31 g (93%).

$^1$H NMR (400 MHz, DMSO-d$_6$): δ12.04 (1H, bs); 8.07 (1H, s); 7.63 (1H, dd); 7.53 (1H, dd); 7.08 (1H, dt); 3.83 (3H, s).

b) 5-Fluoro-1-methyl-indole-3-carbonyl azide

The sub-title compound was prepared according to the procedure of Example 1c, starting from a) (400 mg, 2.07 mmol), giving 424 mg (93%).

$^1$H NMR (400 MHz, CDCl$_3$): δ7.91 (1H, dd); 7.82 (1H, s); 7.29 (1H, dd); 7.08 (1H, dt); 3.86 (3H, s).

c) 5-Fluoro-3-isocyanato-1-methyl-indole

The sub-title compound was prepared according to the procedure of Example 1d), starting from b) (106 mg, 0.49 mmol).

$^1$H NMR (400 MHz, CDCl$_3$): δ7.24–7.19 (2H, m); 7.01 (1H, dt); 6.94 (1H, s); 3.73 (3H, s).

d) 4-(5-Fluoro-1-methyl-indol-3-yl)-1-(5-fluoro-1-methyl-indol-3-carbonyl)semicarbazide The sub-title product was synthesised according to the procedure of Example 1e) starting from c) (21 mg, 0.11 mmol) and 5-fluoro-1-methyl-indole-3-carboxylic acid hydrazide (23 mg, 0.11 mmol), furnishing 22 mg (50%).

$^1$H NMR (400 MHz, DMSO-d$_6$): δ9.75 (1H, bs); 8.56 (1H, bs); 8.14 (1H, s); 7.91 (1H, bs); 7.80 (1H, dd); 7.54 (1H, dd); 7.45 (1H, s); 7.38 (1H, dd); 7.28 (1H, dd); 7.08 (1H, dt); 6.97 (1H, dt); 3.85 (3H, s); 3.72 (3H, s).

APCI-MS m/z: 398 [MH+].

The title compound was prepared according to the procedure of Example 1f), starting from d) (20 mg, 0.05 mmol), giving 12.5 mg (65%).

$^1$H NMR (400 MHz, DMSO-d$_6$): δ11.87 (1H, s); 7.76 (1H, dd); 7.74 (1H, s); 7.61 (1H, dd); 7.44 (1H, s); 7.08 (2H, dt); 6.96 (1H, dd); 6.71 (1H, s); 3.87 (3H, s); 3.55 (3H, s).

APCI-MS m/z: 380 [MH+].

EXAMPLE 6

5-[1-(3-Aminopropyl)-5-fluoro-indol-3-yl]-4-(5-fluoro-1-methyl-indol-3-yl)-2,4-dihydro-[1,2,4]triazol-3-one hydrochloride a) 1-[1-(3-Benzyloxypropyl)-5-fluoro-indol-3-yl]-4-(5-fluoro-1-methyl-indol-3-carbonyl)semicarbazide The sub-title compound was prepared according to the procedure of Example 1e), starting from 5c) (80 mg, 0.42 mmol) and 1-(3-benzyloxy-propyl)-5-fluoro-indole-3-carboxylic acid hydrazide (140 mg, 0.42 mmol), giving 185 mg (82%).

$^1$H NMR (400 MHz, DMSO-d$_6$): δ9.76 (1H, bs); 8.56 (1H, bs); 8.21 (1H, s); 7.91 (1H, bs); 7.81 (1H, dd); 7.56 (1H, dd); 7.45 (1H, s); 7.38 (1H, dd); 7.33–7.26 (6H, m); 7.06 (1H, t); 6.97 (1H, t); 4.44 (2H, s); 4.30 (2H, t); 3.72 (3H, s); 3.40 (2H, t); 2.06–2.03 (2H, m).

APCI-MS m/z: 532 [MH+].

b) 5-[1-(3-Benzyloxypropyl)-5-fluoro-indol-3-yl]-4-(5-fluoro-1-methyl-indol-3-yl)-2,4-dihydro-[1,2,4]triazol-3-one The sub-title compound was prepared according to the procedure of Example 1f), starting from a) (180 mg, 0.34 mmol), giving 130 mg (74%).

$^1$H NMR (400 MHz, DMSO-d$_6$): δ11.89 (1H, s); 7.77 (1H, dd); 7.71 (1H, s); 7.53 (1H, dd); 7.47 (1H, dd); 7.33–7.23 (3H, m); 7.19–7.17 (2H, m); 7.08–7.01 (2H, m); 6.91 (1H, dd); 6.68 (1H, s); 4.14 (2H, s); 4.00 (2H, t); 3.80 (3H, s); 2.99 (2H, t); 1.66–1.63 (2H, m).

APCI-MS m/z: 514 [MH+].

c) 2-(3-{-5-Fluoro-3-[4-(5-fluoro-1-methyl-indol-3-yl)-5-oxo-4,5-dihydro-[1,2,4,]triazol-3-yl]-indol-1-yl}-propyl)-isoindole-1,3-dione Compound b) (90 mg, 0.18 mmol), was deprotected following the procedure of Example 1, yielding the alcohol which subsequently was transformed into the sub-title compound according to the procedure of Example 2a), furnishing 60 mg (32%).

$^1$H NMR (400 MHz, DMSO-d$_6$): δ11.88 (1H, s); 7.85–7.81 (2H, m); 7.77 (1H, dd); 7.76 (1H, s); 7.62–7.49 (3H, m); 7.46 (1H, dd); 7.06 (1H, dt); 6.94 (1H, s); 6.91–6.8 (2H, m); 4.00 (2H, t); 3.85 (3H, s); 3.07 (2H, t); 1.74–1.67 (2H, m).

APCI-MS m/z: 553 [MH+].

The title compound was synthesised according to the procedure of Example 2, starting from c) (60 mg, 0.11 mmol). The hydrochloride was obtained as an off-white solid, 31 mg (62%).

$^1$H NMR (400 MHz, DMSO-d$_6$): δ11.92 (1H, s); 7.74 (1H, dd); 7.72 (1H, s); 7.62–7.54 (4H, m); 7.13–7.05 (2H, m); 6.94 (1H, dd); 6.79 (1H, s); 4.05 (2H, t); 3.87 (3H, s,); 2.48 (2H, t); 1.77–1.72 (2H, m).

APCI-MS m/z: 423 [MH+] (free base).

EXAMPLE 7

5-(1H-Indol-3-yl)-4-naphthalen-1-yl-2,4-dihydro-[1,2,4]triazol-3-one

The title compound was prepared according to the method described in Example 5 starting from naphthalene-1-carbonyl azide and 1H-Indole-3-carboxylic acid hydrazide.

$^1$H NMR (400 MHz, DMSO-d$_6$): δ12.08 (1H, s,); 11.10 (1H,s); 8.21–8.16 (2H,m); 8.11 (1H, dd, J 8.3 Hz); 7.68–7.74 (2H, m); 7.60 (1H, dd); 7.52–7.55 (2H, m); 7.33 (1H, d); 7.10–7.19 (2H, m), 6.13 (1H, d).

APCI-MS m/z: 328 [MH+].

EXAMPLE 8

4-[1-((1S,3S)-3-Aminocyclopentyl)-indol-3-yl]-5-(1-methyl-indol-3-yl)-2,4-dihydro-[1,2,4]triazol-3-one hydrochloride This compound was prepared in a manner analogous to Example 3 starting from the product from Example 4b) and 1-methyl-indole-3-carboxylic acid hydrazide.

$^1$H NMR (400 MHz, DMSO-d$_6$): δ11.88 (1H, s); 8.06 (1H, d); 7.98 (2H, bs); 7.86 (1H, s); 7.64 (1H, d); 7.40 (1H, d); 7.27–7.18 (3H, m); 7.12 (1H, dt); 7.07 (1H, dt); 6.55 (1H, s); 5.31–5.23 (1H, m); 3.94–3.70 (1H, m); 3.51 (3H, s); 2.39–2.33 (1H, m); 2.30–2.24 (3H, m); 2.01–1.93 (1H, m); 1.77–1.70 (1H, m).

APCI-MS m/z: 413 [MH+] (free base).

EXAMPLE 9

4-[1-((1S,3S)-3-Dimethylamino-cyclopentyl)-5-fluoro-indol-3-yl]-5-(5-fluoro-1-methyl-indol-3-yl)-2,4-dihydro-[1,2,4]triazol-3-one trifluoroacetate The product from Example 3 (0.05 g, 0.116 mmol) was dissolved in methanol (5 mL). To this solution was added glacial acetic acid (0.6 mL), formaldehyde (0.71 mL, 37% in water) and sodium triacetoxyborohydride (0.50 g, 2.36 mmol). The flask was sealed and the mixture was stirred for 3 hours. The solvent was evaporated, and the residue was purified on silica (dichloromethane-methanol, 95:5/90:10 followed by dichloromethane-methanol-ammonium hydroxide 75:5:0.5). The pure fractions were collected and evaporated. The residue was dissolved in a solution of sodium methoxide (10 mL, 0.1 M in methanol), and was left to stand for 1 hour. Ammonia in water (2 mL, 25%) was added and the solution was evaporated to dryness. The residue was purified on preparative HPLC (containing trifluoroacetic acid), giving 0.045 g (66%) of the title compound after lyophilization.

$^1$H NMR (500 MHz, DMSO-$d_6$): 11.94 (1H, s); 9.66 (1H, bs); 7.97 (1H, d, J 16.2 Hz); 7.76–7.68 (2H, m); 7.52–7.45 (1H, m); 7.18–7.03 (3H, m); 6.68 (1H, s); 5.16–5.10 (2H, m); 3.96–3.83 (1H, m); 3.59 (3H, s); 2.83 (6H, d, J 4.3 Hz); 2.45–2.38 (1H, m); 2.30–2.20 (2H, m); 2.03–1.93 (1H, m); 1.90–1.82 (1H, m).

EXAMPLE 10

5-(Indol-3-yl)-4-(1-methyl-indol-3-yl)-2,4-dihydro-[1,2,4]triazol-3-one

The title compound was prepared according to the method described in Example 5. 1-Methyl-indole-3-carbonyl azide was prepared according to Example 5b) and 1H-indole-3-carboxylic acid hydrazide was prepared according to literature methods.

$^1$H NMR (300 MHz, DMSO-$d_6$): 11.84 (1H, s); 11.13 (1H, bs); 8.15 (1H, d, J 7.7 Hz); 7.70 (1H, s); 7.60 (1H, d, J 8.7 Hz); 7.36 (1H, d, J 7.8 Hz); 7.28–7.03 (5H, m); 6.57 (1H, d, J 2.9 Hz); 3.89 (3H, s).

APCI-MS m/z: 330.1 [MH+].

EXAMPLE 11

4-[1-(3-Aminopropyl)-indol-3-yl]-5-(5-fluoro-1-methyl-indol-3-yl)-2,4-dihydro-[1,2,4]triazol-3-one trifluoroacetate a) 1-(3-Bromopropyl)-indole-3-carboxylic acid methyl ester In a flask was dissolved indole-3-carboxylic acid methyl ester (2.0 g, 11.4 mmole) and 1,3-dibromopropane (11.5 g, 57 mmol) in 15 mL of DMF. To this solution was added cesium carbonate (5.5 g, 17 mmol). The flask was sealed and the content was stirred at 40° C. overnight. The solution was then partitioned between ether and water. The ethereal phase was washed twice with water and once with brine and was finally evaporated. The residue was purified on silica (heptane-ethyl acetate 4:1), to give 2.2 g (75%) of the sub-title compound.

$^1$H NMR (400 MHz, CDCl$_3$): 8.21–8.16 (1H, m); 7.86 (1H, s); 7.43 (1H, m); 7.32–7.28 (2H, m); 4.37 (2H, t, J 6.5 Hz); 3.91(3H, s); 3.32 (2H, t, J 6.1 Hz); 2.39 (2H, p, J 6.2 Hz)

b) 1-(3-Azidopropyl)-indole-3-carboxylic acid methyl ester

To a solution of compound a) (0.52 g, 2 mmol) in DMF (5 mL) was added sodium azide (0.14 g, 2.2 mmol). The flask was sealed and the mixture was stirred over night. It was then partitioned between ethyl acetate and water. The organic phase was washed twice with water, once with brine and concentrated in vaccuo to give 0.48 g (93%) of the sub-title compound.

$^1$H NMR (400 MHz, CDCl$_3$): 8.23–8.18 (1H, m); 7.83 (1H, s); 7.42–7.38 (1H, m); 7.34–7.29 (2H, m); 4.29 (2H, t, J 7.0 Hz); 3.93 (3H, s); 3.31 (2H, t, J 6.4 Hz); 2.12 (2H, p, J 6.7 Hz).

c) 1-(3-Azidopropyl)-indole-3-carboxylic acid

In a flask was dissolved the compound obtained in b) (0.48 g, 1.86 mmol) in methanol (10 mL). To this solution was added sodium hydroxide (10 mL, 1N in water). The flask was sealed and stirred with heating to 75° C. overnight. The methanol was then evaporated and the residual water solution was acidified with aqueous hydrochloric acid (2N) and extracted twice with ethyl acetate. The organic phase was washed with brine and concentrated in vaccuo yielding 0.36 g (80%) of the sub-title compound as a white solid.

$^1$H NMR (400 MHz, CDCl$_3$): 8.27–8.22 (1H, m); 7.92 (1H, s); 7.42–7.37 (1H, m); 7.35–7.29 (2H, m); 4.30 (2H, t, J 6.8 Hz); 3.32 (2H, t, J 6.2 Hz); 2.13 (2H, t, J 6.3 Hz).

d) 1-(3-Azidopropyl)-indole-3-carbonyl azide

In a flask was dissolved the compound obtained in c) (0.24 g, 1.0 mmole) in dry dichloromethane (10 mL). To this solution was added triethyl amine (0.10 g, 1.0 mmole) and diphenyl phosphoryl azide (0.275 g, 1.0 mmole). The flask was sealed and the content was stirred over night. The solvent was evaporated and the residue was purified on silica (heptane-ethyl acetate, 4:1) giving 0.22 g (80%) as an oil.

$^1$H NMR (400 MHz, CDCl$_3$): δ8.30–8.25 (1H,m); 7.84 (1H,s); 7.43–7.37 (1H,m); 7.37–7.31 (2H,m); 7.30–7.24 (1H,m); 4.28 (2H,t); 3.32 (2H,t); 2.12 (2H,p).

e) 5-Fluoro-1-methyl-indol-3-carboxylic acid hydrazide

In a flask was dissolved 5-fluoro-1H-indole (10.0 g, 74 mmol) in DMF (80 mL). The flask was cooled, and sodium hydride (60% in mineral oil, 3.6 g, 89 mmol) was added in portions during 10 minutes. The mixture was stirred for an additional 10 minutes after completed addition. Iodomethane (12.6 g, 89 mmol) was added dropwise during 15 min and the mixture was stirred for another 30 min. The excess sodium hydride was quenched by cautious addition of water. The mixture was partitioned between ethyl acetate and water (250+250 mL) and the organic phase was washed twice with water and once with brine. Removal of the solvents gave 12.1 g (100%) of a solid residue.

The residue (12.0 g, 74 mmol) was dissolved in 1,4-dioxane (100 mL). Trichloroacetyl chloride (16.5 mL, 148 mmol) was added and finally pyridine (14.9 mL, 185 mmol). The solution was heated to 80° C. for 2 hours. The mixture was cooled, diluted with ethyl acetate (100 mL) and washed with aqueous hydrochloric acid (1N), saturated aqueous sodium hydrogen carbonate and brine. The organic phase was concentrated in vaccuo giving 31 g (100%) of a yellow solid.

The solid (74 mmol) was dissolved in 250 mL of THF, and hydrazinium hydroxide (7.2 mL, 148 mmol) was added. The flask was sealed and heated to 70° C. for 2 hours, whereupon a precipitate was formed. The mixture was diluted with diethyl ether and the solid was collected by filtration, giving 14.0 g (91%) of the subtitle compound.

$^1$H NMR (400 MHz, DMSO-$d_6$): 9.20 (1H, bs); 7.96 (1H, s); 7.85 (1H, d); 7.60–7.48 (1H,m); 7.10 (1H, t); 4.35 (2H, bs); 3.86 (3H, s)

f) 4-[1-(3-Azidopropyl)-indol-3-yl]-1-(5-fluoro-1-methyl-indol-3-carbonyl)semicarbazid In a 10 mL flask was dissolved the compound obtained in d) (0.069 g, 0.26 mmol) in 5 mL of toluene. The solution was heated with stirring at 110° C. for 90 minutes. The solution was then allowed to cool and was added to a suspension of the compound obtained in e) (0.050 g, 0.24 mmol) in THF (10 mL). The mixture was stirred for 1 hour, and was then concentrated in vaccuo to give the sub-title compound as a crude product, which was used without further purification.

APCI-MS m/z: 449.1 [MH+].

g) 4-[1-(3-Azidopropyl)-indol-3-yl]-5-(5-fluoro-1-methyl-indol-3-yl)-2,4-dihydro-[1,2,4]triazol-3-one In a flask was added the compound obtained in f) (0.109 g, 0.24 mmol) and DMF (5 mL). To this solution was added triethyl amine (0.12 g, 1.21 mmol) and trifluoromethanesulfonic acid trimethylsilyl ester (0.27 g, 1.21 mmol). The flask was sealed and was immersed in a pre-heated oil bath (130° C.) and heated with stirring for 1 h. The mixture was allowed to cool and ethyl acetate (15 mL) and water (15 mL) was added. The heterogeneous mixture was stirred for 15 min. The phases were allowed to separate and the aqueous phase was extracted with ethyl acetate (15 mL). The combined organic phases were washed twice with water, once with brine and finally concentrated in vaccuo. The residue was purified on silica (dichloromethane to dichloromethane-methanol, 98:2, gradient), giving 0.088 g (85%) of the sub-title compound.

$^1$H NMR (400 MHz, DMSO-d$_6$): 11.89 (1H, s); 7.73–7.68 (2H, m); 7.63 (1H, d, J 8.4 Hz); 7.44 (1H, dd, J 8.8 Hz, 4.6 Hz); 7.26–7.20 (2H, m); 7.10–7.01 (2H, m); 6.70 (1H, s);4.32 (2H, t, J 6.8 Hz); 3.53 (3H, s); 3.32 (2H, t, J 6.7 Hz); 2.05 (2H, p, J 6.6 Hz).

In a flask was added the compound obtained in g) (0.086 g, 0.20 mmol), triphenyl phosphine (0.032 g, 0.202 mmol) and of pyridine (10 mL). The flask was sealed and the content was stirred for 1 h, and ammonium hydroxide (5 mL, 25% in water) was added. The flask was sealed and the mixture was stirred over night. The solution was evaporated in vaccuo and the residue was purified on preparative HPLC (containing trifluoroacetic acid). The pure fractions where lyophilized giving 0.050 g (49%) of the title compound as a white solid.

$^1$H NMR (400 MHz, DMSO-d$_6$): 11.89 (1H, s); 7.79–7.65 (6H, m); 7.45 (1H, dd, J 10.9 Hz, 3.8 Hz); 7.28–7.21 (2H, m); 7.11–7.02 (2H, m); 6.62 (1H, s); 4.35 (2H, t, J 6.7 Hz); 3.52 (3H, s); 2.85 (2H, m); 2.08 (2H, p, J 7.2 Hz).

APCI-MS m/z: 405.1 [MH+].

EXAMPLE 12

4-[1-(3-Aminopropyl)-5-fluoro-indol-3-yl]-5-(1-methyl-indol-3-yl)-2,4-dihydro-[1,2,4]triazol-3-one trifluoroacetate The title compound was prepared according to the method described in Example 11.

$^1$H NMR (400 MHz, DMSO-d$_6$): 11.90 (1H, s); 8.08 (1H, d, J 8.3 Hz); 7.81 (1H, s); 7.78–7.70 (4H, m); 7.44 (1H, d, J 8.7 Hz); 7.24 (1H, t, J 8.2 Hz); 7.18–7.10 (2H, m); 7.06–7.01 (1H, m); 6.64 (1H, s); 4.36 (2H, t, J 7.0 Hz); 3.57 (3H, s); 2.83–2.75 (2H, m); 2.08 (2H, t, J 7.2 Hz).

APCI-MS m/z: 405.1 [MH+].

EXAMPLE 13

4-(8-Aminomethyl-6,7,8,9-tetrahydro-pyrido[1,2-a]indol-10-yl)-5-(5-fluoro-1-methyl-indol-3-yl)-2,4-dihydro-[1,2,4]triazol-3-one trifluoroacetate

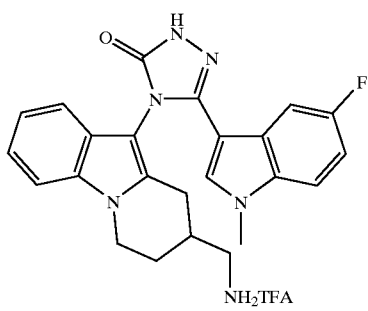

a) 8-Azidomethyl-6,7,8,9-tetrahydro-pyrido[1,2-a]indole-10-carbonyl azide

In a flask was dissolved 8-Azidomethyl-6,7,8,9-tetrahydro-pyrido[1,2-a]indole (0.30 g, 1.32 mmol, *Tetrahedron* 1991, Vol 47, No 26 pp 4645–4664) in THF (5 mL, freshly destilled). N,N-Dimethyl-4-aminopyridine (0.001 g) was added and the solution was cooled on an ice-bath. Bis-trichloromethyl carbonate (0.39 g, 1.32 mmole) was added. The reaction was allowed to reach room temperature and was stirred one hour. The mixture was concentrated in vaccuo.

The residue (1.32 mmole) was dissolved in DMF (5 mL). Sodium azide (0.095 g, 1.47 mmole) was added and the mixture was stirred over night. The mixture was then partitioned between ethyl acetate (30 mL) and water (30 mL). The organic phase was washed twice with water and once with brine and was finally evaporated to give an oil which was purified on silica (dichloromethane) giving 0.26 g (71%) of the sub-title compound as a white solid.

$^1$H NMR (400 MHz, CDCl$_3$): 8.19 (1H, d, J 8.0 Hz); 7.33–7.23 (3H, m); 4.37–4.30 (1H, m): 3.97 (1H, dt, J 11.8 Hz 5.1 Hz); 3.73 (1H, dd, J 18.7 Hz 5.1 Hz); 3.57 (1H, dd, J 12.5 Hz 5.5 Hz); 3.40 (1H, dd, J 12.3 Hz 7.4 Hz); 2.91–2.81 (1H, m); 2.36–2.28 (1H, m); 2.25–2.12 (1H, m); 1.85 (1H, dq, J 12.7 Hz 6.0 Hz).

The title compound was prepared according to the procedure described in Example 11, starting from the material obtained in a), and the compound obtained from Example 11e). The title compound was obtained as a mixture of two diastereoisomers (rotamers), stable enough to be detected by NMR at room temperature. Each rotamer is a mixture of two enantiomers. For an analogous example in which the rotamers have been isolated, see Example 69.

$^1$H NMR (400 MHz, DMSO-d$_6$): 11.92 (½H, s); 11.90 (½H, s); 7.88–7.74 (4H, m); 7.54 (1H, d, J 8.5 Hz); 7.47–7.42 (1H, m); 7.21–6.98 (4H, m); 6.66 (½H, s); 6.48 (½H, s); 4.48 (1H, t, J 14.0 Hz); 4.04 (½H, dt, J 11.8 Hz 4.8 Hz); 3.94 (½H, dt, J 11.8 Hz 4.8 Hz); 3.52 (1½H, s); 3.50 (1½H, s); 3.07–2.78 (3H, m); 2.38–2.10 (3H, m); 1.89–1.75 (1H, m).

APCI-MS m/z: 431.1 [MH+].

EXAMPLE 14

4-(8-Aninomethyl-6,7,8,9-tetrahydro-pyrido[1,2-a]indol-10-yl)-5-(1-methyl-indol-3-yl)-2,4-dihydro-[1,2,4]triazol-3-one triflouroacetate The title compound was prepared according to Example 13, starting from the compound obtained in Example 13a), and 1-methyl-indol-3-carboxylic acid hydrazide. The title compound was obtained as a mixture of two diastereoisomers (rotamers), stable enough to be detected by NMR at room temperature (cf Example 13).

$^1$H NMR (400 MHz, DMSO-d$_6$): 11.88 (½H, s); 11.86 (½H, s); 8.17 (1H, d, J 7.8 Hz); 7.81 (3H, bs); 7.54 (1H, dd, J 8.5 Hz 2.4 Hz); 7.40 (1H, d, J 8.2 Hz); 7.25–7.00 (5H, m); 6.62 (½H, s); 6.43 (½H, s); 4.48 (1H, t, J 14.8); 4.04 (½H, dt, J 12.1 Hz 4.6 Hz); 3.93 (½H, dt, J 12.0 Hz 4.5 Hz); 3.51 (1½H, s); 3.49 (1 ½H, s); 3.07–2.80 (3H, m); 2.38–2.10 (3H, m); 1.88–1.75 (1H, m).

APCI-MS m/z: 413.2 [MH+].

EXAMPLE 15

4-[1-(3-Aminopropyl)-5-fluoro-indol-3-yl]-5-(5-fluoro-1-methyl-indol-3-yl)-2-metyl-2,4-dihydro-[1,2,4]triazol-3-one hydrochloride a) 2-(3-{5-Fluoro-3-[3-(5-fluoro-1-methyl-indol-3-yl)-1-methyl-5-oxo-1,5-dihydro-[1,2,4]triazol-4-yl]-indol-1-yl}-propyl)-isoindole-1,3-dione In a vial was dissolved the product obtained in Example 2a) (0.030 g, 0.054 mmol) in DMF (1.5 mL). Cesium carbonate (0.040 g, 0.12 mmol) and iodomethane (0.05 g, 0.35 mmol) was added to the solution. The vial was sealed and stirred for 2 h at room temperature. The mixture was then partitioned between ethyl acetate and water. The organic phase was washed twice with water and once with brine, and was finally evaporated, to give 0.035 g (100%) of the sub-title compound as a yellowish solid.

APCI-MS m/z: 567.0 [MH+].

The compound obtained in a) (0.035 g, 0.061 mmol) was dissolved in THF (8 mL) and methylamine (2 mL, 40% in water) was added. The flask was sealed and stirred for 4 h, and was then concentrated in vaccuo. The residue was purified on preparative HPLC (containing hydrochloric acid), giving 0.013 g (55%) of the title compound after lyophilisation.

$^1$H NMR (400 MHz, DMSO-d$_6$): 8.01 (3H, bs); 7.86 (1H, s); 7.82 (1H, dd, J 9.5 Hz 2.4 Hz); 7.76 (1H, dd, J 9.0 Hz 4.2 Hz); 7.51–7.46 (1H, m); 7.17–7.05 (3H, m); 6.67 (1H, s); 4.40 (2H, t, J 7.0 Hz); 3.58 (3H, s); 3.51 (3H, s); 2.84–2.74 (2H, m); 2.11 (2H, p, J 7.1 Hz).

MS-LSIMS+: m/z 436.8 [MH+].

EXAMPLE 16

4-[1-(6-Aminomethyl-pyridin-2-ylmethyl)-5-fluoro-indol-3-yl]-5-(5-fluoro-1-methyl-indol-3-yl)-2,4-dihydro-[1,2,4]triazol-3-one bistrifluoroacetate a) 1-(6-Chloromethyl-pyridin-2-ylmethyl)-5-fluoro-indole-3-carboxylic acid methyl ester In a flask was dissolved the compound obtained in Example 1a) (0.10 g, 0.52 mmol), and 2,6-bischloromethylpyridine hydrochloride (0.41 g, 2.15 mmol) in DMF (5 mL). Potassium carbonate (0.43 g, 3.11 mmol) was added. The flask was sealed and heated with stirring at 50° C. for 3 h. The mixture was then partitioned between ethyl acetate and water. The organic phase was washed twice with water, once with brine, and was then concentrated. The residue was purified on silica (heptane-ethyl acetate, 2:1), giving 0.12 g (70%) of the sub-title compound as a colorless oil.

$^1$H NMR (400 MHz, CDCl$_3$): 7.96 (1H, s); 7.85 (1H, dd, J 9.6 Hz 2.5 Hz); 7.62 (1H, t, J 8.6 Hz); 7.40 (1H, d, J 8.2 Hz); 7.23 (1H, dd, J 9.4 Hz and 4.5 Hz); 6.98 (1H, dt, J 9.3 Hz and 2.5 Hz); 6.72 (1H, d, J 7.5 Hz); 5.45 (2H, s); 4.67 (2H, s); 3.93 (3H, s).

b) 1-(6-Azidomethyl-pyridin-2-ylmethyl)-5-fluoro-indole-3-carboxylic acid methyl ester The product obtained in a) (0.12, 0.36 mmol) was dissolved in DMF (5 ML). Sodium azide (0.025 g, 0.38 mmole) was added and the flask was sealed and stirred at 50° C. for 3 hours. The mixture was partitioned between ethyl acetate and water and the organic phase was washed twice with water and once with brine. Evaporation gave 0.11 g (90%) of the sub-title compound as an oil.

APCI-MS m/z: 340.0 [MH+].

c) 1-(6-Azidomethyl-pyridin-2-ylmethyl)-5-fluoro-indole-3-carbonyl azide

The sub-title compound was prepared according to the method described in Example 11 starting from the compound obtained in b).

FT-IR (cm$^{-1}$): 2131.77; 2100.95; 1668.18.

The title compound was prepared according to the method described in Example 11, starting from the compound obtained in c) and the compound obtained in Example 11e).

$^1$H NMR (400 MHz, DMSO-d$_6$): 11.99 (1H, s); 8.21 (3H, bs); 7.99 (1H, s); 7.84 (1H, t, J 8.1 Hz); 7.72 (1H, d, J 10.8 Hz); 7.67–7.62 (1H, m); 7.48 (1H, dd, J 8.8 Hz and 4.2 Hz); 7.40 (1H, d, J 7.5 Hz); 7.14–7.03 (4H, m); 6.81 (1H, s); 5.61 (2H, s); 4.19 (2H, s); 3.57 (3H, s).

MS-LSIMS+: m/z 486.1 [MH+].

EXAMPLE 17

4-[1-(3-Aminomethyl-phenyl)-5-fluoro-indol-3-yl]-5-(5-fluoro-1-methyl-indol-3-yl)-2,4-dihydro-[1,2,4]triazol-3-one trifluoroacetate a) 3-(5-Fluoro-indol-1-yl)-benzamide In a pressure resistant vessel was dissolved 5-fluoroindole (1.0 g, 7.4 mmol) and 3-fluoro-bensoenitrile (1.1 g, 7.2 mmol), 18-crown-6 (0.20 g) in DMSO (10 mL). To this solution was added potassium fluoride (38% absorbed on basic alumina. 1.8 g). The vessel was sealed and the content was heated with stirring at 130° C. for 1 h. The mixture was then allowed to cool and the suspension was partitioned between ethyl acetate and water. The organic phase was washed twice with water and once with brine. The organic phase was concentrated in vaccuo to a volume of approximately 15 mL. The residual suspension was cooled on ice and the precipitate was collected through filtration and washed with ether to give 0.40 g (20%) as a white solid.

APCI-MS: m/z 255.1 [MH+].

b) 3-(5-Fluoro-indol-1-yl)-benzoic acid methyl ester

The compound obtained in a) (0.40 g, 1.57 mmol) was suspended in methanol (10 mL) in a flask. To this suspension was added dimethyl formamide dimethyl acetal (4.72 mmol) and the flask was sealed and heated with stirring at 60° C. for 2 hours. The homogeneous solution was allowed to cool whereupon a thick precipitate was formed. The solid was collected through filtration, giving 0.32 g (85%) of the sub-title compound as a white solid.

APCI-MS: m/z 270.0 [MH+].

c) [3-(5-Fluoro-indol-1-yl)-phenyl]-methanol

In a flask was dissolved the compound obtained in b) (0.306 g, 1.13 mmol), in dry THF (15 mL) under inert atmosphere. Litium aluminium hydride (0.175 g, 4.6 mmol) was added in three portions, and the mixture was stirred for 20 minutes. The mixture was heated to reflux for 2 hours and was then allowed to cool. The reaction was quenched by cautious addition of water (166 μL), aqueous sodium hydroxide (166 μL, 10%) and water (492 μL). The residual solution was filtered through Celite®, and the filtrate was concentrated in vaccuo, giving 0.28 g (100%) of the sub-title compound as a colorless oil.

APCI-MS: m/z 242.1 [MH+].

d) 1-(3-Azidomethyl-phenyl)-5-fluoro-indole

In a flask was dissolved the compound obtained in c) (0.28 g, 1.16 mmol) in dry dichloromethane (15 mL). Triethylamine (0.117 g, 1.16 mmol) and methanesulfonyl chloride (0.133 g, 1.16 mmol) was added. The flask was sealed and the content was stirred for 1 h. The organic solution was diluted with dichloromethane and washed with water, saturated aqueous sodium hydrogen carbonate and brine. The solvent was evaporated, giving 0.36 g of the mesylate. The crude product was dissolved in DMF (5 ML) and sodium azide (0.08 g, 1.23 mmol) was added. The mixture was stirred for 1 h, and thereafter partitioned between ethyl acetate and water. The organic phase was washed with water, dried, and evaporated to give a crude product, which was purified on silica (heptane-ethyl acetate 4:1), giving 0.29 g (94%) of the sub-title compound.

$^1$H NMR (400 MHz, CDCl$_3$): 7.55 (1H, t, J 8.2 Hz); 7.50–7.44 (3H, m); 7.38 (1H, d, J 3.4 Hz); 7.35–7.29 (2H, m); 6.99 (1H, dt, J 9.2 Hz and 2.6 Hz); 6.66 (1H, d, J 3.4 Hz); 4.46 (2H, s).

e) 1-(3-Azidomethyl-phenyl)-5-fluoro-indole-3-carbonyl azide

In a flask was dissolved the compound obtained in d) (0.227 g, 0.85 mmol) in 1,4-dioxane (5 mL). To this solution was added trichloroacetyl chloride (0.756 g, 4.16 mmol) and pyridine (0.332 g, 4.20 mmol). The flask was sealed and the content was stirred at 70° C. for 6 hours, after which the solution was allowed to cool. The solution was partitioned between ethyl acetate and water and the organic phase was washed with water, aqueous sodium hydrogen carbonate and brine. The solvent was removed in vaccuo, giving 0.24 g (97%) of the intermediate.

In a flask was dissolved the intermediate above (0.85 mmol) in methanol (8 mL). To this solution was added aqueous sodium hydroxide (10 mL, 1N, 10 mmol). The flask was sealed and heated with stirring at 70° C. for 3 hours. The reaction was allowed to cool and the methanol was removed in vaccuo. The resulting water solution was acidified. The water phase was extracted twice with ethyl acetate and the organic phase was dried, filtered and evaporated to give a brownish solid.

The solid was dissolved in dichloromethane (15 mL) and triethylamine (0.086 g, 0.85 mmol) and diphenylphosphoryl azide (0.223 g, 0.85 mmol) was added. The flask was sealed and stirred at room temperature over night and the solvents were removed in vaccuo. The residue was purified on silica (heptan-ethyl acetate, 5:1), giving 0.25 g (90%) of the sub-title compound as a pale solid, which crystallized on standing.

$^1$H NMR (400 MHz, CDCl$_3$): 8.05 (1H, s); 7.99 (1H, dd, J 9.4 Hz and 2.6 Hz); 7.61 (1H, t, J 7.5 Hz); 7.50–7.37 (4H, m); 7.07 (1H, dt, J 9.2 Hz and 2.6 Hz); 4.50 (2H, s).

The title compound was prepared according to the method described in Example 11, starting from the material obtained in e) and the material obtained in Example 11e).

$^1$H NMR (400 MHz, DMSO-d$_6$): 11.99 (1H, s); 8.21 (3H, bs); 8.11 (1H, s); 7.79 (1H, s); 7.77–7.72 (2H, m); 7.67–7.62 (2H, m); 7.54–7.51 (1H, m); 7.49–7.44 (1H, m); 7.20–7.05 (3H, m); 6.91 (1H, s); 4.20 (2H, m); 3.60 (3H, s).

EXAMPLE 18

4-[1-(3-Bromopropyl)-5-fluoro-indol-3-yl]-5-(5-fluoro-1-methyl-indol-3-yl)-2,4-dihydro-[1,2,4]triazol-3-one In a flask was added the compound obtained in Example 1, (1.0 g, 2.36 mmol) in acetic acid (30 mL). To this solution was added hydrobromic acid (33% in acetic acid, 8 mL), and the flask was sealed. The flask was heated with stirring in an oil bath (80° C.) for 12 hours. The reaction was monitored on LC-MS, which confirmed the completion of the reaction. The volatiles were removed in vaccuo, and the residue was partitioned between ethyl acetate and water (50+50 mL). The organic phase was washed twice with water and once with brine and evaporated to give a 1.1 g (97%) of the title compound as a crude product, pure enough to be used further without purification.

$^1$H NMR (400 MHz, DMSO-d$_6$): 11.90 (1H, s); 7.76 (1H, s); 7.72–7.66 (2H, m); 7.45 (1H, dd, J 8.9 Hz and 4.4 Hz); 7.13–7.01 (3H, m); 6.74 (1H, s); 4.36 (2H, t, J 6.6 Hz); 3.57 (3H, s); 3.41 (2H, t, J 6.7 Hz); 2.32 (2H, p, J 6.7 Hz).

APCI-MS m/z: 486.1, 487.1, 488.0, 489.1 [MH+].

EXAMPLE 19

4-[1-(3-Bromobutyl)-5-fluoro-indol-3-yl]-5-(5-fluoro-1-methyl-indol-3-yl)-2,4-dihydro-[1,2,4]triazol-3-one The title compound was prepared according to Example 18, starting from 4-[5-fluoro-1-(4-hydroxybutyl)-indol-3-yl]-5-(5-fluoro-1-methyl-indol-3-yl)-2,4-dihydro-[1,2,4]triazol-3-one, which was prepared according to the method in Example 1.

$^1$H NMR (400 MHz, DMSO-d$_6$): 11.88 (1H, s); 7.78 (1H, s); 7.73–7.67 (2H, m); 7.45 (1H, dd, J 8.7 Hz and 4.4 Hz); 7.08 (2H, tt, J 8.9 Hz and 2.7 Hz); 7.01 (1H, dd, J 9.2 Hz and 2.5 Hz); 6.65 (1H, s); 4.29 (2H, t, J 6.8 Hz); 3.58–3.52 (5H, m); 1.90 (2H, p, J 7.5 Hz); 1.74 (2H, p, J 7.2 Hz).

APCI-MS m/z: 500.0, 501.0, 502.0, 503.0 [MH+].

EXAMPLE 20

2-(3-{5-Fluoro-3-[3-(5-fluoro-1-methyl-indol-3-yl)-5-oxo-1,5-dihydro-[1,2,4]triazol-4-yl]-indol-1-yl}-propyl)-isothiourea hydrobromide

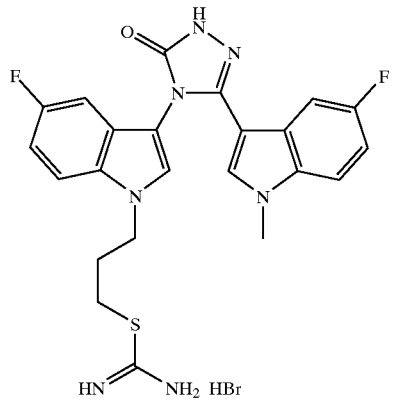

In a vial was added the compound obtained in Example 18 (0.064 g, 0.13 mmol), thiourea (0.030 g, 0.39 mmol) and ethanol (99.5%, 1.5 mL). The vial was sealed and heated with stirring at 75° C. for 4 hours. The solvent was evaporated and the residue was purified on silica (dichloromethane-methanol, 95:5 to 90:10), giving 0.061 g (82%) of the title compound as a white solid.

$^1$H NMR (400 MHz, DMSO-d$_6$): 11.96 (1H, s); 9.11 (2H, bs); 8.97 (2H, bs); 7.80 (1H, s); 7.75–7.67 (2H, m); 7.48 (1H, dd, J 9.0 Hz and 4.5 Hz); 7.16–7.02 (3H, m); 6.79 (1H, s); 4.36 (2H, t, J 7.1 Hz); 3.59 (3H, s); 3.14 (2H, t, J 7.6 Hz); 2.14 (2H, p, J 6.9 Hz).

APCI-MS: m/z 482.0, 440.0 [thiol fragment] [MH+].

EXAMPLE 21

4-[1-(3-Aminopropyl)-5-fluoro-indol-3-yl]-5-benzo[b]thiophen-3-yl-2,4-dihydro-[1,2,4]triazol-3-one trifluoroacetate The title compound was prepared according to the method described in Example 11.

$^1$H NMR (400 MHz, DMSO-d$_6$): 12.25 (1H, s); 8.38 (1H, d, J 7.9 Hz); 7.97 (1H, d, J 7.9 Hz); 7.75 (1H, s); 7.70–7.59 (4H, m); 7.48–7.37 (3H, m); 7.12–7.02 (2H, m) 4.29 (2H, t, J 6.9 Hz); 2.75–2.63 (2H, m); 2.00 (2H, p, J 7.3 Hz).

APCI-MS: m/z 408.1 [MH+].

EXAMPLE 22

4-[1-(3-Aminopropyl)-5-fluoro-indol-3-yl]-5-(indol-6-yl)-2,4-dihydro-[1,2,4]triazol-3-one trifluoacetate The title compound was prepared according to the method in Example 11, starting from 1-(3-azidopropyl)-5-fluoro-indole-3-carbonyl azide prepared the same way as Example 11d) and 1H-indole-6-carboxylic acid hydrazide (prepared by treating 1H-indole-6-carboxylic acid methyl ester with hydrazinium hydroxide).

$^1$H NMR (400 MHz, DMSO-d$_6$): 11.98 (1H, s); 11.18 (1H, s); 7.74–7.60 (5H, m); 7.46 (1H, s); 7.41–7.35 (2H, m); 7.06 (1H, dt, J 9.3 Hz and 2.3 Hz); 7.02–6.96 (2H, m); 6.36 (1H, s); 4.28 (2H, t, J 7.0 Hz); 2.77–2.65 (2H, m); 1.99 (2H, p, J 7.6 Hz).

APCI-MS: m/z 391.1 [MH+].

EXAMPLE 23

4-[1-(4-Aminobutyl)-indol-3-yl]-5-(1-methyl-indol-3-yl)-2,4-dihydro-[1,2,4]triazol-3-one trifluoacetate The title compound was prepared according to the method in Example 11.

$^1$H NMR (400 MHz, DMSO-d$_6$): 11.89 (1H, s); 8.10 (1H, d, J 8.4 Hz); 7.74 (1H, s); 7.70 (3H, bs); 7.66 (1H, d, J 8.5 Hz); 7.43 (1H, d, J 8.1 Hz); 7.28–7.21 (3H, m); 7.15 (1H, t, J 7.7 Hz); 7.05 (1H, t, J 7.3 Hz); 6.61 (1H, s); 4.31 (2H, t, J 7.2 Hz); 3.53 (3H, s); 2.89–2.80 (2H, m); 1.88 (2H, p, J 7.3 Hz); 1.57 (2H, p, J 7.6 Hz).

MS-LSIMS+: m/z 401.1 [MH+].

EXAMPLE 24

(3-{5-Fluoro-3-[3-(5-fluoro-1-methyl-indol-3-yl)-5-oxo-1,5-dihydro-[1,2,4]triazol-4-yl]-indol-1-yl}-propylamino)-acetic acid methyl ester hydrochloride In a vial was added the compound obtained in Example 18 (0.050 g, 0.1 mmol), glycine methylester (0.08 g, 0.9 mmol), and methanol (2 mL). The vial was sealed and heated with stirring at 70° C. over night. The solvent was removed in vaccuo and the residue was purified on silica (dichloromethane-methanol, 99:1 to 96:4), giving 20 mg of an oil. The oil was dissolved in methanol and aqueous hydrogen chloride (1N) was added. The methanol was removed in vaccuo and the residue was lyophilized giving the title compound as a white solid.

$^1$H NMR (400 MHz, DMSO-d$_6$): 11.91 (1H, s); 9.42 (2H, bs); 7.82 (1H, s); 7.73 (2H, dt, J 9.4 Hz and 2.8 Hz); 7.46 (1H, dd, J 8.9 Hz and 4.4 Hz); 7.15–7.05 (2H, m); 7.01 (1H, dd, J 9.4 Hz and 2.4 Hz); 6.69 (1H, s); 4.38 (2H, t, J 7.2 Hz); 4.04–3.96 (2H, m); 3.72 (3H, s); 3.57 (3H, s); 3.03–2.94 (2H, m); 2.19 (2H, p, J 7.2 Hz).

APCI-MS: m/z 495.2 [MH+].

EXAMPLE 25

4-[1-(4-Dimethylamino-butyl)-5-fluoro-indol-3-yl]-5-(5-fluoro-1-methyl-indol-3-yl)-2,4-dihydro-[1,2,4]triazol-3-one trifluoroacetate In a vial was dissolved the compound obtained in Example 19 (0.09 g, 0.18 mmol) in a solution of dimethylamine in ethanol (33%, 2 mL). The vial was sealed and heated with stirring at 70° C. for 2 hours. The solvent was evaporated and the residue was purified on preparative HPLC, containing trifluoroacetic acid. Pure fractions were lyophilized, giving 0.073 g (70%) of a white solid.

$^1$H NMR (400 MHz, DMSO-d$_6$): 11.91 (1H, s); 9.24 (1H, bs); 7.81 (1H, s); 7.75–7.68 (2H, m); 7.46 (1H, dd, J 8.9 Hz and 4.6 Hz); 7.12–7.05 (2H, m); 7.01 (1H, dd, J 9.5 Hz and 2.5 Hz); 6.69 (1H, s); 4.29 (2H, t, J 7.5 Hz); 3.55 (3H, s); 3.06–2.98 (2H, m); 2.71 (3H, s); 2.70 (3H, s); 1.80 (2H, p, J 7.4 Hz); 1.60 (2H, p, J 7.3 Hz).

APCI-MS: m/z 465.2 [MH+].

EXAMPLE 26

5-(5-Fluoro-1-methyl-indol-3-yl)-4-[5-fluoro-1-(4-morpholin-4-yl-butyl)-1-indol-3yl]-2,4-dihydro-[1,2,4]triazol-3-one trifluoroacetate In a vial was added the compound obtained in Example 19 (0.070 g, 0.14 mmol) and morpholine (2 mL). The vial was sealed and heated with stirring to 70° C. for 90 min. The excess morpholine was removed in vaccuo, and the residue was purified on preparative HPLC. The pure fractions were lyophilized, giving 0.065 g (75%) of the title compound as a white solid.

$^1$H NMR (400 MHz, DMSO-d$_6$): 11.95 (1H, s); 9.59 (1H, bs); 7.84 (1H, s); 7.77–7.69 (2H, m); 7.48 (1H, dd, J 9.1 Hz and 4.5 Hz); 7.15–7.07 (2H, m); 7.04 (1H, dd, J 9.5 Hz and 2.5 Hz); 6.71 (1H, s); 4.32 (2H, t, J 6.7 Hz); 3.98–3.90 (2H, m); 3.63–3.55 (5H, m); 3.39–3.32 (2H, m); 3.14–2.96 (4H, m); 1.85 (2H, p, J 7.6 Hz); 1.69–1.60 (2H, m).

ESI+-MS: m/z 507.2 [MH+].

EXAMPLE 27

4-[1-(3-Aminopropyl)-6-methyl-indol-3-yl]-5-(1-methyl-indol-3-yl)-2,4-dihydro-[1,2,4]triazol-3-one trifluoroacetate The compound was prepared according to the method in Example 11, starting from 6-methylindole 3-carboxylic acid methyl ester, prepared according to the method described in Example 1a), and 1-methyl-indol-3-carboxylic acid hydrazide, prepared according to Example 11e).

$^1$H NMR (400 MHz, DMSO-d$_6$): 11.87 (1H, s); 8.10 (1H, d, J 7.8 Hz); 7.71 (3H, bs); 7.64 (1H, s); 7.48 (1H, s); 7.43 (1H, d, J 8.2 Hz); 7.23 (1H, t, J 7.5 Hz); 7.15 (1H, t, J 7.4 Hz); 7.11 (1H, d, J 8.1 Hz); 6.90 (1H, d, J 8.1 Hz); 6.59 (1H, s); 4.33 (2H, t, J 7.2 Hz); 3.54 (3H, s); 2.80 (2H, t, J 7.7 Hz); 2.44 (3H, s); 2.09 (2H, p, J 7.5 Hz).

MS-LSIMS+: m/z 401.2 [MH+].

EXAMPLE 28

(3-{5-Fluoro-3-[3-(5-fluoro-1-methyl-1-indol-3-yl)-5-oxo-1,5-dihydro-[1,2,4]triazol-4-yl]-indol-1-yl}-propyl)-trimetyl-ammonium bromide In a vial was added the compound obtained in Example 18 (0.09 g, 0.19 mmol) and trimethylamine (33% in methanol, 2 mL). The vial was sealed and heated with stirring for 3 hours at 85° C. The volatiles were removed in vaccuo and the residue was purified on preparative HPLC, giving 0.080 g (80%) of the title compound as a white solid after lyophilization.

$^1$H NMR (400 MHz, DMSO-d$_6$): 11.93 (1H, s); 7.85 (1H, s); 7.79–7.72 (2H, m); 7.48 (1H, dd, J 8.9 Hz and 7.5 Hz); 7.18–7.08 (2H, m); 7.05 (1H, dd, J 9.4 Hz and 2.2 Hz); 6.79

(1H, s); 4.32 (2H, t, J 7.2 Hz); 3.60 (3H, s); 3.44–3.38 (2H, m); 3.07 (9H, s); 2.35–2.24 (2H, m).

FAB-MS: m/z 465.2 [MH+].

EXAMPLE 29

1-(3-Aminopropyl)-3-[3-(1-methyl-indol-3-yl)-5-oxo-1,5-dihydro-[1,2,4]triazol-4-yl]-1-indole-6-carbonitrile trifluoroacetate The title compound was prepared according to the method described in Example 11, starting from 6-cyanoindole 3-carboxylic acid methyl ester, prepared according to the method described in Example 1a) and 1-methyl-indol-3-carboxylic acid hydrazide, prepared according to Example 11e).

$^1$H NMR (400 MHz, DMSO-d$_6$): 11.97 (1H, s); 8.39 (1H, s); 8.08–8.03 (2H, m); 7.70 (3H, bs); 7.46–7.39 (3H, m); 7.23 (1H, t, J 7.7 Hz); 7.15 (1H, t, J 7.6 Hz); 6.66 (1H, s); 4.43 (2H, t, J 7.2 Hz); 3.57 (3H, s); 2.86 (2H, m); 2.09 (2H, p, J 7.5 Hz).

APCI-MS: m/z 412.2 [MH+].

EXAMPLE 30

4-[1-(3-Amninopropyl)-5-fluoro-1-indol-3-yl]-5-(1,6-dimethyl-indol-3-yl)-2,4-dihydro-[1,2,4]triazol-3-one triflouroacetate The title compound was prepared according to the method described in Example 11.

$^1$H NMR (400 MHz, DMSO-d$_6$): 11.87 (1H, s); 7.95 (1H, d, J 9.0 Hz); 7.81 (1H, s); 7.76–7.68 (4H, m); 7.23 (1H, s); 7.14 (1H, dt, J 9.1 Hz and 2.5 Hz); 7.04–6.97 (2H, m); 6.53 (1H, s); 4.36 (2H, t, J 6.5 Hz); 3.52 (3H, s); 2.82–2.74 (2H, m); 2.84 (3H, s); 2.08 (2H, p, J 7.4 Hz).

APCI-MS: m/z 419.2 [MH+].

EXAMPLE 31

4-[1-(Trans-4-Aminocyclohexyl)-5-fluoro-1-indol-3-yl]-5-(5-fluoro-1-methyl-indol-3yl)-2,4-dihydro-[1,2,4]triazol-3-one trifluoroacetate

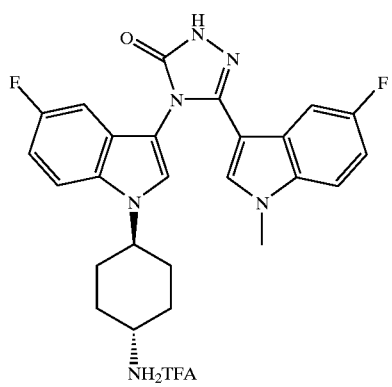

The title compound was prepared according to the method described in Example 3, from acetic acid (1R,4S)-4-(tert-butyl-dimethyl-silanoxy)-cyclohex-2-enyl ester, prepared according to literature methods.

$^1$H NMR (400 MHz, DMSO-d$_6$): 11.92 (1H, s); 7.89 (1H, s); 7.87–7.80 (4H, m); 7.73 (1H, dd, J 10.0 Hz and 2.6 Hz); 7.47 (1H, dd, J 8.8 Hz and 4.4 Hz); 7.10 (2H tt, J 9.1 Hz and 2.6 Hz); 7.03 (1H, dd, 9.4 Hz and 2.5 Hz); 6.58 (1H, s); 4.52 (1H, t, J 12.1 Hz); 3.57 (3H, s); 3.18–3.07 (1H, m); 2.09 (4H, t, J 14.7 Hz); 1.90 (2H, q, J 12.1 Hz); 1.63 (2H, q, J 12.1 Hz).

APCI-MS: m/z 463.2 [MH+].

EXAMPLE 32

4-[1-((1R,3R)-3-Amino-cyclopentyl)-5-fluoroindol-3-yl]-5-(5-fluoro-1-methyl-indol-3-yl)-2,4-dihydro-[1,2,4]triazol-3-one trifluoroacetate

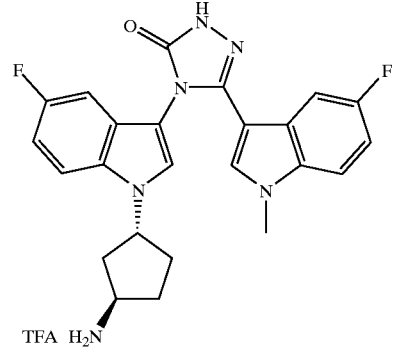

The title compound was prepared according to the method described in Example 3, starting from acetic acid (1S,4R)-4-(tert-butyl-dimethyl-silanoxy)-cyclopent-2-enyl ester.

$^1$H NMR (400 MHz, DMSO-d$_6$): 11.94 (1H, s); 7.95 (1H, s); 7.93 (3H, bs); 7.72 (1H, dd, J 10.1 Hz and 2.6 Hz); 7.67 (1H, dd, J 9.2 Hz and 4.3 Hz); 7.48 (1H, dd, J 8.9 Hz and 4.3 Hz); 7.18–7.04 (3H, m); 6.68 (1H, s); 5.23 (1H, p, J 7.2 Hz); 3.83 (1H, sext, J 6.3 Hz); 3.58 (3H, s); 2.43–2.31 (1H, m); 2.30–2.18 (3H, m); 2.02–1.90 (1H, m); 1.77–1.67 (1H, m).

MS-LSIMS+: m/z 449.2 [MH+].

EXAMPLE 33

4-[1-((1R,4S)-4-Amino-cyclopent-2-enyl)-5-fluoro-indol-3-yl]-5-(5-fluoro-1-methyl) -indol-3-yl)-2,4-dihydro-[1,2,4]triazol-3-one trifluoroacetate

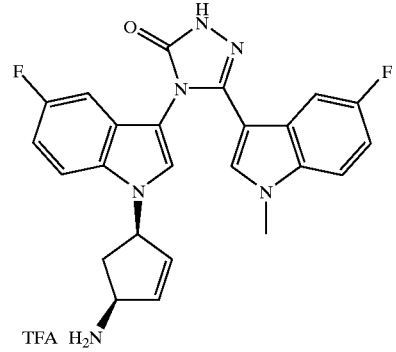

a) 1-((4S,1R)-4-Acetoxy-cyclopent-2-enyl)-5-fluoro-indole-3-carboxylic acid methyl ester In a flask was dissolved the compound obtained in Example 3a) (6.1 g, 15.7 mmol), in THF (70 mL). Tetrabutylammonium fluoride trihydrate (9.0 g, 28.5 mmol) was added and the flask was sealed, and stirred at room temperature for 1 hour. The solution was cooled on ice and pyridine (100 mL), and acetic anhydride (50 mL) was added.

The ice bath was removed after 30 minutes, and the mixture was stirred at room temperature for another 3 hours. The volatiles were removed in vaccuo and the residue was taken up in ethyl acetate and washed with water, saturated aqueous sodium hydrogen carbonate (10%) and brine. The organic solution was concentrated in vaccuo and the residue was purified on silica (toluene-ethyl acetate, 7:1), giving 4.8 g (96%) of the sub-title compound as a brownish solid.

$^1$H-NMR (400 MHz, CDCl$_3$): 7.89 (1H, s); 7.81 (1H, dd); 7.38 (1H, dd); 7.07–7.00 (1H, dt); 6.32–6.28 (1H, m); 6.20–6.16 (1H, m); 5.75–5.68 (1H, m); 5.43–5.36 (1H, m); 3.89 (3H, m); 3.16–3.06 (1H, m); 1.92–1.85 (1H, m).

b) 1-((1R,4S)-4-Azidocyclopent-2-enyl)-5-fluoro-indole-3-carboxylic acid methyl ester In a flask was dissolved the compound obtained in a) (1.0 g, 3.15 mmol), in THF (15 mL) and water (5 mL). Sodium azide (0.4 g, 6.3 mmol) was added and the mixture was degassed. Tetrakis-(Triphenylphosphine) palladium (0.36 g) was added and the mixture was stirred for 5 hours under argon. The solution was taken up in ethyl acetate and washed twice with water and once with brine. A yellow oil was obtained after evaporation, which was purified on silica (toluen-ethyl acetate, 20:1), giving 0.83 g (87%) of the sub-title compound as a yellow oil.

$^1$H-NMR (400 MHz, CDCl$_3$): 7.89–7.81 (2H, m); 7.36 (1H, dd); 7.03 (1H, dt); 6.30–6.27 (1H, m); 6.20–6.15 (1H, m); 5.46–5.39 (1H, m); 4.64–4.50 (1H, m); 3.92 (3H, s); 3.14–3.04 (1H, m); 1.96–1.88 (1H, m).

c) 1-((4S,1R)-4-Azido-cyclopent-2-enyl)-5-fluoro-indole-3-carbonyl azide

The sub-title compound was prepared according to the procedures in Example 11c) and 11d), starting from the compound obtained in b).

$^1$H-NMR (400 MHz, CDCl$_3$): 7.97–7.86 (2H, m); 7.36 (1H, dd); 7.07 (1H, dt); 6.36–6.29 (1H, m); 6.21–6.15 (1H, m); 5.46–5.38 (1H, m); 4.66–4.58 (1H, m); 3.15–3.04 (1H, m); 1.97–1.88 (1H, m).

d) 4-[1-((4S,1R)-4-Azido-cyclopent-2-enyl)-5-fluoro-indol-3-yl]-5-(5-fluoro-1-methyl-1H) -indol-3-yl)-2,4-dihydro-[1, 2,4]triazol-3-one The sub-title was prepared according to the method in Example 11g) starting from the compound obtained in c) and the hydrazide described in Example 11e).

$^1$H NMR (400 MHz, DMSO-d$_6$): 11.90 (1H, s); 7.75 (1H, dd, J 8.9 Hz and 4.2 Hz); 7.69 (1H, dd, J 10.2 Hz and 2.7 Hz); 7.58 (1H, s); 7.46 (1H, dd, J 9.0 Hz and 4.5 Hz); 7.16–7.03 (3H, m); 6.70 (1H, s); 6.31–6.26 (2H, m); 5.76–5.70 (1H, m); 4.79–4.73 (1H, m); 3.59 (3H, s); 3.17–3.06 (1H, m); 1.76–1.67 (1H, m).

The title compound was prepared according to the method described in Example 3, starting from the compound obtained in d).

$^1$H NMR (400 MHz, DMSO-d$_6$): 11.95 (1H, s); 8.10 (1H, bs); 7.84–7.74 (3H, m); 7.48 (1H, dd, J 8.9 Hz and 4.5 Hz); 7.17–7.04 (3H, m); 6.67 (1H, s); 6.28 (1H, d, J 5.3 Hz); 6.12 (1H, d, J 5.3 Hz); 5.84 (1H, t, J 7.5 Hz); 4.35–4.27 (1H, m); 3.53 (3H, s); 3.24–3.14 (1H, m); 1.77 (1H, p, J 6.5 Hz).

APCI-MS m/z: 447.1 [MH+].

EXAMPLE 34

4-[1-((1S,3R)-3-Aminocyclopentyl)-5-fluoro-indol-3-yl]-5-(5-fluoro-1-methyl-indol -3yl)-2,4-dihydro-[1,2,4]triazol-3-one trifluoroacetate In a flask was dissolved the compound obtained in Example 33d) (0.02 g, 0.042 mmol) in THF (4 mL) and acetic acid (1 mL). To this solution was added Pd/C (10%, 0.01 g), and the compound was hydrogenated at normal pressure and temperature for 3 hours. The solution was then filtered and the filtrate was evaporated. The residue was purified on preparative HPLC (containing trifluoroacetic acid), giving 0.009 g (38%) of the title compound as a white solid after lyophilization.

$^1$H NMR (400 MHz, DMSO-d$_6$): 11.95 (1H, s); 7.97–7.90 (4H, m); 7.78–7.71 (2H, m); 7.48 (1H, dd, J 8.7 Hz and 4.3 Hz); 7.17–7.03 (3H, m); 6.64 (1H, s); 5.08 (1H, p, J 8.4 Hz); 3.72–3.62 (1H, m); 3.58 (3H, s); 2.76–2.65 (1H, m); 2.29–2.19 (1H, m); 2.16–2.04 (2H, m); 1.91–1.82 (2H, m).

MS-LSIMS+: m/z 449.1 [MH+].

EXAMPLE 35

4-[1-((1R,3S)-3-Aminocyclopentyl)-5-fluoro-indol-3-yl]-5-(5-fluoro-1-methyl-indol-3-yl)-2,4-dihydro-[1,2,4]triazol-3-one trifluoroacetate The title compound was prepared according to the method described in Example 34, starting from acetic acid (1S,4R)-4-(tert-butyl-dimethyl-silanoxy)-cyclopent-2-enyl ester.

$^1$H NMR (400 MHz, DMSO-d$_6$): 11.95 (1H, s); 7.95 (3H, bs); 7.94 (1H, s); 7.77–7.70 (2H, m); 7.48 (1H, dd, J 8.7 Hz and 4.6 Hz); 7.17–7.03 (3H, m); 6.64 (1H, s); 5.08 (1H, p, J 9.0 Hz); 3.73–3.62 (1H, m); 3.58 (3H, s); 2.77–2.67 (1H, m); 2.29–2.19 (1H, m); 2.16–2.04 (2H, m); 1.93–1.82 (2H, m).

MS-LSIMS+: m/z 449.2 [MH+].

EXAMPLE 36

3-{4-[1-(3-Amninopropyl)-5-fluoro-indol-3-yl]-5-oxo-4,5-dihydro-[1,2,4]triazol-3-yl}-1-methyl-indole-6-carbonitrile trifluoroacetate The compound was prepared according to the method described in Example 11.

$^1$H NMR (400 MHz, DMSO-d$_6$): 12.03 (1H, s); 8.18 (1H, d, J 8.4 Hz); 8.13 (1H, s); 7.81 (1H, s); 7.77–7.67 (4H, m); 7.50 (1H, dd, J 8.4 Hz and 1.4 Hz); 7.13 (1H, dt, J 9.5 Hz and 2.4 Hz); 7.04 (1H, dd, J 9.2 Hz and 2.5 Hz); 6.95 (1H, s); 4.35 (2H, t, J 6.7 Hz); 3.66 (3H, s); 2.83–2.73 (2H, m); 2.07 (2H, p, J 7.5 Hz)

APCI-MS: m/z 430.2 [MH+].

EXAMPLE 37

5-(5-Fluoro-1-methyl-indol-3-yl)-4-[5-fluoro-1-(1-methyl-piperidin-4-yl)-indol-3-yl]-2,4-dihydro-[1,2, 4]triazol-3-one trifluoroacetate a) 5-Fluoro-1-(1-methyl-piperidine-4-yl)-indole-3-carbonyl azide In a flask was dissolved 5-fluoro-1-(1-methyl-piperidine-4-yl)-indole (1.0 g, 3.8 mmol, prepared according to *Tetrahedron Letters* 1996 p 6045–6048), in 1,4-dioxane (25 mL). To this solution was added pyridine (10 mL) and trichloroacetyl chloride (2.14 g, 11.4 mmol) and the flask was sealed. The flask was immersed in an oil bath and heated at 80° C. for 3 hours, when TLC confirmed complete conversion of the starting material. The cooled mixture was taken up in ethyl acetate and washed with water, saturated aqueous sodium hydrogen carbonate and brine, to give 1.73 g of a yellowish solid, which was used without further purification.

The solid was dissolved in THF (50 mL) and hydrazinium hydroxide (0.42 g, 8.4 mmole) was added. The flask was sealed and stirred at room temperature over night. The mixture was partitioned between ethyl acetate and water.

The organic phase was washed water and brine and concentrated i vaccuo to give a brownish solid. The solid was triturated with ether and pentane to give 0.60 g of a yellowish solid.

The solid was dissolved in acetic acid (20 mL) and water (20 mL). The solution was cooled to −10 ° C., when sodium nitrite (0.129 g, 1.88 mmol) dissolved in water (1 mL) was added dropwise during 20 minutes. The resulting mixture was stirred on ice for 1 hour. The mixture was allowed to reach room temperature and the acetic acid was evaporated. The resulting aqueous solution was treated with sodium carbonate and the alkaline solution was extracted twice with ethyl acetate. The combined organic solutions were dried and concentrated in vaccuo, to give an oil which was purified on silica (dichloromethane followed by to dichloromethane-methanol, 20:1). This provided 0.35 g (28%) of the sub-title compound as a yellow solid.

$^1$H NMR (400 MHz, CDCl$_3$): 8.31 (1H, s); 7.77 (1H, dd); 7.72 (1H, dd); 7.15 (1H, dt); 4.47–4.32 (1H, m); 2.87 (2H, d); 2.21 (3H, s); 2.17–2.09 (2H, m); 2.07–1.80 (4H, m).

In a flask was dissolved the compound obtained in a) (0.075 g, 0.25 mmol) in toluene (5 mL). The solution was heated at 110° C. for 90 minutes under nitrogen. The solution was then allowed to cool. The cool solution was added to a suspension of the product from Example 11e) (0.051 g, 0.25 mmol) in 20 mL of THF. The mixture was stirred for 1 hour and was then concentrated in vaccuo.

To the residue was added xylene (8 mL), triethylamine (0.165 mL, 5 equiv.) and trifluoromethanesulfonic acid trimethylsilyl ester (0.212 mL, 5 equiv.) The flask was sealed and immersed in a preheated oil bath (130° C.) for 1 hour. The emulsion was then allowed to cool, and methanol (5 mL) was added. The mixture was stirred for 15 minutes and evaporated. The residue was purified on silica (dichloromethane-methanol-ammonium hydroxide, 25% in water, 90:10:1), giving 0.055 g of a partially purified compound. This was purified on preparative HPLC (containing TFA), giving 0.045 g (31%) of the title compound after lyophilization.

$^1$H NMR (400 MHz, DMSO-d$_6$): 11.94 (1H, s); 9.56 (1H, bs); 7.90 (1H, s); 7.81–7.70 (2H, m); 7.48 (1H, dd, J 9.6 Hz and 4.4 Hz); 7.17 (1H, dt, J 9.2 Hz and 2.0 Hz); 7.11–7.05 (2H, m); 6.63 (1H, s); 4.86–4.75 (1H, m); 3.67–3.56 (2H, m); 3.59 (3H, s); 3.30–3.20 (2H, m); 2.86 (3H, s); 2.35–2.27 (2H, m); 2.21–2.07 (2H, m).

APCI-MS: m/z 463.2 [MH+].

EXAMPLE 38

4-[1-((1S,3R)-3-Aminomethyl-cyclopentyl)-5-fluoro-indol-3-yl]-5-(5-fluoro-1-methyl)-indol-3-yl)-2,4-dihydro-[1,2,4]triazol-3-one trifluoroacetate a) 1-((1R,4S)-4-Ethoxycarbonyloxy-cyclopent-2-enyl)-5-fluoro-indole-3-carboxylic acid methyl ester In a flask was dissolved the product from Example 33a) (2.6 g, 9.25 mmol) in pyridine (30 mL) under nitrogen. The solution was cooled to 0° C., and ethyl chloroformate (1.7 g, 15.7 mmol) was added during 10 minutes. The mixture was stirred for 1 hour at 0° C. and was allowed to reach the ambient temperature over night. The mixture was concentrated in vaccuo and the residue was taken up in ethyl acetate and washed with saturated aqueous ammonium chloride. aqueous hydrochloric acid (1M), saturated aqueous sodium hydrogen carbonate and brine. The organic phase was concentrated in vaccuo and the residue was purified on silica (toluene-ethyl acetate, 20:1) to give 2.85 g (87%) of an oil, which crystallized on standing.

$^1$H NMR (400 MHz, CDCl$_3$): 7.88 (1H, s); 7.85 (1H, dd); 7.38 (1H, dd); 7.03 (1H, dt); 6.38–6.34 (1H, m); 6.23–6.19 (1H, m); 5.70–5.65 (1H, m); 5.44–5.38 (1H; m); 4.21 (2H, q); 3.89 (3H, s); 3.23–3.13 (1H, m); 2.03–1.95 (1H, m); 1.34 (3H, t)

b) 5-Fluoro-1-((1R,4R)-4-nitromethyl-cyclopent-2-enyl)-indole-3-carboxylic acid methyl ester In a flask was dissolved the compound obtained in a) (1.25 g, 3.5 mmol) and triphenylphosphine (0.25 g, 9.6 mmol) in dichloromethane (15 mL, 3 Å mol sieve) and nitromethane (5 mL). The solution was degassed and kept under argon, and Pd$_2$(dba)$_3$ (0.18 g, 1.96 mmol) was added. The mixture was stirred under argon over night, and was then concentrated in vaccuo. The residue was dissolved in ethyl acetate and washed twice with water and once with brine. Evaporation of the organic phase provided a crude product, which was purified on silica (toluene-ethyl acetate, 4:1), to give 0.70 g (64%) of the sub-title compound as a colorless oil.

$^1$H NMR (400 MHz, CDCl$_3$): 7.86–7.82 (2H, m); 7.33 (1H, dd); 7.04 (1H, dt); 6.23–6.18 (1H, m); 6.14–6.11 (1H, m); 5.59–5.52 (1H, m); 4.57–4.48 (1H, m); 4.42–4.33 (1H, m); 3.94 (3H, s); 3.68–3.57 (1H, m); 3.05–2.94 (1H, m); 1.75–1.64 (1H, m)

c) 1-((1S,3R)-3-Aminomethyl-cyclopentyl)-5-fluoro-indole-3-carboxylic acid methyl ester In a flask was dissolved the compound obtained in b) (0.70 g, 2.16 mmol) in ethanol (25 mL, 95%) and ethyl acetate (25 mL) and acetic acid (3 mL). Palladium (5% on charcoal, 0.33 g) was added, and the mixture was hydrogenated for 48 hours at normal pressure and temperarure. The mixture was then filtered and the filtrate was concentrated in vaccuo. The residue was taken up in ethyl acetate and washed with sodium hydroxide (1M, aq.), water and brine. The solution was concentrated in vaccuo, and the residue was purified on silica (dichloromethane-methanol-ammonium hydroxide, 25% in water, 90:10:1), to give 0.60 g (96%) of the sub-title compound.

$^1$H NMR (400 MHz, CDCl$_3$): 8.02 (1H, s); 7.81 (1H, dd); 7.32 (1H, dd); 7.02 (1H, dt); 4.80–4.70 (1H, m); 3.93 (3H, s); 3.51 (2H, s); 2.93–2.85 (2H, m); 2.58–2.48 (1H, m); 2.38–2.25 (2H, m); 2.09–1.93 (2H, m); 1.75–1.62 (2H, m).

d) 1-[((1S,3R)-3-(tert-Butyloxycarbonylamino-methyl)-cyclopentyl]-5-fluoro-indole-3-carboxylic acid methyl ester In a flask was dissolved the compound obtained in c) (0.70 g, 2.4 mmol) in THF (50 mL). and the solution was cooled on an ice-bath. Di-tert-butyldicarbonate (0.80 g, 3.67 mmol) was added and the flask was sealed and stirred for 3 hours. The solvent was removed in vaccuo, and the residue was purified on silica (toluene-ethyl acetate, 10:1), giving 0.9 g (100%) of the sub-title compound as a colorless oil.

$^1$H NMR (400 MHz, CDCl$_3$): 7.97 (1H, s); 7.83 (1H, dd); 7.32 (1H, dd); 7.03 (1H, dt); 4.74 (1H, p); 3.92 (3H, s); 3.26–3.16 (2H, m); 2.53–2.44 (1H, m); 2.38–2.26 (2H, m); 2.07–1.96 (2H, m); 1.69–1.58 (2H, m); 1.46 (9H, s).

e) 1-[(1S,3R)-3-(tert-Butyloxycarbonylamino-methyl)-cyclopentyl-]5-fluoro-indole-3-carbonyl azide The compound was prepared according to the method described in Example 11c) and Example 11d), starting from the compound obtained in d).

$^1$H NMR (400 MHz, CDCl$_3$): 7.98 (1H, s); 7.91 (1H, dd); 7.34 (1H, dd); 7.05 (1H, dt); 4.75 (1H, p); 3.24 (2H, d); 2.54–2.46 (1H, m); 2.41–2.27 (2H, m); 2.06–1.95 (2H, m); 1.72–1.60 (2H, m).

In a flask was dissolved the compound obtained in e) (0.081 g, 0.20 mmol) in toluene (5 mL). The solution was heated under nitrogen to 110° C. for 90 minutes and was then allowed to cool. This cool solution was added to a suspension of the product of Example 11e) (0.047 g, 0.23 mmole) in THF (20 mL). The mixture was stirred for 1 hour and concentrated in vaccuo.

To the residue was added xylene (8 mL), triethylamine (0.140 mL, 5 equiv.) and trifluoromethanesulfonic acid trimethylsilyl ester (0.180 mL, 5 equiv.) The flask was sealed and immersed in a preheated oil bath (130° C.) for 1 hour. The emulsion was then allowed to cool, and methanol (5 mL) was added. The mixture was stirred for 15 minutes and evaporated. The residue was purified on silica (dichloromethane-methanol-ammonium hydroxide, 25% in water, 90:10:1) giving 0.090 g of a partially pure compound. This was further purified on preparative HPLC (containing trifluoroacetic acid), giving 0.055 g (48%) of the title compound as a pale solid after lyophilization.

$^1$H NMR (400 MHz, DMSO-d$_6$): 11.93 (1H, s); 7.96 (1H, s); 7.79–7.70 (5H, m); 7.48 (1H, dd, J 9.3 Hz and 4.6 Hz); 7.10 (2H, tt, J 8.9 Hz and 2.2 Hz); 7.03 (1H, dd, J 9.3 Hz 2.2 Hz); 6.63 (1H, s); 5.08 (1H, p, J 8.8 Hz); 3.57 (3H, s); 2.91 (2H, p, J 2.9 Hz); 2.48–2.40 (2H, m): 2.35–2.20 (2H, m); 1.97–1.86 (2H, m); 1.70–1.55 (2H, m).

APCI-MS: m/z 463.2 [MH+].

EXAMPLE 39

4-[1-((1S,3R)-3-Dimethylaminomethyl-cyclopentyl)-5-fluoro-indol-3-yl]-5-(5-fluoro-1-methyl-indol-3-yl)-2,4-dihydro-[1,2,4]triazol-3-one trifluoroacetate In a flask was added the compound obtained in Example 38 (0.08 g, 0.12 mmol) and sodium triacetoxyborohydride (0.94 g, 4.4 mmol). A mixture of methanol (9 mL), acetic acid (1 mL) and formaldehyde (1.2 mL, 37% in water) was added. The flask was sealed and the content was stirred for 3 hours. The volatiles were removed in vaccuo, and the residue was purified on silica (dichloromethane-methanol-ammonium hydroxide, 25% in water, 90:10:1). The pure fractions were collected and evaporated. The residue was dissolved in a solution of sodium methoxide (10 mL, 0.1 M in methanol), and was left to stand for 1 hour. Ammonia (2 mL, 25% in water) was added and the solution was evaporated to dryness. The residue was purified on preparative HPLC (containing trifluoroacetic acid), giving 0.055 g (76%) of the title compound after lyophilization.

$^1$H NMR (400 MHz, DMSO-d$_6$): 11.93 (1H, s); 9.22 (1H, bs); 7.95 (1H, s); 7.77–7.71 (2H, m); 7.48 (1H, dd, J 8.6 Hz and 4.5 Hz); 7.11 (2H, qt, J 9.2 Hz and 2.6 Hz); 7.04 (1H, dd, J 9.2 Hz and 2.6 Hz); 6.64 (1H, s); 5.07 (1H, p, J 7.8 Hz); 3.57 (3H, s); 3.18 (2H, t, J 6.2 Hz); 2.84–2.78 (6H, m); 2.55–2.41 (2H, m); 2.30–2.18 (1H, m); 2.03–1.87 (2H, m); 1.72–1.54 (2H, m).

APCI-MS: m/z 491.2 [MH+].

EXAMPLE 40

4-[1-((1S,3R)-3-Dimethylaminomethyl-cyclopentyl)-5-fluoro-indol-3-yl]-5-(5-fluoro-1-methyl-indol-3-yl)-2-hydroxymethyl-2,4-dihydro-[1,2,4]triazol-3-one trifluoroacetate The title compound was prepared according to Example 39, excluding the treatment with sodium methoxide in methanol.

$^1$H NMR (400 MHz, DMSO-d$_6$): 9.14 (1H, bs); 7.99 (1H, s) 7.87 (1H, dd, J 10.1 Hz and 2.5 Hz); 7.78–7.71 (2H, m); 7.48 (1H, dd, J 9.0 Hz and 4.5 Hz); 7.13 (2H, m); 7.04 (1H, dd, J 9.3 Hz and 2.3 Hz); 6.64 (1H, s); 5.20 (2H, s); 5.08 (1H, p, J 8.1 Hz); 3.58 (3H, s); 3.18 (2H, t, J 6.0 Hz); 2.80 (6H, m); 2.54–2.40 (2H, m); 2.34–2.20 (1H, m); 2.02–1.88 (2H, m); 1.72–1.52 (2H, m).

APCI-MS: m/z 521.2 and 491.2 [MH+].

EXAMPLE 41

5-{5-Fluoro-3-[3-(5-fluoro-1-methyl-indol-3-yl)-5-oxo-1,5-dihydro-[1,2,4]triazol-4-yl]-indol-1-yl}-pentanamidine trifluoroacetate In a vial was dissolved the compound obtained in Example 19 (0.080 g, 0.16 mmol) in DMF (2 mL) and sodium cyanide (0.050 g, 1.02 mmol) was added. The vial was sealed and heated (50° C.) with stirring for 2 hours. The mixture was partitioned between ethyl acetate and water. The organic phase was washed with water, brine and evaporated to give the crude nitrile.

The nitrile was dissolved in a freshly prepared solution of hydrochloric acid in ethanol (saturated) in a flask. The flask was sealed and stirred over night. The volatiles were removed in vaccuo, to give a semi-crystalline crude iminoester.

The crude iminoester was dissolved in a solution of ammonia in methanol. The solution was stirred for 3 hours and the reaction was monitored on HPLC. The mixture was evaporated and the residue was purified on preparative HPLC (containing trifluoroacetic acid) giving 0.050 g (54%) of the title compound as a white solid.

$^1$H NMR (400 MHz, DMSO-d$_6$): 11.94 (1H, s); 8.86 (2H, bs); 8.49 (2H, bs); 7.82 (1H, s); 7.73 (1H, dd, J 10.2 Hz and 2.6 Hz); 7.68 (1H, dd, J 9.0 Hz and 4.3 Hz); 7.47 (1H, dd, J 8.8 Hz and 4.6 Hz); 7.11 (2H, tt, J 9.2 Hz and 2.6 Hz); 7.03 (1H, dd, J 9.4 Hz and 2.4 Hz); 6.71 (1H, s); 4.30 (2H, t, J 7.2 Hz); 3.57 (3H, s); 2.38 (2H, t, J 7.6 Hz); 1.82 (2H, p, J 7.5 Hz); 1.61 (2H, p, J 7.5 Hz).

APCI-MS: m/z 464.2 [MH+].

EXAMPLE 42

5-{5-Fluoro-3-[3-(5-fluoro-1-methyl-indol-3-yl)-5-oxo-1,5-dihydro-[1,2,4]triazol-4yl]-indol-1-yl}-butanamidine trifluoroacetate The title compound was prepared according to the method described in Example 41, starting from the compound obtained in Example 18.

$^1$H NMR (400 MHz, DMSO-d$_6$): 11.94 (1H, s); 8.93 (2H, bs); 8.61 (2H, bs); 7.81 (1H, s); 7.76 (1H, dd, J 10. 1 Hz and 2.6 Hz); 7.68 (1H, dd, J 9.0 Hz and 4.3 Hz); 7.48 (1H, dd, J 8.9 Hz and 4.6 Hz); 7.16–7.02 (3H, m); 6.75 (1H, s); 4.31 (2H, t, J 7.0 Hz); 3.57 (3H, s); 2.46–2.40 (2H, m); 2.16 (2H, p, J 7.7 Hz).

APCI-MS m/z: 450.2 [MH+].

EXAMPLE 43

5-[1-(3-Aminopropyl)-indol-3-yl]-4-(1-methyl-indol-3-yl)-2,4-dihydro-[1,2,4]triazol-3-one trifluoroacetate a) 1-(3-Azidopropyl)-indole-3-carboxylic acid hydrazide In a flask was dissolved the compound obtained in Example 11c) (0.354 g, 1.45 mmol) and N-hydroxysuccinimide (0.20 g, 1.74 mmol) and dimethylaminopyridine (0.02 g, 0.16 mmole) in dry dichloromethane (10 mL). To the stirred solution was added dicyclohexyl-carbodiimide (0.355 g, 1.70 mmole). After 1 min, a precipitate was obtained, but the reaction was allowed to proceed over night. Hydrazinium hydroxide (0.30 g, 6.0 mmol) was added and the reaction was stirred for another 30 min. The solvent was evaporated in vaccuo, and the residue was purified on silica (dichloromethane-methanol, 99:1 to 96:4, gradient), giving 0.34 g (91%) of the sub-title compound.

APCI-MS m/z: 259.0 [MH+].

b) 1-[1-(3-Azidopropyl)-indol-3-carbonyl]-4-(1-methyl-indol-3-yl)semicarbazide

In a flask was added 1-methyl-indole-3-carbonylazide (0.038 g, 0.19 mmol, prepared according to Example 5b) in toluene (5 mL). The solution was heated to 110° C. during 1 h and was then allowed to cool. The cool solution was added to a solution of the compound obtained in a) (0.05 g, 0.19 mmol) in 10 mL of THF. After a few minutes a precipitation was formed. The mixture was stirred for another 30 min and the precipitate collected by centrifugal sedimentation. The supernatant was discarded and the solid was dried in vaccuo giving 0.064 g (75%) of the sub-title compound.

$^1$H NMR (400 MHz, DMSO-$d_6$): 9.74 (1H, bs); 8.57 (1H, bs); 8.16–8.11 (2H, m); 7.91 (1H, bs); 7.55 (2H, t, J 7.8 Hz); 7.40 (1H, s); 7.36 (1H, d, J 8.9 Hz); 7.22 (1H, t, J 7.7 Hz); 7.18–7.10 (2H, m); 7.00 (1H, t, J 7.5 Hz); 4.29 (2H, t, J 6.8 Hz); 3.71 (3H, s); 3.37 (2H, t, J 6.7 Hz); 2.03 (2H, p, J 6.8 Hz).

APCI-MS m/z: 431.0 [MH+].

c) 5-[1-(3-Azidopropyl)-indol-3-yl]-4-(1-methyl-indol-3-yl)-2,4-dihydro-[1,2,4]triazol-3-one In a flask was added the compound obtained in b) (0.062 g, 0.14 mmol) and 3 mL of DMF. To this solution was added subsequently triethyl amine (0.073 g, 0.72 mmol) and trifluoromethanesulfonic acid trimethylsilyl ester (0.16 g, 0.72 mmol). The flask was sealed and was immersed in a preheated oil bath (130° C.) and stirred for 1 h. The mixture was allowed to cool and ethyl acetate (15 mL) and water (15 mL) was added. The heterogeneous mixture was stirred for 15 min. The phases were allowed to separate and the aqueous phase was extracted with ethyl acetate (15 mL). The combined organic phases were washed twice with water, once with brine and finally evaporated. The residue was purified on silica (dichloromethane to dichloromethane-methanol, 98:2, gradient), giving 0.043 g (72%) of the sub-title compound.

$^1$H NMR (400 MHz, DMSO-$d_6$): 11.89 (1H, s); 8.13 (1H, d, J 7.8 Hz); 7.70 (1H, s); 7.59 (1H, d, J 8.4 Hz); 7.47 (1H, d, J 8.1 Hz); 7.23 (2H, t, J 9.2 Hz); 7.16 (1H, t, J 7.5 Hz); 7.11 (1H, d, J 7.5 Hz); 7.00 (1H, t, J 7.5 Hz); 6.59 (1H, s); 3.96 (2H, t, J 6.5 Hz); 3.90 (3H, s): 2.78 (2H, t, J 6.8 Hz); 1.61 (2H, p, J 6.7 Hz).

APCI-MS m/z: 413.0 [MH+].

Compound c) (0.042 g, 0.10 mmol) was dissolved in ethanol (5 mL, 99.5%) and acetic acid (5 mL). Palladium on charcoal (0.010 g, 10% Pd on C) was added and the compound was hydrogenated during 3 hours at normal pressure and temperature. The catalyst was removed by filtration through Celite® and the filtrate was concentrated in vaccuo. The residue was purified on silica (dichloromethane-methanol-ammonium hydroxide, 25% in water, 90:10:2). The purified product was then dissolved in methanol and water. Trifluoroacetic acid was added, the methanol was evaporated and the residual water solution was lyophilized to give 0.025 g (50%) of the title compound as a white solid.

$^1$H NMR (400 MHz, DMSO-$d_6$): 11.90 (1H, s); 8.09 (1H, d, J 8.4 Hz); 7.66 (1H, s); 7.57 (1H, d, J 9.5 Hz); 7.60–7.52 (3H, bs); 7.49 (1H, d, J 8.3); 7.22 (1H, t, J 9.5 Hz); 7.14 (1H, t, J 7.9 Hz); 7.00 (1H, t, J 7.9 Hz); 6.68 (1H, s); 3.99 (2H, t, J 7.0 Hz); 3.87 (3H, s); 2.43 (2H, m); 1.71 (2H, p, J 7.0 Hz).

APCI-MS m/z: 387.2 [MH+].

EXAMPLE 44

4-[1-(3-Amnopropyl)-5-methyl-indol-3-yl]-5-(1-methyl-indol-3-yl)-2,4-dihydro-[1,2,4]triazol-3-one trifluoroacetate a) 5-methyl-indole-3-carboxylic acid methyl ester The sub-title compound was prepared in a manner analogous to Example 1a) from 5-methyl-1H-indole.

$^1$H NMR (400 MHz, DMSO-$d_6$): δ11.80 (1H, bs); 8.00 (1H, s); 7.79 (1H, t, J 0.8 Hz); 7.35 (1H, d, J 8.4 Hz); 7.02 (1H, dd, J 8.4 and 1.5 Hz); 3.79 (3H, s); 2.40 (3H, s).

b) 1-(3-tert-Butoxycarbonylamino-propyl)-5-methyl-1H-indole-3-carboxylic acid methyl ester A mixture of sub-title compound a) (217 mg, 1.2 mmol), 3-t-butoxycarbonylamino-propyl bromide (656 mg, 2.8 mmol) and potassium carbonate (380 mg, 2.8 mmol) in dry DMF (7 mL) was stirred at room temperature for 16 h then partitioned between ethyl acetate and water. The organic phase was washed with water, saturated aqueous sodium chloride and water, dried and concentrated. The residue was subjected to silica gel flash chromatography (heptane-ethyl acetate, 5:2) to give the sub-title compound (280 mg, 70%).

$^1$H NMR (400 MHz, CDCl$_3$): δ7.98 (1H, s); 7,79 (1H, s); 7.24 (1H, d, J 8.4 Hz); 7.12 (1H, dd, J 8.4 and 1.3 Hz); 4.54 (1H, bs); 4.18 (2H, t, J 7.0 Hz); 3.91 (3H, s); 3.13 (2H, m); 2.50 (3H, s); 2.06 (2H, p, J 6.8 Hz); 1.45 (9H, s).

c) [3-(3-Azidocarbonyl-5-methyl-indol-1-yl)-propyl]-carbamic acid tert-butyl ester The sub-title compound was prepared in a manner analogous to Example 1c), starting from b).

$^1$H NMR (400 MHz, CDCl$_3$): δ8.05 (1H, s); 7.82 (1H, s); 7.25 (1H, d, J 8.4 Hz); 7.14 (1H, dd, J 8.4 and 1.4 Hz); 4.62 (1H, bs); 4.18 (2H, t, J 7.0 Hz); 3.15 (2H, m); 2.50 (3H, s); 2.26 (2H, p, J 6.8 Hz); 1.46 (9H, s).

d) [3-(3-Isocyanato-5-methyl-indol-1-yl)-propyl]-carbamic acid tert-butyl ester

A solution of c) (138 mg, 0.4 mmol) in toluene (8 mL) was heated at reflux for 3 h and then concentrated to give the sub-title compound (120 mg, 78%).

$^1$H NMR (400 MHz, CDCl$_3$): δ7.36 (1H, s); 7.19 (1H, d, J 8.2 Hz); 7.08 (1H, dd, J 8.6 and 1.0 Hz); 6.92 (1H, s); 4.53 (1H, m); 4.07 (2H, t, J 6.9 Hz); 3.09 (2H, m); 2.47 (3H, s); 1.97 (2H, p, J 6.8 Hz); 1.44 (9H, s).

e) 4-[1-(3-tert-Butoxycarbonylamino-propyl)-5-methyl-indol-3-yl]1-1(1-methyl-indol-3-carbonyl)semicarbazide A solution of 1-methyl-1H-indole-3-carboxylic acid hydrazide (105 mg, 0.6 mmol) in dry DMF (1.5 mL), was added to a solution of compound d) (120 mg, 0.4 mmol) in dry dioxane (8 mL). The mixture was stirred at room temperature for 16 h, then partitioned between ethyl acetate and water. The organic phase was washed three times with, dried and concentrated. The residue was subjected to silica gel flash chromatography (dichloromethane-methanol, 25:1). The fractions containing the sub-title compound were combined, concentrated, dissolved in chloroform and methanol and diethyl ether was added to precipitate the sub-title compound (140 mg, 75%).

$^1$H NMR (400 MHz, DMSO-$d_6$): δ9.73 (1H, bs); 8.52 (1H, bs); 8.14 (1H, d, J 7.8 Hz); 8.10 (1H, s); 7.88 (1H, bs); 7.52(1H, d, J 8.2 Hz); 7.42 (1H, s); 7.33 (1H, s); 7.29 (1H, d, J 8.2 Hz); 7,24 (1H, t, J 6.8 Hz); 7.17 (1H, t, J 7.2 Hz); 6.95 (1H, d, J 8.8 Hz); 6.93 (1H, m); 4.08 (2H, t, J 6.8 Hz): 3.86 (3H, s); 2.89 (2H, m); 2.38 (3H, s); 1.80 (2H, p); 1.36 (9H, s).

APCI-MS m/z: 419 [MH+]-t-Boc.

A mixture of compound e) (98 mg, 0.19 mmol), triethylamine (91 mg, 0.9 mmol) and trimethylsilyl trifluoromethanesulfonate (200 mg, 0.9 mmol) and DMF (3 mL) in a sealed tube was heated at 130° C. for 3 h. The mixture was concentrated and the oily residue was treated with 2N sodium hydroxide (2 mL) and stirred for 1 h. at 80–100° C. The crude product was purified by preparative HPLC to afford the title compound as the trifluoroacetic acid salt (70 mg, 72%).

$^1$H NMR (400 MHz, DMSO-d$_6$): δ11.88 (1H, s); 8.12 (1H, d, J 7.8 Hz); 7.79 (3H, bs); 7.68 (1H, s); 7.58 (1H, d, J 8.4 Hz); 7.44 (1H, d, J 8.2 Hz); 7.24 (1H, m); 7.16 (1H, m); 7.09 (1H, d, J 8.4 Hz); 7.03 (1H, s); 6.58 (1H, s); 4.34 (2H, t, J 6.8 Hz); 3.54 (3H, s); 2.80 (2H, m); 2.31 (3H, s); 2.08 (2H, p, J 6.8 Hz).

APCI-MS m/z: 401 [MH+].

EXAMPLE 45

4-[1-(3-Aminopropyl)-5-fluoro-indol-3-yl]-5-(1H-pyrrolo[2,3-b]pyridin-3-yl)-2,4-dihydro-[1,2,4]triazol-3-one hydrochloride

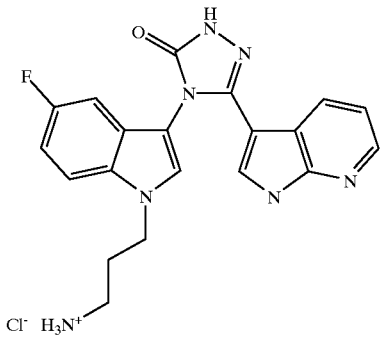

a) 2,2,2-Trichloro-1-(1H-1pyrrolo[2,3-b]pyridin-3-yl)-ethanone

A mixture of 7-azaindole (2.03 g, 17.2 mmol) and trichloroacetyl chloride (4.06 g, 20.6 mmol) was heated at 110 C. in a sealed tube for 30 min., then cooled to r.t. The crude product was dissolved in minimum amount of ethanol and chloroform was added to induce crystallization. The crystalline material was filtered (2.21 g) and recrystallized from ethanol to afford the pure sub-title compound (1.15 g, 25%).

$^1$H NMR (400 MHz, DMSO-d$_6$): δ13.16 (1H, bs); 8,68 (1H, s); 8.51 (1H, dd; J 7.8 and 1.5 Hz); 8.42 (1H, dd, J 4.6 and 1.5 Hz); 7.38 (1H, dd, J 7.8 and 4.6 Hz).

APCI-MS m/z: 263 [MH+]; and 265 [MH 2+].

b) 1H-Pyrrolo[2,3-b]pyridine-3-carboxylic acid hydrazide

A mixture of compound a) (1.04 g, 3.9 mmol) and hydazine hydrate (0.30 g, 5.9 mmol) in dry THF (30 mL) was heated at reflux for 1.5 h. The solid product was filtered and washed several times with THF and then with diethyl ether to afford the sub-title compound (0.56 g, 81%).

$^1$H NMR (400 MHz, DMSO-d$_6$): δ12.05 (1H, bs); 9.26 (1H, s); 8.42 (1H, bd, J 7.8 Hz); 8.26 (1H, bd, J 4.6 Hz); 8.08 (1H, s); 7.16 (1H, ddd, J 7.8 and 4.7 Hz); 4.33 (2H, s).

APCI-MS m/z: 177 [MH+].

c) 3-(3-Azidocarbonyl-5-fluoro-indol-1-yl)-propyl]-carbamic acid tert-butyl ester The sub-title compound was prepared in a manner analogous to Example 44c) starting from from 5-fluoro-indole.

$^1$H NMR (400 MHz, DMSO-d$_6$) δ8.37 (1H, s); 7.73 (1H, dd, J 9.7 and 2.5 Hz); 7.69 (1H, dd, J 9.1 and 4.5 Hz); 7.18 (1H, m); 6.97 (1H, m); 4.29 (2H, m); 2.90 (2H, m); 1.88 (2H, m); 1.37 (9H, s).

d) [3-(5-Fluoro-3-isocyanato-indol-1-yl)-propyl]-carbamic acid tert-butyl ester

The sub-title compound was prepared as described in the synthesis of compound 44d) starting from c).

$^1$H NMR (400 MHz, DMSO-d$_6$): δ7.58 (1H, s); 7.53 (1H, dd, J 9.1 and 4.3 Hz); 7.25 (1H, bd); 7.06 (1H, m); 6.91 (1H, m); 4.12 (2H, m); 2.86 (2H, m); 1.80 (2H, m); 1.35 (9H, s).

e) 4-[1-(3-tert-butoxycarbonylamino-propyl)-5-fluoro-indol-3-yl]-1-(7-azaindol-3-carbonyl)semicarbazide A suspension of sub-title compound b) (98 mg, 0.56 mmol) in dry DMF (5 mL) was added to a solution of compound d) (233 mg, 0.56 mmol) in dry dioxane (5 mL) and the mixture was stirred at r.t. for 1.5 h, then partitioned between ethtyl acetate and water. The organic phase was washed twice with water, then concentrated. The solid residue was triturated with toluene and filtered to give the sub-title compound (200 mg, 70%).

$^1$H NMR (400 MHz, DMSO-d$_6$): δ12.19 (1H, bs); 9.86 (1H, bs); 8.60 (1H, bs); 8.44 (1H, d, J 7.8 Hz); 8.30 (1H, d, J 4.4 Hz); 8.26 (1H, s); 7.94 (1H, bs); 7.54 (1H, s); 7.44 (1H, dd, J 7.8 and 4.4 Hz); 7.30 (1H, m); 7.20 (1H, m); 6.92–7.00 (2H, m); 4.12 (2H, t, J 6.4 Hz); 2.90 (2H, m); 1.82 (2H, m,); 1.37 (s, 9H).

A mixture of sub-title compound e) (99 mg, 0.19 mmol), trimethylsilyl trifluoromethanesulfonate (345 mg, 1.55 mmol) and triethylamine (157 mg, 1.55 mmol) in dry DMF (5 mL) in a sealed tube was heated at 130° C. for 15 min., cooled to r.t. and partitioned between ethyl acetate and water. The aqueous phase was made basic (pH 10) and extracted with ethyl acetate, then with a mixture of dichloromethane and methanol (3:1 by volume). The organic extracts were combined and concentrated. The residue was triturated with ethyl ether and the solid was collected by filtration and subjected to silica gel flash chromatography (dichloromethane-methanol-ammonium hydroxide, 150:15:2 then 150:20:2). Fractions containing the free amine were combined and concentrated. The residue was dissolved in 0.2 N hydrochloric acid (20 mL) and freeze-dried to afford the title compound (28 mg, 34.6%).

$^1$H NMR (400 MHz, DMSO-d$_6$): δ11.98 (1H, s); 11.82 (1H, bs); 8.40 (1H,dd, J 8.0 and 1.6 Hz); 8.30 (1H,dd, J 4.8 and 1.5 Hz); 7.87 (4H, m); 7.74 (1H, dd, J 9.0 and 4.3 Hz); 7.2 (1H, dd, J 8.0 and 4.8 Hz); 7.14 (1H, dt, J 9.2 and 1.5 Hz); 7.07 (1H, dd, J 9.4 and 2.4 Hz); 6.66 (1H, d, J 2.8 Hz); 4.39 (2H, t, J 6.8 Hz), 2.80 (2H, m); 2.08 (2H, m).

APCI-MS m/z: 392 [MH+].

EXAMPLE 46

4-[1-(3-Aminopropyl)-5-fluoroindol-3-yl]-5-(4-fluoro-1-methyl-indol-3-yl)-2,4-dihydro-[1,2,4]triazol-3-one trifluoroacetate The title compound was prepared in a manner analogous to Example 45 from 4-fluoro-1-methyl-1H-indole-3-carboxylic acid hydrazide and 45d).

$^1$H-NMR (400 MHz, DMSO-d$_6$): δ11.97 (1H, s); 7.65 (2H, bs); 7.58 (1H, s); 7.52 (1H, s); 7.52 (1H, m); 7.25 (1H, d, J 8.2 Hz); 7.10 (1H, m); 7.02 (1H, dd, J 9.2 and 2.4 Hz); 6.98 (1H, dd, J 5.7 and 2.4 Hz); 6.96 (1H, dd, J 9.4 and 2.4 Hz); 6.78 (1H, dd, J 11.2 and 7.8 Hz); 4.20 (2H, t, J 6.6 Hz); 3.72 (3H, s); 2.64 (2H, m); 1.91 (2H, m).

APCI-MS m/z: 423 [MH+].

EXAMPLE 47

4-[1-(3-Amninopropyl)-indol-3-y]-5-(1-methyl-indol-3-yl)-2,4-dihydro-[1,2,4]triazol-3-one trifluoroacetate The title compound was prepared in a manner analogous to Example 11 from 1-methyl-1H-indole-3-carboxylic acid hydrazide and 11d).

¹H NMR (400 MHz, DMSO-d$_6$): δ11.92 (1H, s); 8.12 (1H, d); 7.79 (3H, bs); 7.77 (1H, s); 7.71 (1H, d); 7.45 (1H, d); 7.29 (1H, dd); 7.25 (1H, d); 7.25 (1H, dd); 7.18 (1H, dd); 7.09 (1H, dd); 6.62 (1H, s); 4.40 (2H, t); 3.56 (3H, s); 2.88–2.78 (2H, m); 2.12 (2H, p).

APCI-MS m/z: 387 [MH+].

EXAMPLE 48

4-[1-(2-Aminoethyl)-5-fluoro-indol-3-yl]-5-(5-fluoro-1-methyl-indol-3-yl)-2,4-dihydro-[1,2,4]triazol-3-one trifluoroacetate The title compound was prepared by the method described in Example 11.

¹H NMR (400 MHz, DMSO-d$_6$): δ11.96 (1H, s); 8.03 (3H, bs); 7.72 (1H, s); 7.81 (1H, dd); 7.73 (1H, dd); 7.50 (1H, dd); 7.19 (1H, dt); 7.13 (1H, dt); 7.09 (1H, dd); 6.91 (1H, s); 4.50 (2H, t); 3.63 (3H, s); 3.40–3.30 (2H, m).

APCI-MS m/z: 409 [MH+].

EXAMPLE 49

4-[1-(4-Aminobutyl)-5-fluoro-indol-3-yl]-5-(5-fluoro-1-methyl-indol-3-yl)-2,4-dihydro-[1,2,4]triazol-3-one trifluoroacetate The title compound was prepared by the method described in Example 11.

¹H NMR (400 MHz, DMSO-d$_6$): δ11.96 (1H, s); 7.84 (1H, s); 7.78 (1H, dd); 7.75 (3H, bs); 7.72 (1H, dd); 7.50 (1H, dd); 7.13 (2H, dt); 7.05 (1H, dd); 6.71 (1H, s); 4.32 (2H, t); 3.59 (3H, s); 2.88–2.83 (2H, m); 1.85–1.93 (2H, m); 1.61–1.54 (2H, m).

APCI-MS m/z: 437 [MH+].

EXAMPLE 50

4-[1-(5-Aminopentyl)-5-fluoro-indol-3-yl]-5-(5-fluoro-1-methyl-indol-3-yl)-2,4-dihydro-[1,2,4]triazol-3-one trifluoroacetate The title compound was prepared by the method described in Example 11.

¹H NMR (400 MHz, DMSO-d$_6$): δ11.96 (1H, s); 7.82 (1H, s); 7.74 (1H, dd); 7.70 (3H, bs); 7.70 (1H, dd); 7.49 (1H, dd); 7.12 (2H, dt); 7.05 (1H, dd); 6.74 (1H, s); 4.28 (2H, t); 3.59 (3H, s); 2.79–2.74 (2H, m); 1.87–1.79 (2H, m); 1.60–1.53 (2H, m); 1.35–1.28 (2H, m).

APCI-MS m/z: 451 [MH+].

EXAMPLE 51

5-(5-Fluoro-1-methyl-indol-3-yl)-4-[5-fluoro-1-(3-morpholin-4-yl-propyl)-indol-3-yl]-2,4-dihydro-[1,2,4]-triazol-3-one trifluoroacetate The title compound was prepared by the method described in Example 26.

¹H NMR (400 MHz, DMSO-d$_6$): δ 11.95 (1H, s); 9.96 (1H, bs); 7.86 (1H, s); 7.77 (1H, dd); 7.74 (1H, dd); 7.50 (1H, dd); 7.16 (2H, dt); 7.13 (1H, dt); 7.07 (1H, dd); 6.78 (1H, s); 4.38 (2H, t); 3.99 (2H, d); 3.67 (2H, t); 3.61 (3H, s); 3.45 (2H, d); 3.24–3.14 (2H m); 3.14–3.00 (2H, m); 2.31–2.18 (2H, m).

APCI-MS m/z: 493 [MH+].

EXAMPLE 52

5-(5-Fluoro-1-methyl-indol-3-yl)-4-{5-fluoro-1-[3-(4-methyl-piperazin-1-yl)-propyl]-indol-3-yl}-2,4-dihydro-[1,2,4]triazol-3-one bistrifluoroacetate The title compound was prepared in a manner anologous to Example 26 starting from the product of Example 18 and 1-methylpiperazine.

¹H NMR (400 MHz, DMSO-d$_6$): δ11.95 (1H, s); 7.83 (1H, s); 7.77–7.73 (2H, m); 7.49 (1H, dd); 7.16–7.10 (2H, m); 7.05 (1H, dd); 6.74 (1H, s); 4.36 (2H, t); 3.60 (3H, s); 2.80 (3H,s); 2–5 ppm (12H, broad signals).

APCI-MS m/z: 506 [MH+].

EXAMPLE 53

N'-(3-{5-Chloro-3-[3-(5-chloro-1-methyl-indol-3-yl)-5-oxo-1,5-dihydro-4H-1,2,4-triazol-4-yl]-indol-1-yl}propyl)-N,N-dimethylimidoformamiide trifluoroacetate (compound A) and 3-{5-Chloro-3-[3-(5-chloro-1-methyl-indol-3-yl)-5-oxo-1,5-dihydro-4H-1,2,4-triazol-4-yl]-indol-1-yl}propylformamide (compound B)

a) tert-Butyl 3-{5-chloro-3-[({2-[(5-chloro-1-methyl-indol-3-yl)-carbonyl]hydrazino}carbonyl)amino]-indol-1-yl}propylcarbamate The sub-title compound was prepared as described in Example 11 f), starting from [3-(3-Azidocarbonyl-5-chloro-indol-1-yl)-propyl]-carbamic acid tert-butyl ester and 5-chloro-1-methyl-indole-3-carbohydrazide which were prepared in analogy to the synthesis of Example 44 c) and Example 11 e) respectively.

¹H NMR (300 MHz, acetone-d$_6$): δ9.36 (1H, bs); 8.33 (1H, bs); 8.24 (1H, d); 8.09 (1H, s); 7.64 (1H, bs); 7.62 (1H, d); 7.59 (1H, s); 7.40 (1H, d); 7.37 (1H, d); 7.18 (1H, dd); 7.09 (1H, dd); 4.20 (2H, t); 3.84 (3H, s); 3.11–3.06 (2H, m); 1.98 (2H, p); 1.38 (9H, s).

APCI-MS m/z: 517 [MH$^+$-$^t$Bu] and 473 [MH$^+$-Boc]

A mixture consisting of compound a) (180 mg, 0.34 mmol), trimethylsilyltriflate (307 μL, 1.7 mmol), triethylamine (236 μL, 1.7 mmol) and dry DMF (3 mL) was heated at 130° C. for 1 h. The crude material obtained after evaporation consisted of two compounds. The two compounds were separated by RP-HPLC using acetonitrile/water containing 0.1% TFA as the mobile phase and the appropriate fractions were lyophilised to give title compound A (118 mg, 55%) as a crystallized oil and title compound B (45 mg, 27%) as a solid.

Title compound A:

¹H NMR (300 MHz, DMSO-d$_6$): δ12.01 (1H, s); 9.02 (1H, dt); 8.08 (1H, d); 8.03 (1H, d); 7.87 (1H, s); 7.75 (1H, d); 7.53 (1H, d); 7.36 (1H, d); 7.30 (2H, dt); 6.77 (1H, s); 4.36 (2H, t); 3.61 (3H, s); 3.38–3.30 (2H, m); 3.14 (3H, s); 2.97 (3H, s); 2.12 (2H, p).

APCI-MS m/z: 510 and 512 [MH$^+$]

Title compound B:

¹H NMR (300 MHz, DMSO-d$_6$): δ11.98 (1H, s); 8.14 (1H, bt); 8.10 (1H, d); 8.05 (1H, s); 7.85 (1H, s); 7.72 (1H, d); 7.51 (1H, d); 7.32 (1H, d); 7.27 (2H, dd); 6.75 (1H, s); 4.31 (2H, t); 3.60 (3H, s); 3.13–3.08 (2H, m); 1.98 (2H, p).

APCI-MS m/z: 483 and 485 [MH$^+$]

EXAMPLE 54

N'-(3-{5-Fluoro-3-[3-(4-fluoro-1-methyl-indol-3-yl)-5-oxo-1,5-dihydro-4H-1,2,4-triazol-4-yl]-indol-1-yl}propyl)-N,N-dimethylimidoformamnide trifluoroacetate (compound A) and 3-{5-Fluoro-3-[3-(4-fluoro-1-methyl-indol-3-yl)-5-oxo-1,5-dihydro-4H-1,2,4-triazol-4-yl]-indol-1-yl}propylformamide (compound B)

Compound A and compound B were prepared analogously as for the compounds described in Example 53.

Compound A: APCI-MS: 478.2 [MH+]
Compound B: APCI-MS: 451.1 [MH+]

EXAMPLE 55

4-[1-(3-Aminopropyl)-5-chloro-indol-3-yl]-5-(5-chloro-1-methyl-indol-3-yl)-2,4-dihydro-[1,2,4]triazol-3-one trifluoroacetate Compound A from Example 53 was stirred in 1M sodium hydroxide (2 mL) at 100° C. for 2 hours. Trifluoroacetic acid was added and and the crude product was purified by HPLC to afford the title compound (56 mg, 98%).

$^1$H NMR (400 MHz, DMSO-d$_6$): δ11.99 (1H, s); 8.09 (1H, d); 7.84 (1H, s); 7.78 (3H, bs); 7.77 (1H, d); 7.53 (1H, d); 7.35 (1H, d); 7.31 (1H, dd); 7.28 (1H, dd); 6.72 (1H, s); 4.39 (2H, t); 3.61 (3H, s); 2.86–2.77 (2H, m); 2.09 (2H, p).

APCI-MS m/z: 455 and 457 [MH+].

EXAMPLE 56

4-[1-(3-Amninopropyl)-6-fluoro-indol-3-yl]-5-(6-fluoro-1-methyl-indol-3-yl)-2,4-dihydro-[1,2,4]triazol-3-one trifluoroacetate The title compound was prepared by the method described in Example 11.

$^1$H NMR (400 MHz, DMSO-d$_6$): δ11.98 (1H, s); 8.10 (1H, dd); 7.83 (3H, bs); 7.78 (1H, s); 7.64 (1H, dd); 7.36 (1H, dd); 7.26 (1H, dd); 7.04 (1H, dt); 6.95 (1H, dt); 6.63 (1H, s); 4.36 (2H, t); 3.53 (3H, s); 2.88–2.78 (2H, m); 2.11 (2H, p).

APCI-MS m/z: 423 [MH+].

EXAMPLE 57

4-[1-(3-Aminopropyl)-5-fluoro-indol-3-yl]-5-(9H-pyrido[3,4-b]indol-3-yl)-2,4-dihydro-[1,2,4]-triazol-3-one bistrifluoracetate a) 1,1-Dimethylethyl 3-[3-({[2-(9H-β-carbolin-3-ylcarbonyl)hydrazino]carbonyl}amino)-5-fluoro-1H-indol-1-yl]propylcarbamate Compound 45d) (108 mg, 0.30 mmol) in toluene (3 mL) was added to a solution of 9H-β-Carboline-3-carboxylic acid hydrazide (68 mg, 0.30 mmol, prepared using a process analogous to that described in the synthesis of compound 45b) in THF (15 mL). The mixture was stirred at room temperature over night and concentrated. The crude substance (153 mg, 91%) was used in the next step without further purification.

$^1$H NMR (400 MHz, DMSO-d$_6$): δ12.02 (1H, bs); 10.21 (1H, bs); 8.96 (1H, s); 8.91 (1H, s); 8.62 (1H, bs); 8.45 (1H, d); 8.13 (1H, bs); 7.69 (1H, d); 7.63 (1H, dt); 7.56 (1H, s); 7.46 (1H, dd); 7.36–7.31 (2H, m); 7.00 (1H, dt); 6.96 (1H, bs); 4.15 (2H, t); 2.95–2.90 (2H, m); 1.84 (2H, p); 1.39 (9H, s).

APCI-MS m/z: 560 [MH+].

b) (3-{3-[3-(9H-β-Carbolin-3-yl)-5-oxo-1,5-dihydro-[1,2,4]triazol-4-yl]-5-fluoro-indel-1-yl}-propyl)-carbamic acid tert-butyl ester A suspension of a) (75 mg, 0.135 mmol), N,O-bis(trimethylsilyl)trifluoroacetamide (360 μL, 1.35 mmol) and N,N-diisopropylethylamine (115 μL, 0.675 mmol) in dry xylene (3 mL) was stirred at 130° C. in a sealed vial over night. The mixture was evaporated to give the crude sub-title compound, which was used in the next step without further purification.

APCI-MS m/z: 542 [MH+].

The crude product from b) was dissolved in a mixture of trifluoroacetic acid (1 mL) and dichloromethane (4 mL). The solution was stirred for 1 hour and then concentrated in vacuo. The crude material was purified by HPLC and lyophilized to give the title compound (53 mg, 58%).

$^1$H NMR (400 MHz, DMSO-d$_6$): δ12.17 (1H, s); 11.78 (1H, s); 8.61 (2H, s); 8.30 (1H, d); 7.74 (3H, bs); 7.69 (1H, s); 7.56–7.64 (3H, m); 7.30 (1H, dt); 7.03 (1H, dt); 6.92 (1H, dd); 4.30 (2H, t); 2.74–2.81 (2H, m); 2.03 (2H, p).

APCI-MS m/z: 442 [MH+].

EXAMPLE 58

4-[1-(3-Aminopropyl)-5-fluoro-indol-3-yl]-5-naphthalen-1-yl-2,4-dihydro-[1,2,4]triazol-3-one trifluoroacetate The title compound was prepared in a manner anologous to Example 57 starting from 45d) and naphthalene-1-carboxylic acid hydrazide.

$^1$H NMR (400 MHz, DMSO-d$_6$): δ12.28 (1H, s); 8.11–8.08 (1H, m); 7.96 (1H, d); 7.93–7.90 (1H, m); 7.69 (3H, bs); 7.62 (1H, dd); 7.59 (1H, s); 7.55–7.43 (4H, m); 7.08 (1H, dd); 6.98 (1H, dt); 4.15 (2H, t); 2.62–2.54 (2H, m); 1.87 (2H, p).

APCI-MS m/z: 402 [MH+].

EXAMPLE 59

5-[1-(3-Aminopropyl)-5-fluoro-indol-3-yl]-4-naphthalen-1-yl-2,4-dihydro-[1,2,4]triazol-3-one trifluoroacetate a) [3-(5-fluoro-3-hydrazinocarbonyl-indol-1-yl)-propyl]-carbamic acid tert-butyl ester Caution: 1 eq. of hydrazinium azide is formed!

The sub-title compound was prepared starting from 45c) (362 mg, 1 mmol) in THF (10 mL) and hydrazine hydrate (100 μL, 2 mmol). The mixture was stirred for 2 hours at room temperature, diluted with water and extracted with several portions of ethyl acetate. The combined organic phases were dried and concentrated to give the sub-title compound (332 mg, 95%).

$^1$H NMR (400 MHz, DMSO-d6): δ9.16 (1H, bs); 8.05 (1H, bs); 7.82 (1H, dd); 7.56 (1H, dd); 7.07 (1H, dt); 6.96 (1H, bt); 4.34 (2H, bs); 4.21 (3H, t); 2.90–2.95 (2H, m); 1.89 (2H, p); 1.40 (9H, s).

APCI-MS m/z: 351 [MH+].

The title compound was prepared in a manner analogous to Example 57 starting from compound a) and 1-isocyanato-naphthalene.

$^1$H NMR (400 MHz, DMSO-d$_6$): δ12.16 (1H, s); 8.22–8.18 (1H, m); 8.12 (1H, d); 7.80 (1H, dd); 7.71–7.69 (1H, m); 7.70 (1H, s); 7.65–7.58 (3H, m); 7.56 (2H, d); 7.55 (1H, dd); 7.14 (1H, dt); 6.28 (1H, s); 4.03–3.90 (2H, m); 2.49–2.39 (2H, m); 1.68 (2H, p).

APCI-MS m/z: 402 [MH+].

EXAMPLE 60

5-(5-Fluoro-1-methyl-indol-3-yl)-4-{5-fluoro-1-[2-(4-methyl-piperazin-1-yl)-ethyl]-indol-3-yl}-2,4-dihydro-[1,2,4]triazol-3-one bistrifluoroacetate a) 4-[5-Fluoro-1-(2-hydroxy-ethyl)-indol-3-yl]-5-(5-fluoro-1-methyl-indol-3-yl)-2,4-dihydro-[1,2,4]trazol-3-one The sub-title compound was prepared as described in Example 1.

$^1$H-NMR (400 MHz, DMSO-d$_6$): 12.92 (1H, s); 8.86 (1H, dd, J 10.1 and 2.6 Hz); 8.81 (1H, s); 8.72 (1H, dd, J 9.1 and 4.3 Hz); 8.50 (1H, dd, J 8.4 and 4.5 Hz); 8.15 (1H, dd, J 9.0 and 2.4 Hz); 8.10 (1H, dd, J 9.0 and 2.1 Hz); 8.04 (1H, dd, J 9.3 and 2.4 Hz); 7.80 (1H, s); 6.03 (1H, t, J 5.3 Hz); 5.38 (2H, t, J 5.3 Hz); 4.83 (2H, q, J 5.2 Hz); 4.60 (3H, s).

MS-APCI+: 410.2 [MH+].

b) Methanesulfonic acid 2-{5-fluoro-3-[3-(5-fluoro-1-methyl-indol-3-yl)-5-oxo-1,5dihydro-[1,2,4]triazol-4-yl]-indol-1-yl}ethyl ester Sub-title compound a) (82 mg, 0.2 mmol), methanesulfonic anhydride (38 mg, 0.22 mmol) and pyridine (0.5 mL) was stirred in dry dichloromethane (25 mL) over night at ambient temperature. The solution was washed with water, dried and concentrated to give the sub-title compound (47 mg, 48%).

$^1$H NMR (400 MHz, DMSO-$d_6$): $\delta$11.93 (1H, s); 7.87 (1H, s); 7.86 (1H, d); 7.76 (1H, dd); 7.49 (1H, dd); 7.19–7.09 (2H, m); 7.02 (1H, d); 6.71 (1H, s); 4.58–4.71 (4H, m); 3.56 (3H, s); 3.07 (3H, s).

APCI-MS m/z: 488 [MH+].

Compound b) (40 mg, 82 μmol) and 1-methyl-piperazine (0.1 mL, 0.8 mmol) in ethanol (4 mL) was heated at 80° C. over night. Trifluoroacetc acid was added and the mixture was concentrated. The residue was purified by HPLC and lyophilized to give the title compound (35 mg, 59%).

$^1$H NMR (400 MHz, DMSO-$d_6$): $\delta$11.94 (1H, s); 7.84 (1H, s); 7.77 (1H, dd); 7.73 (1H, dd); 7.49 (1H, dd); 7.12 (2H, dt); 7.02 (1H, dd); 6.73 (1H, s); 4.40 (2H, t); 3.59 (3H, s); 3.42–3.30 (2H, m); 3.12–2.88 (4H, m); 2.83 (2H, t); 2.76 (3H, s); 2.47–2.34 (2H, m).

APCI-MS m/z: 492 [MH+].

EXAMPLE 61

4-[1-(3-Dimethylamino-propyl)-5-fluoro-indol-3-yl]-5-(5-fluoro-1-methyl-indol-3-yl)-2,4-dihydro-[1,2,4]triazol-3-one hydrochloride The title compound was prepared by the method described in Example 25 starting from the product of Example 18 and dimethylamine in ethanol.

$^1$H NMR (400 MHz, DMSO-$d_6$): $\delta$11.95 (1H, s); 10.40 (1H, bs); 7.87 (1H, s); 7.79–7.75 (2H, m); 7.50 (1H, dd); 7.15 (1H, dt); 7.12 (1H, dt); 7.06 (1H, dd); 6.78 (1H, s); 4.40 (2H, t); 3.62 (3H, s); 3.11–3.04 (2H, m); 2.74 (6H, s); 2.23 (2H, p).

APCI-MS m/z: 451 [MH+].

EXAMPLE 62

4-[1-(3-Ethylamino-propyl)-5-fluoro-indol3-yl]5(5-fluoro1-methyl-indol-3-yl)-2,4-dihydro-[1,2,4]triazol-3-one hydrochloride The title compound was prepared by the method described in Example 25 starting from the product of Example 18 and ethylamine in methanol.

$^1$H NMR (400 MHz, DMSO-$d_6$): $\delta$11.95 (1H, s); 8.69 (2H, bs); 7.88 (1H, s); 7.79–7.75 (2H, m); 7.50 (1H, dd); 7.15 (1H, dt); 7.12 (1H, dt); 7.06 (1H, dd); 6.75 (1H, s); 4.43 (2H, t); 3.61 (3H, s); 2.92 (2H, q); 2.93–2.89 (2H, m); 2.17 (2H, p); 1.19(3H, t).

APCI-MS m/z: 451 [MH+].

EXAMPLE 63

4-[1-(3-Aminopropyl)-5-fluoro-indol-3-yl]-5-(6-benzyloxy-1-methyl-indol-3-yl)-2,4-dihydro-[1,2,4]triazol-3-one trifluoroacetate The title compound was prepared according to the method described in Example 45. The crude product obtained was heated at reflux over night in a mixture of ethanol (10 mL) and 1M sodium hydroxide (10 mL). Trifluoroacetic acid was added and the mixture was evaporated. The residue was purified by HPLC and lyophilized to give the title compound (220 mg, 50%).

$^1$H NMR (400 MHz, DMSO-$d_6$): $\delta$11.90 (1H, s); 7.98 (1H, d); 7.83 (1H, s); 7.79 (3H, bs); 7.75 (1H, dd); 7.51–7.48 (2H, m); 7.43–7.40 (2H, m); 7.38–7.32 (1H, m); 7.16 (1H, dt); 7.12 (1H, d); 7.04 (1H, dd); 6.90 (1H, dd); 6.50 (1H, s); 5.15 (2H, s); 4.39 (2H, t); 3.52 (3H, s); 2.86–2.78 (2H, m); 2.11 (2H, p)

APCI-MS m/z: 511 [MH+].

EXAMPLE 64

4-[1-(3-Aminopropyl)-5-fluoro-indol-3-yl]-5-(6-hydroxy-1-methyl-indol-3-yl)-2,4-dihydro-[1,2,4]triazol-3-one trifluoroacetate The compound obtained in Example 63 (176 mg, 0.28 mmol) was dissolved in methanol (100 mL) and palladium (10 wt. % on activated charcoal, 200 mg) was added. The mixture was hydrogenated at ambient temperature at 60 psi over night, filtered through Celite® and concentrated in vacuo. The residue was purified by HPLC and lyophilized to give the title compound (104 mg, 69%).

$^1$H NMR (400 MHz, DMSQ-$d_6$): $\delta$11.86 (1H, s); 9.29 (1H, bs); 7.89 (1H, d); 7.82 (1H, s); 7.80 (3H, bs); 7.75 (1H, dd); 7.15 (1H, dt); 7.03 (1H, dd); 6.68–6.73 (2H, m); 6.39 (1H, s); 4.39 (2H, t); 3.44 (3H, s); 2.86–2.78 (2H, m); 2.11 (2H, p)

APCI-MS m/z: 421 [MH+].

EXAMPLE 65

4-[1-(3-Aminopropyl)-7-bromo-indol-3-yl]-5-(5-fluoro-1-methyl-indol-3-yl)-2,4-dihydro-[1,2,4]triazol-3-one trifluoroacetate The title compound was prepared as described in Example 11, starting from 7-bromo-indole.

$^1$H NMR (400 MHz, DMSO-$d_6$): $\delta$12.00 (1H, s); 7.86 (1H, s); 7.79 (1H, dd, J 9.0 and 2.5 Hz); 7.74 (3H, bs); 7.51 (1H, dd); 7.50 (1H, d, J 8.2 Hz); 7.29 (1H, d, J 7.6 Hz); 7.14 (1H, dt, J 9.2 and 2.7 Hz); 7.01 (1H, t, J 7.7 Hz); 6.74 (1H, s); 4.69 (2H, t, J 6.4 Hz); 3.61 (3H, s); 2.88–2.79 (2H, m); 2.22–2.13 (2H, m).

APCI-MS m/z: 483 [MH+].

EXAMPLE 66

4-[1-(3-Amiinomethyl-benzyl)-5-fluoro-indol-3-yl]-5-(5-fluoro-1-methyl-indol-3-yl)-2,4-dihydro-[1,2,4]triazol-3-one trifluoroacetate a) 3-(5-Fluoro-indol-1-ylmethyl)-benzylamine Sodium hydride (55% dispersion in oil, 63 mg, 1.44 mmol) was added to a solution of 5-fluoro-indol (150 mg, 1.11 mmol) in dry DMF (3 mL). The mixture was stirred under nitrogen for 15 min. 2-(3-Bromomethyl-benzyl)-isoindole-1,3-dione (403 mg, 1.22 mmol) was added and the mixture was stirred at room temperature over night. After cooling, aqueous methylamine (40%, 5 mL) was added and this mixture was heated at 80° C. over night. Ethyl acetate was added and the organic phase was washed three times with water, brine, dried and concentrated to give 312 mg of the sub-title compound sufficiently pure for the next step.

b) [3-(5-Fluoro-indol-1-ylmethyl)-benzyl]-carbamic acid tert-butyl ester

To a stirred solution of crude a) (0.31 g, 1.11 mmol) in THF (17 mL), di-tert-butyl dicarbonate (247 mg, 1.13 mmol) was added, followed by aqueous sodium hydroxide (1M, 1.7 mL) and water (3.3 mL). After 30 min the THF was evaporated and ethyl acetate (15 mL) and water (15 mL) were added. The aqueous phase was extracted with ethyl acetate and the combined organic phases were washed twice with water, brine dried and concentrated. The residue was purified by flash chromatography to give 231 mg (59%) of the sub-title compound.

$^1$H NMR (400 MHz, CDCl$_3$): δ7.31–6.87 (8H, m); 6.51 (1H, d, J 3.0 Hz); 5.29 (2H, s); 4.80 (1H, bs); 4.26 (2H, s), 1.45 (9H, s).

c) 1-[3-(tert-Butoxycarbonylamino-methyl-benzyl]-5-fluoro-indole-3-carboxylic acid Trichloroacetyl chloride (157 μL, 1.41 mmol) and pyridine (228 μL, 2.82 mmol) were added to a solution of compound b) (100 mg, 0.28 mmol) in dioxan (1 mL). The mixture was heated at 80° C. for 2.5 h and then poured on ice. Ethyl acetate was added and the aqueous phase was extracted twice with ethyl acetate. The combined organic phases were washed three times with water, brine, dried and concentrated. The residue was dissolved in methanol (1 mL). Aqueous sodium hydroxide (25%, 2.5 mL) was added and the mixture was heated to 90° C. for 2.5 h. After cooling the mixture was acidified by addition of 1M hydrochloric acid. The aqueous solution was extracted three times with ethyl acetate. The combined organic phases were washed with brine, dried and concentrated to give 119 mg of the sub-title compound, sufficiently pure for the next step.

APCI-MS m/z: 299 [MH+]-t-Boc.

d) [3-(3-Azidocarbonyl-5-fluoro-indol-1-ylmethyl)-benzyl]-carbamic acid tert-butyl ester The sub-title compound was prepared from compound c) according to the procedure described in Example 1.

$^1$H NMR (400 MHz, CDCl$_3$): δ7.93 (1H, dd, J 9.4 and 2.5 Hz); 7.87 (1H, s); 7.35–6.98 (6H, m); 5.31 (2H, s); 4.84 (1H, bs); 4.29 (2H, s); 1.45 (9H, s).

e) 4-[1-(3-tert-butoxycarbonylaminomethyl-benzyl)-5-fluoro-1H-indol-3-yl]-1-(1-methyl-indol-3-carbonyl) semicarbazide Compound d) in dry toluen (1.5 mL) was stirred at reflux for 1 h. After cooling to room temperature this solution was added to a mixture of Example 11e) (42 mg, 0.205 mmol) in dry THF (12 mL) and stirred over night. The mixture was concentrated to give the crude sub-title compound.

APCI-MS m/z: 502 [MH+]-t-Boc. N,O-Bis (trimethylsilyl)-trifluoroacetamide (0.47 mL, 1.78 mmol) and N,N-diisopropylethylamine (0.20 mL, 1.17 mmol) in xylene (2 mL) was added to compound e) (0.205 mmol) The mixture was heated at 140° C. for 4 hours and therafter evaporated. The residue was dissolved in hydrochloric acid (3 M in ethyl acetate), stirred for 2 hours and the solvents were removed in vacuo. The residue was purified by preparative HPLC and lyophilized to give 23 mg (19%) of the title compound.

$^1$H NMR (400 MHz, DMSO-d$_6$): δ11.97 (1H, s); 8.15 (3H, bs); 7.93 (1H, s); 7.75 (1H, dd, J 10.0 and 2.6 Hz); 7.65 (1H, dd, J 9.5 and 4.4 Hz); 7.53 (1H, s); 7.50 (1H, dd,J 9.1 and 4.5 Hz); 7.46–7.40 (2H, m); 7.23 (1H, d); 7.16–7.06 (3H, m); 6.75 (1H, s); 5.53 (2H, s); 4.04 (2H, q, J 5.9 Hz); 3.57 (3H, s).

APCI-MS m/z: 485 [MH+].

EXAMPLE 67

4-[1-(3-Andnopropyl)-5-methoxyindol-3-yl]-5-(1-methyl-indol-3-yl)-2,4-dihydro-[1,2,4]triazol-3-one trifluoroacetate The title compound was prepared according to the method described in Example 66. [3-(3-Azidocarbonyl-5-methoxy-indol-1-yl)-propyl]-carbamic acid tert-butyl ester was prepared as described in Example 44c) starting from 5-methoxy-indole.

$^1$H NMR (400 MHz, DMSO-d$_6$): δ11.90 (1H, s); 8.11 (1H, d, J 7.8 Hz); 7.82 (3H, bs); 7.69 (1H, s); 7.61 (1H, d, J 9.0 Hz); 7.46 (1H, d, J 8.2 Hz) 7.25 (1H, dt, J 7.6 Hz and 1.3 Hz); 7.17 (1H, dt, J 7.5 and 1.2 Hz); 6.91 (1H, dd, J 8.9 and 2.4 Hz); 6.68 (1H, d, J 2.3 Hz); 6.63 (1H, s); 4.35 (2H, t, J 6.8 Hz); 3.64 (3H, s); 3.57 (3H, s); 2.85–2.75 (2H, m); 2.15–2.05(2H, m).

APCI-MS m/z: 417.1 [MH+].

EXAMPLE 68

4-[1-(3-Aminopropyl)-5-fluoro-indol-3-yl]-5-(6-chloro-1-methyl-indol-3-yl)-2,4-dihydro-[1,2,4]triazol-3-one trifluoroacetate The title compound as prepared according to the method described in Example 66 starting from 45c) and 6-chloro-1-methyl-indole-3-carboxylic acid hydrazide. The hydrazide was prepared as described in the synthesis of Example 11e).

hu 1H NMR (400 MHz, DMSO-d$_6$): δ11.98 (1H, s); 8.09 (1H, d, J 8.4 Hz); 7.84 (1H, s); 7.81 (3H, bs); 7.75 (1H, dd, J 9.2 and 4.2 Hz); 7.63 (1H, d, J 1.5 Hz); 7.20 (1H, dd, J 8.6 and 1.9 Hz); 7.15 (1H, dt, J 9.2 and 2.3 Hz); 7.06 (1H, dd, J 9.3 and 2.3 Hz); 6.68 (1H, s); 4.39 (2H, t J 6.8 Hz); 3.58 (3H, s); 2.86–2.77(2H, m); 2.16–2.06 (2H, m ).

APCI-MS m/z: 439 [MH+].

EXAMPLE 69

4-(8-Anino-6,7,8,9-tetrahydro-pyrido[1,2-a]indol-10-yl)-5-(5-fluoro-1-methyl-indol-3-yl)-2,4-dihydro-[1,2,4]triazol-3-one trifluoroacetate a) (10-Chlorocarbonyl-6,7,8,9-tetrahydro-pyrido[1,2-a] indol-8-yl)-carbamic acid tert-butyl ester A solution of (6,7,8,9-tetrahydro-pyrido[1,2-a]indol-8-yl)-carbamic acid tert-butyl ester (400 mg, 1.40 mmol) in dry THF (5 mL) was cooled to 0° C. Triphosgene (208 mg, 0.7 mmol) dissolved in dry THF (3 mL) and triethylamine (194 μL, 1.40 mmole) were added. A precipitation was formed. The reaction was allowed to reach room temperature and after 2 h the mixture was evaporated and the crude product was used in the next step. APCI-MS m/z: 345 [MH+] (analysis performed on a sample quenched with methanol, thus the mass corresponds to the methylester).

b) (10-Azidocarbonyl-6,7,8,9-tetrahydro-pyrido[1,2-a] indol-8-yl)-carbamic acid tert-butyl ester A solution of compound a) (489 mg, 1.4 mmol) in dry DMF (6 mL) was cooled to 0° C. Sodium azide (227 mg, 3.5 mmol) was added. The reaction was allowed to reach room temperature and was stirred over night. It was poured into a mixture of ethyl acetate and water. The organic layer was separated and the water phase was washed twice with ethyl acetate. The combined organic phases were washed with a minimal amount of water and dried over sodium sulfate. The solution was evaporated and the crude mixture was used in the next step.

IR: V: 2129.8 cm$^{-1}$, 1666.4 cm$^{-1}$.

c) 4-(8-tert-Butoxycarbonylamino-6,7,8,9-tetrahydro-pyrido[1,2-a]indol-10-yl)-1-(5-fluoro-1-methyl-indol-3-carbonyl)semicarbazide Crude compound b) was dissolved in toluene (14 mL) and heated at 110° C. for 1.5 hours. Compound 11e) (100 mg, 0.48 mmol) in dry THF (15 mL) was added and the mixture was stirred over night, evaporated and used in the next step without further purification.

APCI-MS m/z: 535 [MH+].

The title compound was prepared by the method described in Example 1, obtained as a mixture of two diasteroisomers. The diasterioisomers could be separated by HPLC to give 45 mg of isomer A and 51 mg of isomer B.

Isomer A:

$^1$H NMR (400 MHz, DMSO-d$_6$): 11.97 (1H, s); 8.07 (3H, bs), 7.85 (1H, dd, J 10.1 and 2.6 Hz); 7.57 (1H, d, J 8.2 Hz); 7.48 (1H, dd J 9.0 and 4.5 Hz); 7.26 to 7.17 (2H, m); 7.16 to 7.04 (2H, m); 6.62 (1H, s); 4.56 to 4.48 (1H, m); 4.12 (1H, dt, J 12.1 and 4.8 Hz); 3.72 (1H, bs); 3.56 (3H, s); 3.19 (1H, dd, J 16.2 and 4.7 Hz); 2.63 (1H, dd, J 16.3 and 10.0 Hz); 2.45 to 2.37 (1H, m); 2.24 to 2.11 (1H, m).

Isomer B:

$^1$H NMR (400 MHz, DMSO-d$_6$): 11.98 (1H, s); 8.12 (3H, bs); 7.86 (1H, dd, J 10.2 and 2.7 Hz); 7.57 (1H, d, J 8.2 Hz); 7.47 (1H, dd, J 9.0 and 4.4 Hz); 7.22 (1H, t, J 7.8 Hz); 7.15 to 7.09 (2H, m); 7.05 (1H, t, J 7.1 Hz); 6.73 (1H, s); 4.56 to 4.48 (1H, m); 4.16 (1H, dt, J 11.7 and 4.7 Hz); 3.68 (1H, bs); 3.55 (3H, s); 3.08 (1H, dd, J 16.3 and 5.1 Hz); 2.87 (1H, dd, J 16.2 and 10.2 Hz); 2.47 to 2.39 (1H, m); 2.23 to 2.11 (1H, m).

APCI-MS m/z: 417 [MH+].

The stereoisomerism can be related to the asymmetric carbon in the 6-membered ring, adjacent to the amino group and to the fact that a form of atropisomerism is formed in the ring clousure step. The left hand side indole, to which the six-membered ring is annelated and the right hand side indole can not rotate freely. The rotameres interconvert when heated. This can easily be followed by NMR.

EXAMPLE 70

4-(8-Aminomethyl-6,7,8,9-tetrahydro-pyrido[1,2-a]indol-10-yl)-5-(1-methyl-indazol-3-yl)-2,4-dihydro-[1,2,4]triazol-3-one trifluoroacetate The title compound was prepared according to the method described in Example 13 from 13a) and 1-methyl-indazole-3-carboxylic acid hydrazide. The product was obtained as a mixture of stereosiomers (rotamers) and could be detected by NMR (cf Example 69).

$^1$H NMR (400 MHz, DMSO-d$_6$): 12.28 (0.5H, s); 12.27 (0.5H, s), 8.07 (1H, dd, J 8.3 and 14.5 Hz); 7.86 (3H, bs); 7.62 (1H, dd, J 8.4 and 2.5 Hz); 7.48 to 7.41 (2H, m); 7.25 (1H, t, J 7.6 Hz); 7.14 to 6.92 (3H, m); 4.51 to 4.40 (1H, m); 4.00 to 3.88 (1H, dq, J 15.4 and 4.5 Hz); 3.81 (1.5H, s); 3.79 (1.5H, s); 3.07 (1H, dt, J 16.2 and 4.1 Hz); 3.01 to 2.85 (2H, m); 2.63 to 2.43 (1H, m); 2.33 to 2.24 (1H, m); 2.24 to 2.13 (1H, m); 1.91 to 1.73 (1H, m).

APCI-MS m/z: 414 [MH+].

EXAMPLE 71

4-(2-Aminomethyl-2,3-dihydro-pyrrolo[1,2-a]indol-9-yl)-5-(5-fluoro-1-methyl-indol-3-y )-2,4-dihydro-[1,2,4]triazol-3-one trifluoroacetate

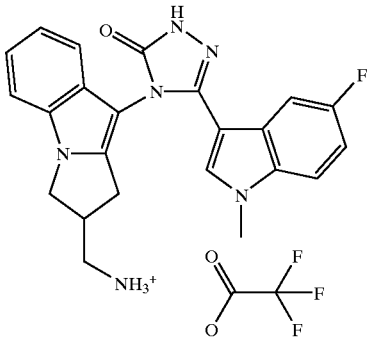

a) 4-(2-Azidomethyl-2,3-dihydro-1H-pyrrolo[1,2-a]indole-9-yl)-5-(5-fluoro-1-methyl-indol-3-yl)-2,4-dihydro-[1,2,4]triazol-3-one The sub-title compound was prepared according to the method described in Example 69 starting from Example 11e) and 2-azidomethyl-2,3-dihydro-1H-pyrrolo[1,2-a]indole-9-carbonyl azide.

APCI-MS m/z: 443 [MH+].

The title compound was prepared by the method described in Example 11, and was obtained as a mixture of stereoisomers (rotamers) which could be detected by NMR (cf Example 70).

$^1$H NMR (400 MHz, DMSO-d$_6$): 11.92 (1H, s); 7.95 (3H, bs); 7.81 (1H, dd, J 10.0 and 2.6 Hz); 7.48 (1H, dd, J 9.0 and 4.6 Hz); 7.43 (1H, d, J 8.2 Hz); 7.20 to 7.08 (3H, m); 7.00 (1H, bt, J 7.7 Hz); 6.79 (1H, d, J 1.9 Hz); 4.48 to 4.37 (1H, m); 4.11 (0.5H, dd, J 10.7 and 5.9 Hz); 4.03 (0.5H, dd, J 10.2 and 6.6 Hz); 3.58 (1.5H, s); 3.57 (1.5H, s); 3.35 to 3.24 (1H, m); 3.21 to 2.94 (3H, m); 2.84 (0.5H, dd, J 16.7 and 7.0 Hz); 2.71 (0.5H, dd, J 16.3 and 5.8 Hz).

APCI-MS m/z: 417 [MH+].

EXAMPLE 72

4-[1-(3-Aminopropyl)-6-hydroxy-indol-3-yl-]-5-(5-fluoro-1-methyl-indol-3-yl)-2,4-dihydro-[1,2,4]triazol-3-one trifluoroacetate a) 4-[1-(3-Aminopropyl)-6-benzyloxy-indol-3-yl-]-5-(5-fluoro-1-methyl-indol-3-yl)-2,4-dihydro-[1,2,4]triazol-3-one trifluoroacetate The sub-title compound was prepared by the method described in Example 44.

APCI-MS m/z: 511 [MH+].

The title compound was prepared as described in Example 64 starting from a).

$^1$H NMR (400 MHz, DMSO-d$_6$): 11.88 (1H, s); 9.30 (1H, s); 7.83 to 7.70 (4H, m); 7.52 to 7.45 (2H, m); 7.10 (1H, bt, J 8.4 Hz); 7.01 (1H, d, J 8.4 Hz); 6.96 (1H, s); 6.66 to 6.59 (2H, m); 4.23 (2H, t, J 6.7 Hz); 3.56 (3H, s); 2.80 (2H, m); 2.06 (2H, m).

APCI-MS m/z: 421 [MH+].

EXAMPLE 73

4-[1-(3-Aminopropyl)-6-fluoro-indol-3-yl]-5-(1-methyl-indol-3-yl)-2,4-dihydro-[1,2,4]triazol-3-one trifluoroacetate The title compound was prepared by the method described in Example 11.

¹H NMR (400 MHz, acetone-d₆): δ10.99 (1H, bs); 8.25 (1H, d, J 8.0 Hz); 7.56 (1H, s); 7.31 to 7.39 (3H, m); 7.23 (1H, t, J 7.6 Hz); 7.16 (1H, t, J 7.0 Hz); 6.87 (1H, dt, J 9.2 and 2.3 Hz); 6.68 (1H, s); 4.40 (2H, t, J 6.8 Hz); 3.55 (3H, s); 3.18 (2H, t, J 6.4 Hz); 2.84 ) 2H, bs); 2.17 (2H, m).

MS-ESI+: mn/z 405.2 [MH+].

EXAMPLE 74

4-[1-(3-Aminopropyl)-5-fluoro-indol-3-yl]-5-(3-bromo-phenyl)-2,4-dihydro-[1,2,4]triazol-3-one hydrochloride The title compound was prepared by the method described in Example 45 starting from Example 45c) and 3-bromo-benzoic acid hydrazide.

¹H NMR (400 MHz, DMSO-d₆): δ12.20 (1H, s); 7.71 (1H, s); 7.63 to 7.67 (2H, m); 7.55 (1H, s); 7.32 (1H, d, J 7.9 Hz); 7.22 (1H, t, J 7.8 Hz); 7.04 to 7.11 (2H, m); 4.29 (2H, t, J 7.2 Hz); 2.71 (2H, t, J 7.4 Hz); 2.00 (2H, m).

MS-ESI+: m/z 430.1 [MH+].

EXAMPLE 75

4-[1-(3-Aminopropyl)-5-fluoro-indol-3-yl]-5-(4-bromo-phenyl)-2,4-dihydro-[1,2,4]triazol-3-one hydrochloride The title compound was prepared by the method described in Example 66 starting from Example 45c) and 4-bromo-benzoic acid hydrazide.

¹H NMR (400 MHz, DMSO-d₆): δ12.20 (1H, s); 7.98 (2H, bs); 7.75 (1H, s); 7.75 (1H, dd, J 9.0 and 4.4 Hz); 7.50 (2H, dm, J 8.4 Hz); 7.38 (2H, dm, J 8.6 Hz); 7.06 (1H, dt, J 9.2 and 2.5 Hz); 6.99 (1H, dd, J 9.5 and 2.5 Hz); 4.32 (2H, t, J 6.7 Hz); 2.70 (2H, m); 2.02 (2H, m).

MS-LSIMS+: m/z 430.0 [MH+].

EXAMPLE 76

4-[1-(3-Aminopropyl)-5-fuoro-indol-3-yl]5(3,5dichloro-phenyl)-2,4-dihydro-[1,2,4]triazol-3-one trifluoroacetate The title compound was prepared by the method described in Example 66 starting from Example 45c) and 3,5-dichloro-benzoic acid hydrazide.

¹H NMR (400 MHz, DMSO-d₆): δ12.34 (1H, s); 7.75 (1H, s); 7.66 to 7.83 (2H, m); 7.65 (1H, dd, J 9.7 and 5.3 Hz); 7.61 (1H, t, J 1.9 Hz); 7.34 (2H, d, J 1.9 Hz); 7.07 to 7.12 (2H, m); 4.31 (2H, t, J 6.9 Hz); 2.74 (2H, bs); 2.00 (2H, m).

MS-LSIMS+: m/z 420.0 [MH+].

EXAMPLE 77

4-[1-1-Benzyl-piperidin-4-ylmethyl)-5-fluoro-indol-3-yl]-5-(5-fluoro-1-methyl-indol-3-yl)-2,4-dihydro-[1,2,4]triazol-3-one hydrochloride a) 1-Benzyl-1-azonia-bicyclo[2,2,1]heptane methanesulfonate Methanesulfonyl chloride (0.22 mL, 2.85 mmole) in dichloromethane (2 mL) was added dropwise to a ice-cooled solution of N-benzyl-4-hydroxymethyl-piperidine (531 mg, 2.59 mmol) and N,N-diisopropylethylamine (0.66 mL, 3.88 mmol) in dichloromethane (3 mL). The mixture was stirred for 5 min, diluted with tert-butyl methyl ether, washed with water and brine. The solvents were removed to give the sub-title compound.

¹H NMR (400 MHz, CDCl₃): δ7.63 (2H, m); 7.41 (3H, m); 5.03 (2H, s); 3.88 (2H, m); 3.65 (2H, s); 3.40 (2H, m); 2.88 (1H, m); 2.83 (3H, s); 2.27 (2H, m); 1.73 (2H, m).

b) 1-(1-Benzyl-piperidin-4-ylmethyl)-5-fluoro-indole

5-Fluoro-indole (391 mg, 2.89 mmol) in DMF (2 mL) was added drop-wise to a stirred suspension of sodium hydride (60%, 116 mg, 3.04 mmole) in DMF (2 mL) at 0° C. After 30 minutes compound a) (987 mg, 3.47 mmol), dissolved in DMF (6 mL), was added and the reaction mixture was stirred at 50° C. over night. The mixture was diluted with ethyl acetate, washed three times with water and dried over sodium sulfate. Evaporation of the solvent gave the crude product as a mixture of two constitution isomers. Silica gel chromatography (heptane-ethyl acetate-methanol, 20:80:5) gave the sub-title compound (138 mg, 15%) and 1-[2-(1-benzyl-pyrrolidin-3-yl)-ethyl]-5-fluoro-1H-indole (338 mg 36%).

Sub-title compound:

¹H NMR (400 MHz, CDCl₃): δ7.22 to 7.29 (6H, m); 7.20 (1H, dd, J 9.0 and 4.4 Hz); 7.07 (1H, d, J 3.0 Hz); 6.41 (1H, dd, J 3.2 and 1.8 Hz); 3.95 (2H, d, J 7.2 Hz); 3.46 (2H, s); 2.86 (2H, bd, J 11.6 Hz) 1.77 to 1.92 (4H, m); 1.49 to 1.61 (3H, m); 1.35 (2H, m).

APCI-MS: 323.2 [MH+].

1-[2-(1-benzyl-pyrrolidin-3-yl)-ethyl]-5-fluoro-1H-indole (constitution isomer):

¹H NMR (400 MHz, CDCl₃): δ7.22 to 7.32 (7H, m). 7.18 (dd, J 9.0 and 3.3 Hz); 7.04 (1H, d, J 3.2 Hz); 6.93 (1H, dt, J 9.0 and 2.5 Hz); 6.40 (1H, dd, J 3.1 and 0.6 Hz); 4.06 (2H, m); 3.57 (2H, J 12.8 Hz); 2.73 (1H, m); 2.63 (1H, m); 2.49 (1H, m); 2.17 to 1.81 (5H, m); 1.42 (1H, m).

APCI-MS: 323.2 [MH+].

c) [1-(1-Benzyl-piperidin-4-ylmethyl)-5-fluoro-indol-3-yl]-2,2,2-trichloro-ethanone Pyridine (40 μL, 471 μmole) and trichloroacetyl chloride (0.14 mL, 1.28 mmole) was added at room temperature to a solution of the sub-title compound b) (138 mg, 428 μmol) in dichloromethane (3 mL). The reaction mixture was stirred over night and diluted with ethyl acetate. The mixture was washed with water, saturated aqueous sodium hydrogen carbonate and dried over sodium sulfate. Purification by silica gel chromatography (heptane-ethyl acetate-methanol, 50:50:1 followed by 0:100:2) gave the sub-title compound (336 mg, 78%).

APCI-MS: 467.1, 469.0 [MH+].

d) 1-(1-Benzyl-piperidin-4-ylmethyl)-5-fluoro-1H-indol-3-carboxylic acid hydrazide Hydrazin hydrate (33 μL, 672 μmol) was added to compound c) (157 mg, 336 μmole) in THF (1 mL). The reaction mixture was heated for 3 h at 80° C., diluted with ethyl acetate, washed twice with brine and dried over sodium carbonate. Purification by silica gel chromatography (ethyl acetate-methanol-ammonia; 90:10:0 followed by 80:20:2) gave 95 mg (74%) of the sub-title compound.

APCI-MS: 381.3 [MH+].

e) 1-(1-Benzyl-piperidin-4-ylmethyl)-5-fluoro-1H-indol-3-carbonyl azide

Sodium nitrite (34 mg, 499 μmol), dissolved in a minimum amount of water, was added to compound d) (95 mg, 250 μmol) in water/acetic acid (1:1, 1 mL) at 0° C. The reaction mixture was after approx. 2 minutes diluted with water and ethylacetate and neutralized with sodium carbonate. The organic layer was separated, washed with water and dried over sodium sulfate. Evaporation of the solvent gave 100 mg of the sub-title compound in a quantitave yield.

IR: V: 2132 (vs), 1673 (s).

The title compound was prepared as described in Example 1 starting from sub-title compound e) and the product of Example 11e).

¹H NMR (400 MHz, DMSO-d₆): δ11.91 (1H, s); 10.14 (1H, bs); 7.72 (1H, s); 7.65 (1H, dd, J 9.0 and 4.2 Hz); 7.60 (1H, dd, J 10.1 and 4.5 Hz); 7.50 to 7.52 (2H, m); 7.43 to 7.45 (3H, m); 7.41 (1H, dd, J 9.0 and 4.5 Hz); 7.01 to 7.10 (3H, m); 6.82 (1H, s); 4.21 (2H, d, J 5.0 Hz); 4.14 (2H, d, J 7.1 Hz); 3.54 (3H, s); 3.28 (2H, m); 2.80 (2H, bq, J 10.6 Hz); 2.03 (1H, m); 1.47 to 1.69 (4H, m);
MS-LSIMS+: m/z 553.3 [MH+].

EXAMPLE 78

5-(5-Fluoro-1-methyl-indol-3-yl)-4-(5-fluoro-1-piperidin-4-ylmethyl-indol-3-yl)-2,4-dihydro-[1,2,4]triazol-3-one hydrochloride The title compound in Example 77 was hydrogenated in acetic acid/methanol (1:1) at 50 psi for 24 h with palladium on carbon (10%) to give the title compound.

¹H NMR (400 HMz, DMSO-d₆): δ11.91 (1H, s); 8.51 (1H, bs); 8.23 (1H, bs); 7.75 (1H, s); 7.65 to 7.71 (2H, m); 7.45 (1H, dd, J 9.0 and 4.5 Hz); 7.02 to 7.12 (3H, m); 6.75 (1H, s); 4.17 (2H, d, J 7.3 Hz); 3.56 (3H, s); 3.25 (2H, bd, J 12.5 Hz); 2.80 (2H, bq, J 10.3 Hz); 2.12 (1H, m); 1.62 (2H, bd, J 12.4 Hz); 1.36 (2H, bq, J 12.0 Hz).

MS-LSIMS+: m/z 463.1 [MH+].

EXAMPLE 79

4-[1-(1-Benzyl-piperidin-4-ylmethyl)-indol-3-yl]-5-(1-methyl-indol-3-yl)-2,4-dihydro-[1,2,4]triazol-3-one hydrochloride The title compound was prepared in a manner analogous to Example 77. During the synthesis of the title compound, a constitution isomer was also obtained as an intermediate (cf Example 77). This was used for the synthesis of Example 81.

¹H NMR (400 HMz, DMSO-d₆): δ11.88 (1H, s); 8.04 (1H, bd, J 8.0 Hz); 7.66 (1H, s); 7.64 (1H, bs); 7.39 (1H, d, J 8.4 Hz); 7.18 to 7.36 (8H, m); 7.10 (1H, t, J 7.8 Hz); 7.05 (1H, t, J 8.3 Hz); 6.62 (1H, bs); 4.16 (2H, d, J 6.8 Hz); 3.43 (2H, bs); 3.32 (3H, s); 2.79 (2H, m); 1.85 (3H, m); 1.45 (2H, m); 1.29 (2H, m). MS-LSIMS+: m/z 517.3 [MH+].

EXAMPLE 80

5-(1-Methyl-indol-3-yl)-4-(1-piperidin-4-ylmethyl-indol-3-yl)-2,4-dihydro-[1,2,4]triazol-3-one trifluoroacetate The title compound was prepared as described in Example 78 starting from the title compound in Example 79.

¹H NMR (400 HMz, DMSO-d₆): δ11.90 (1H, s); 8.48 (1H, bs); 8.18 (1H, bs); 8.04 (1H, d, J 7.6 Hz); 7.70 (1H, s); 7.67 (1H, d, J 8.5 Hz); 7.43 (1H, d, j 8.2 Hz); 7.20 to 7.27 (3H, m); 7.13 (1H, t, J 7.4 Hz); 7.06 (1H, t, J 7.5 Hz); 6.67 (1H, s); 4.20 (2H, s); 3.54 (3H, s); 3.31 (2H, m); 2.83 (2H, bq, J 11.4 Hz); 2.17 (1H, bs); 1.66 (2H, bd, J 11.8 Hz); 1.39 (2H, bq, J 11.3 Hz).
MS-LSIMS+: m/z 427.1 [MH+].

EXAMPLE 81

4-{1-[2-(1-Benzyl-pyrrolidin-3-yl)-ethyl]-indol-3-yl}-5-(1-methyl-indol-3-yl)-2,4-dihydro-[1,2,4]triazol-3-one hydrochloride The title compound was prepared in a manner analogous to Example 77, starting from the constitution isomer derived in the synthesis of the title compound in Example 79.

¹H NMR (400 HMz, DMSO-d₆): δ11.88 (1H, s); 8.09 (1H, d, J 8.0Hz); 7.72 (1H, s); 7.60 (1H, d, J 8.6 Hz); 7.41 (1H, d, J 8.2 Hz); 7.20 to 7.25 (8H, m); 7.13 (1H, t, J 7.5 Hz); 7.04 (1H, t, J 7.7 Hz); 6.59 (1H, s); 4.25 (2H, t, J 6.8 Hz); 3.54 (1H, bs); 3.50 (3H, s); 3.32 (2H, s); 2.70 (1H, m); 2.40 (1H, bs); 2.14 (1H, bs); 1.82 to 1.99 (4H, m); 1.43 (1H, m).
MS-LSIMS+: m/z 517.3 [[MH+].

EXAMPLE 82

5-(1-Methyl-indol-3-yl)-4-[1-(2-pyrrolidin-3-yl-ethyl)-indol-3-yl]-2,4-dihydro-[1,2,4]triazol-3-one hydrochloride The title compound was prepared as described in Example 78 starting from the title compound in Example 81.

¹H NMR (400 HMz, DMSO-d6): δ11.89 (1H, s); 8.06 (1H, d, J 8.0 Hz); 7.72 (1H, s); 7.63 (1H, d, J 8.6 Hz); 7.40 (1H, d, J 8.2 Hz); 7.19 to 7.23 (3H, m); 7.12 (1H, t, J 7.5 Hz); 7.02 (1H, t, J 7.4 Hz); 6.59 (1H, s); 4.27 (2H, t, J 6.8 Hz); 3.50 (3H, s); 3.04 (1H, m); 2.95 (1H, m); 2.84 (1H, m); 2.51 (1H, m); 1.84 to 1.97 (5H, m); 1.39 (1H, m).

MS-ESI+: m/z 427.1 [MH+].

EXAMPLE 83

1-(3-Dimethylamino-propyl)-3-[3-(5-fluoro-1-methyl-indol-3-yl)-5-oxo-1,5-dihydro-[1,2,4]triazol-4-yl]-indole-5-carboxylic acid methyl ester hydrochloride The title compound was prepared in a manner analogous to Example 11, starting from 3-azidocarbonyl-1-(3-dimethylamino-propyl)-1H-indole-5-carboxylic acid methyl ester and the product of Example 11e).

¹H NMR (400 HMz, DMSO-d₆): δ11.98 (1H, s); 7.88 (1H, dd, J 15.5 and 2.7 Hz); 7.84 (2H, s); 7.76 (1H, d, 8.8 Hz); 7.70 (1H, dd, J 10.1 and 2.7 Hz); 7.46 (1H, dd, J 9.0 and 4.4 Hz); 7.09 (1H, dt, J 9.2 and 2.7 Hz); 6.71 (1H, s); 4.32 (2H, t, J 6.8 Hz); 3.56 (3H, s); 3.79 (3H, s); 2.13 (2H, t, J 6.9 Hz); 2.08 (6H, s); 1.92 (2H, m).

MS-LSIMS+: m/z 491.0 [MH+].

EXAMPLE 84

4-[1-(3-Aminopropyl)-5-fluoro-indol-3-yl]-5-(1-methyl-6-trifluoromethyl-indol-3-yl)-2,4-dihydro-[1,2,4]triazol-3-one trifluoroacetate The title compound was prepared by the method described in Example 11 starting from 1,6-dimethyl-indole-3-carboxylic acid hydrazide and the product of Example 11d).

¹H NMR(400 HMz,DMSO-d₆): δ11.99 (1H, s); 8.22 (1H, d, J 8.3 Hz); 7.88 (1H, s);7.70 (5H, m); 7.44 (1H, dd, J 9.5 and 1.3 Hz); 7.10 (1H, td, J 9.1 and 2.5 Hz); 7.02 (1H, dd, J 9.1, 2.5 Hz); 6.83 (1H, s); 4.34 (2H, t, J 6.7 Hz); 3.65 (3H, s); 2.77 (2H, bs); 2.03 (2H, m).

MS-LSIMS+: m/z 473.1 [MH+], 474.1 [MH₂+].

EXAMPLE 85

3-{4-[1-(3-Aminopropyl)-5-fluoro-indol-3-yl]-5-oxo-4,5-dihydro-[1,2,4]triazol-3-yl}-1-methyl-indole-5-carbonitrile trifluoroacetate The title compound was prepared by the method described in Example 11 starting from 5-cyano-1-methyl-indole-3-carboxylic acid hydrazide and the product of Example 11d).

¹H NMR (400 HMz, DMSO-d₆): δ12.03 (1H, s); 8.41 (1H, d, J 1.5 Hz); 7.79 (1H, s); 7.65 (4H, m); 7.59 (1H, dd, J 8.6 and 1.7 Hz); 7.11 (1H, dt, J 7.2 and 2.5 Hz); 7.05 (1H, dd, J 7.3 and 2.5 Hz); 6.83 (1H, s); 4.33 (2H, t, J 6.8 Hz); 3.62 (3H, s); 2.76 (2H, m); 2.03 (2H, m).

MS-LSIMS+: m/z 430.2 [MH+].

EXAMPLE 86

4-{1-[3-(4-Benzyl-piperazin-1-yl)-propyl]-5-fluoro-indol-3-yl}-5-(5-fluoro-1-methyl-indol-3-yl)-2,4-dihydro-[1,2,4]triazol-3-one dihydrochloride The title compound was prepared in a manner anologous to Example 26 starting from the product of Example 18 and 1-benzyl-piperazine.

¹H NMR (400 HMz, CDCl₃): δ7.95 (1H, dd); 7.35 to 7.20 (8H); 7.05 (2H, m); 6.95 (2H, 6.95 (2H, m); 6.15 (1H, s); 4.10 (2H, d, J 4.6 Hz); 3.30 (2H, s); 3.20 (3H, s); 2.40 to 2.25 (8H); 1.95 (2H, d, J 4.6 Hz); 1.15 (2H).

APCI-MS m/z: 582.1 [MH+].

EXAMPLE 87

4-{5-Fluoro-1-[3-(2-hydroxy-ethylamino)-propyl]-indol-3yl}-5-(5-fluoro-1-methyl-indol-3-yl)-2,4-dihydro-[1,2,4]triazol-3-one hydrochloride The title compound was prepared in a manner anologous to Example 26 starting from the product of Example 18 and 2-amino-ethanol.

¹H NMR (400 HMz, CDCl₃): δ7.85 (2H, m); 7.35 (2H, m); 7.30 (1H, s); 7.05 (2H, m); 6.95 (2H, m); 6.40 (1H, s); 4.10 (2H, m); 3.95 (3H, s); 3.55 (2H, m); 3.30 (2H, s); 2.55 (2H, m); 2.00 (2H, m).

APCI-MS m/z: 467.1 [MH+].

EXAMPLE 88

4-[1-(3-Benzylamino-propyl)-5-fluoro-indol-3-yl]-5-(5fluoro-1-methyl-indol-3-yl)-2,4-dihydro-[1,2,4] triazol-3-one hydrochloride The title compound was prepared in a manner anologous to Example 26 starting from the product of Example 18 and benzylamine.

¹H NMR (400 HMz, CDCl₃): δ9.15 (1H, bs); 7.85 (1H, dd); 7.20 to 7.10 (8H); 7.00 (2H, m); 6.25 (1H, s); 4.40 (2H, s); 4.10 (2H, d, J 4.3 Hz); 3.25 (3H, s); 2.25 (2H, d, J, 4.3 Hz); 1.55 (1H, bs); 1.05 (2H, m).

APCI-MS m/z: 514.1 [MH+].

EXAMPLE 89

4-{1-[3-(3,5-Dimethyl-piperazin-1-yl)-propyl]-5-fluoro-indol-3-yl}-5-(5-fluoro-1-methyl-indol-3-yl)-2,4-dihydro-[1,2,4]triazol-3-one dihydrochloride The title compound was prepared in a manner anologous to Example 26 starting from the product of Example 18 and 2,6-dimethyl-piperazine.

¹H NMR (400 HMz, CD₃OD): δ7.55 (1H, s); 7.45 (2H, m); 7.20 (1H, m); 7.00 (1H, m); 6.90 (2H, m); 6.65 (1H, s); 4.15 (2H, t, J 3.7 Hz); 3.65 (2H, m); 3.55 (3H, s); 3.05 (2H, t, J 3.7 Hz); 2.25 (3H, m); 1.60 (6H, s); 1.05 (2H, m).

APCI-MS m/z: 520.4 [MH+].

EXAMPLE 90

4-{1-[3-(2,6-Dimethyl-morpholin-4-yl)-propyl]-5-fluoro-indol-3-yl}-5-(5-fluoro-1-methyl-indol-3-yl)-2,4-dihydro-[1,2,4]triazol-3-one hydrochloride The title compound was prepared in a manner anologous to Example 26 starting from the product of Example 18 and 2,6-dimethyl-morpholine.

¹H NMR (400 HMz, DMSO-d₆): δ7.90 (1H, s); 7.85 (2H, m); 7.55 (1H, m); 7.15 (2H, m); 7.00 (1H, m); 6.80 (1H, s); 4.35 (2H, t); 3.60 (3H, s); 3.55 (2H, d); 3.15 to 3.00 (4H, m); 2.55 (2H, t); 1.15 (6H, 2s); 1.00 (2H, m).

APCI-MS m/z: 521.1[MH+].

EXAMPLE 91

5-(5-Fluoro-1-methyl-indol-3-yl)-4-{5-fluoro-1-[4-(4-methyl-piperazin-1-yl)-butyl]-indol-3-yl}-2,4-dihydro-[1,2,4]triazol-3-one dihydrochloride The title compound was prepared in a manner anologous to Example 26 starting from the product of Example 19 and 1-methylpiperazine.

¹H NMR (400 HMz, CD₃OD): δ7.80 (1H, s); 7.55 (2H, m); 7.20 (1H, m); 7.00 (2H, m); 6.90 (1H, m); 6.60 (1H, s); 4.15 (2H, t); 3.50–3.40 (10H, m); 3.15 (3H, s); 3.00 (3H, s); 2.25 (3H, m); 0.95 (2H, m).

APCI-MS m/z: 520.1 [MH+].

EXAMPLE 92

3-{5-Fluoro-3-[3-(5-fluoro-1-methyl-indol-3-yl)-5-oxo-1,5-dihydro-[1,2,4]triazol-4-yl]-indol-1-ylmethyl}-benzimidic acid methyl ester hydrochloride a) 3-[(5-Fluoro-indol-1-yl)methyl]benzonitrile To a solution of 3 g (22.2 mmol) of 5-fluoroindole in 90 ml of dry DMF was added 8.28 g (23 mmol) NaH and 4.51 g (23 mmol) of 3-bromomethyl benzonitrile. The mixture was stirred overnight at and thereafter distributed between water and dihcloromethane. The water layer was extracted twice with dichloromethane, and the combined organic extracts were washed with brine, dried and evaporated. The oily residue was subjected to flash chromatography eluting with dichloromethane/hexane (1/1), to give 5.75 g (76%) of the subtitle product.

¹H-NMR:(CDCl₃):5.30 (2H, s); 6.55 (1H, d); 6.90 (1H, tt); 7.15 (1H, q); 7.20 (1H, d); 7.30–7.40 (3H, m); 7.55 (1H, t); 7.60 (1H, dd).

APCI-MS m/z: 251.2 [MH+].

b) 3-{[5-Fluoro-3-(2,2,2-trichloroacetyl)-indol-1-yl]methyl}benzonitrile

To a stirred and cooled solution of the product from a) (5.50 g, 22.2 mmol) in 120 ml of dry dioxane and pyridine (3.5 ml, 45 mmol) was slowly injected through a septum, trichloroacetyl chloride (5.4 ml, 45 mmol). The resulting mixture was stirred overnight at 80° C., cooled and distributed between water and ethyl acetate.The water phase was extracted twice with ethyl acetate, and the combined organic phases were washed with brine, dried and evaporated. The residue was subsjected to flash chromatography (ethyl acetate/hexane 1/1) to give 5.6 g (84%) of the subtitle product as an oil.

¹H-NMR (CDCl₃): 5.45 (2H,s); 7.10 (1H,tt); 7.15 (1H, q); 7.30 (1H, d); 7.45–7.50 (2H, m); 7.60 (1H, d); 8.11 (1H, dd); 8.25 (1H, s).

APCI-MS n/z: 395.5 [MH+].

c) 1-(3-Cyanobenzyl)-5-fluoro-indole-3-carboxylic acid hydrazide

To a solution of 5.5 g (14 mmol) of the product from b) in 80 ml of THF was added 1.2 ml (28 mmol) of hydrazine hydrate and the mixture was stirred for 1 h at 50° C. After the complete conversion of the starting material, the solvent was evaporated and the residue was recrystallised from TBME/MeOH to furnish 2.8 g (79%) of the subtitle product.

¹H-NMR (DMSO-d₆): 8.10 (1H, s); 8.0 (1H, dd); 7.90 (1H, m); 7.70 (4H, m); 7.25 (1H, tt); 5.75 (2H, s); 4.5 (1H, bs); 3.50 (2H, bs);

APCI-MS n/z: 309.1 [MH+].

d) 1-(3-Cyanobenzyl)-5-fluoro-indole-3-carbonyl azide

The product from c) (2.8 g, 9 mmol) was dissolved in glacial acetic acid (30 ml) and the solution was cooled in an ice bath. Then, a solution of sodium nitrite (1.25 g 11.8 mmol) in 20 ml of water was added dropwise whereupon a white solid began to precipitate immediately. After the addition was completed, the mixture was stirred for 30 min, and 100 ml of cold water was added and the precipitated compound was filtered, washed with cold water and dried in vacuo overnight at room temperature to give 2.7 g (67%) of the sub-title compound.

IR:(film) 2133.1,1669.95,1525.25,1466.04,1191.71

¹H-NMR:(CDCl₃): 7.85 (1H, dd); 7.85 (1H, s); 7.60 (1H, d); 7.4 (2H, m); 7.25 (1H, d); 7.15 (1H, q); 7.0 (1H, tt); 5.5 (2H, s)

e) 3-({5-Fluoro-3-[3-(5-fluoro-1-methyl-indol-3-yl)-5-oxo-1,5-dihydro-4H-1,2,4-triazol-4-yl]-indol-1-yl}methyl)benzonitril The product from d) (1.36 g, 9 mmol) was dissolved in 25 ml of toluene and the solution was heated at 90° C. for 6 h. The toluene was evaporated, and the crude isocyanate was dissolved in 35 mL of dry DMF and 0.86 g (9 mmol) of the hydrazide product of Example 11e) was added and the resulting mixture was stirred overnight. Triethylamine (4.84 mL. 36 mmol) was added followed by slow addition of trimethyl silyl triflate (6.5 mL, 36 mmol) which was injected with a syringe. The mixture was stirred under nitrogen at 80° C. overnight and poured into 500 mL of ice cold water. The formed precipitate was filtered with suction, washed with water and dried in vacuo at 40° C. overnight. Recrystallisation from TBME/MeOH afforded 0.97 g (56%) of the sub-title compound.

¹H-NMR (DMSO-d₆): 7.95 (1H, s); 7.70–7.60 (5H, m); 7.50 (2H, d); 7.45 (1H, m); 7.00 (3H, m); 6.85 (1H, s); 5.55 (2H, s); 3.55 (3H, s).

APCI-MS m/z: 481.1 [MH+].

A solution of 0.96 g (0.02 mmol) of the product from e) in 25 mL of dry methanol was saturated with a mild stream of hydrogen chloride gas under stirring and efficient cooling in ice-salt bath. Then, it was stirred overnight at room temperature, evaporated, dissolved in methanol (20 mL) and precipitated with ethyl acetate to give the title product as a pale yellow powder.

¹H-NMR (DMSO-d₆): 8.00 (1H, s); 7.65 (2H, m); 5.60 (1H, q); 7.50 (4H, m); 7.00 (3H, m); 6.55 (1H, s); 5.55 (2H, s); 3.50 (3H, s); 3.00 (3H, s).

APCI-MS m/z: 523.1 [MH+].

EXAMPLE 93

3-({5-Fluoro-3-[3-(5-fluoro-1-methyl-indol-3-yl)-5-oxo-1,5-dihydro-4H-1,2,4-triazol-4-yl]-indol-1-yl}methyl)-N,N-dimethylbenzenecarboximidamide hydrochloride

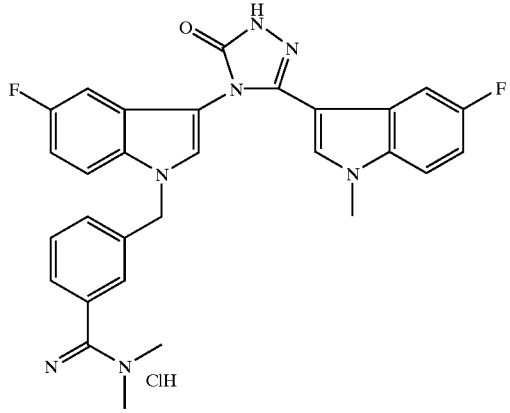

To a suspension of 90 mg (0.16 mmol) the product from Example 92 in abs. ethanol (5 ml) was added 3 mmol (7 mL) of dimethylamine (40% in ethanol) and the mixture was stirred and heated in a sealed tube at 80° C. overnight. The volatiles were evaporated and the crude was triturated with ethyl acetate. Purification via preparative HPLC (C-18 silica gel, MeCN/water cont.0.1% TFA, gradient 10–90% MeCN) and lyophilisation from 10 mL of HCl (3 N) gave the title compound.

¹H-NMR (DMSO-d₆): 12.00 (1H, s); 9.20 (1H, bs); 8.00 (1H, s); 7.75 (1H, dd), 7.55–7.45 (8H, m); 7.05 (1H, m); 6.85 (1H, s); 5.55 (2H, s); 3.70 (6H, s); 3.55 (3H, s).

APCI-MS m/z: 526.1 [MH+].

EXAMPLE 94

N-Benzyl-3-({5-fluoro-3-[3-(5-fluoro-1-methyl-indol-3-yl)-5-oxo-1,5-dihydro-4H-1,2,4-triazol-4-yl]-indol-1-yl}methyl)benzenecarboximidamide hydrochloride This compound was prepared according to the procedure of Example 93, starting from the product of Example 92 and 1.1 equivalents of benzylamine. ¹H-NMR (DMSO-d₆): 8.10 (1H, s); 8.05 (1H, s); 7.75 (3H, m); 7.25–7.35 (7H, m); 7.10 (4H, m); 6.85 (1H, s); 5.60 (2H, s); 4.80 (2H, s); 3.55 (3H, s).

APCI-MS m/z: 588.1 [MH+].

EXAMPLE 95

3-({5-Fluoro-3-[3-(5-fluoro-1-methyl-indol-3-yl)-5-oxo-1,5-dihydro-4H-1,2,4-triazol-4-yl]-indol-1-yl}methyl)benzenecarboximidamide hydrochloride This compound was prepared according to the procedure of Example 93, starting from the product of Example 92 and excess of ammonium hydroxide.

¹H-NMR (DMSO-d₆): 10.1 (1H, bs), 8.05 (1H, s); 8.00 (1H, s); 7.70 (2H, m); 7.60–7.50 (3H, m); 7.05 (3H, m); 6.85 (1H, s); 3.55 (3H,s); 5.50 (2H, s).

APCI-MS m/z: 499.0 [MH+].

EXAMPLE 96

4-(5-Fluoro-1-{3-[imino(4-morpholinyl)methyl]benzyl}-indol-3-yl)-5-(5-fluoro-1-methyl-indol-3-yl)-2,4-dihydro-3H-1,2,4-triazol-3-one hydrochloride This compound was prepared according to the procedure of Example 93, starting from the product of Example 92 and 1.1 equivalents of morpholine.

$^1$H-NMR (MeOD+TFA): 8.60 (1H, s); 8.55 (1H, s); 8.05 (2H, m); 7.85 (3H, m); 7.25 (3H, m); 7.15 (1H, s); 5.55 (2H, s); 4.00 (4H, m), 3.75–3.65 (4H, m); 3.50 (3H, s).

APCI-MS m/z: 569.2 [MH+].

EXAMPLE 97

3-({5-Fluoro-3-[3-(5-fluoro-1-methyl-indol-3-yl)-5-oxo-1,5-dihydro-4H-1,2,4-triazol-4yl]-indol-1-yl}methyl)-N-isopropylbenzenecarboximidamide hydrochloride This compound was prepared according to the procedure of Example 93, starting from the product of Example 92 and 1.1 equivalents of isopropyl amine.

$^1$H-NMR (DMSO-$d_6$): 8.05 (1H, s); 7.85 (2H, m); 7.50 (3H, m); 7.45 (2H, m); 7.05 (4H, m); 6.85 (1H, s); 5.50 (2H, s); 4.05 (1H, m); 3.50 (3H, s); 3.35 (1H, bs); 1.25 (6H, d).

APCI-MS m/z: 540.1 [MH+].

EXAMPLE 98

N-(3-{5-Fluoro-3-[3-(5-fluoro-1-methyl-indol-3-yl)-5-oxo 1,5-dihydro-4H-1,2,4-triazol-4-yl]-indol-1-yl}propyl)guanidine trifluoroacetate To a solution of the product from Example 2 (0.12 g, 0.248 mmol) in absolute ethanol were added 1-formamidino-3,5-dimethylpyrazole (0.06 g, 0.30 mmol) and sodium hydrogensulfate (0.05 g, 1.7 mmol) and the resulting mixture was stirred overnight at 50° C. After evaporation of the solvent, the crude was dissolved in methanol and the solution was acidified with TFA to pH around 2. The acidic solution was subjeted to preparative HPLC (C-18 silica gel, MeCN/water cont.0.1% TFA, gradient 10–90% MeCN). Lyophilisation from water gave 37 mg of the title compound.

$^1$H-NMR (CD$_3$OD): 8.10 (1H, m); 7.55 (1H, dd); 7.45 (2H, m); 7.22 (1H, m); 6.90 (2H, m); 6.60 (1H, s); 4.30 (2H, t); 3.15 (3H, s); 2.10 (2H, t); 1.10 (2H, t).

APCI-MS ml/z: 465.1 [MH+].

EXAMPLE 99

4-{5-Fluoro-3-[3-(5-fluoro-1-methyl-indol-3-yl)-5-oxo-1,5-dihydro-4H-1,2,4-triazol-4-yl]-indol-1-yl}butanenitrile To a solution of the product from Example 18 (0.86 g, 1.77 mmol) in dry DMF (25 mL) was added potassium cyanide (0.18 g, 2.77 mmol) and the mixture was stirred and heated at 50° C. overnight under nitrogen. The solvent was evaporated, and the residue was distributed between ethyl acetate and water. The water phase was extracted twice with ethyl acetate, and the combined organic phases were washed with water and dried. After evaporation the crude product was chromatographed on silica gel (EtOAc) to yield 0.46 g (61%) of the title product.

$^1$H-NMR (CD$_3$OD): 8.10 (1H, s); 7.55 (1H, m); 7.45 (1H, m); 7.11 (2H, m); 7.00 (2H, m); 6.60 (1H, s); 4.11 (3H, s); 3.55 (2H, t); 2.55 (2H, t), 2.00 (2H, m).

APCI-MS m/z: 432.1 [MH+].

EXAMPLE 100

4-{5-Fluoro-3-[3-(5-fluoro-1-methyl-indol-3-yl)-5-oxo-1,5-dihydro-4H-1,2,4-triazol-4-yl]-indol-1-yl}-N,N-dimethylbutanimidaniide hydrochloride

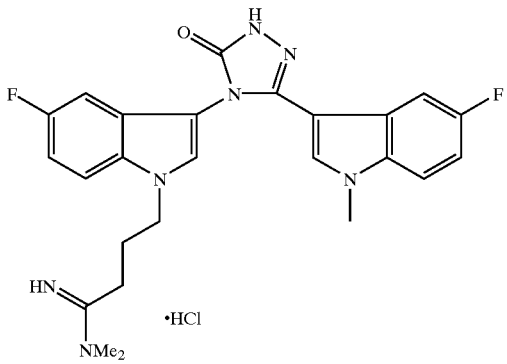

A cooled and stirred suspension of the product from Example 99 in dry methanol was saturated with HCl gas. Then, the mixture was stirred overnight, the solvent was evaporated and the remaining dried in vacuo for 3 h. This was dissolved in 10 mL of methanol, and 10 mL of dimethylamine (40% in metanol) was added. The mixture was heated in a sealed tube with stirring overnight at 80° C. After cooling and evaporation, the residue was purified by preparative HPLC (C-18 silica gel, acetonitrile /water cont. 0.1% TFA, gradient 10–90% acetonitrile). Lyophilisation from water gave the title compound.

$^1$H-NMR (CD$_3$OD): 8.00 (1H, s); 7.60 (1H, m); 7.50 (2H, m); 7.35 (1H, m); 7.1 (2H, m); 6.56 (1H, s); 3.55 (3H, s); 3.10 (3H, s); 3.15 (3H, s); 2.95 (2H, t), 2.55 (2H, t); 2.1 (2H, m);

APCI-MS rn/z: 479.1 [MH+].

EXAMPLE 101

5-(5-Fluoro-1-methyl-indol-3-yl)-4-{1-[1-(2,2,2-trifluoro-ethyl)-piperidin-4-yl]-indol-3-yl}-2,4-dihydro-[1,2,4]triazol-3-one $^1$H NMR (400 MHz, DMSO-$d_6$): δ11.91 (1H, s); 7.92 (1H, s); 7.77 to 7.71 (2H, m); 7.45 (1H, dd, J 9.1 and 4.5 Hz); 7.25 to 7.21 (2H, m); 7.11 to 7.03 (2H, m); 6.58 (1H, s); 4.54 (1H, m); 3.54 (3H, s); 3.32–3.24 (2H, m); 3.10 to 3.05 (2H, m); 2.77 to 2.64 (2H, m); 2.08 to 1.97 (4H, m).

APCI-MS m/z: 513 [MH+].

EXAMPLE 102

4-[1-(3-Aminopropyl)-5-fluoro-indol-3-yl]-5-(5-bromo-pyridin-3-yl)-2,4-dihydro-[1,2,4]triazol-3-one hydrochloride The title compound was prepared by the method described in Example 45 starting from the product of Example 45d) and 5-bromo-nicotinic acid hydrazide.

$^1$H NMR (400 MHz, DMSO-$d_6$): δ12.45 (1H, s); 8.68 (1H, d); 8.48 (1H, d); 8.00 (1H, m); 7.89 (3H, bs); 7.80 (1H, s); 7.70 (1H, m); 7.16 to 7.09 (2H, m); 4.35 (2H, m); 2.75 (2H, m); 2.04 (2H, m).

APCI-MS m/z: 431 [MH+].

EXAMPLE 103

4,5-Bis-[1-(3-Aminopropyl)-5-fluoro-indol-3-yl]-2,4-dihydro-[1,2,4]triazol-3-one dihydrochloride The title compound was prepared by the method described in Example 6.

$^1$H NMR (400 MHz, DMSO-$d_6$): δ11.97 (1H, s); 8.07 (3H, bs); 7.92 (3H, bs); 7.86 (1H, s); 7.76 to 7.72 (2H, m); 7.61 (1H, dd, J 9.1 and 4.5 Hz); 7.15 to 7.09 (2H, m); 7.00 (1H, dd, J 9.3 and 2.4 Hz); 6.80 (1H, s); 4.41 (2H, m); 4.11 (2H, m); 2.81 (2H, m); 2.57 (2H, m); 2.12 (2H, m); 1.80 (2H, m).

APCI-MS m/z: 466 [MH+].

EXAMPLE 104

4-{1-[2-(2-Aminoethoxy)-ethyl]-5-fluoro-indol-3-yl}-5-(5-fluoro-1-methyl-indol-3-yl)-2,4-dihydro-[1,2,4]triazol-3-one hydrochloride The title compound was prepared essentially as described in Example 44. The final ring closure and deprotection were performed as described for Example 66.

$^1$H NMR (400 MHz, DMSO-$d_6$): δ11.97 (1H, s); 7.86 (1H, s); 7.90 to 7.66 (5H); 7.47 (1H, dd, J 8.9 and 4.5 Hz); 7.13 to 7.06 (2H, m); 7.00 (1H, dd, J 9.4 and 2.5 Hz); 6.70 (1H, s); 4.48 (2H, m); 3.80 (2H, m); 3.57 (3H, s); 3.55 (2H, m); 2.89 (2H, m).

APCI-MS m/z: 453 [MH+].

EXAMPLE 105

3-(3-{5-Fluoro-3-[3-(5-fluoro-1-methyl-indol-3-yl)-5-oxo-1,5-dihydro-[1,2,4]triazol-4-yl]-indol-1-yl}-propylamino)-propionic acid methyl ester hydrochloride The title compound was prepared by the method described in Example 24.

$^1$H NMR for the amine (400 MHz, DMSO-$d_6$): δ11.91 (1H, s); 7.75 (1H, s); 7.72 (1H, dd, J 10.1 and 2.5 Hz); 7.68 (1H, dd, J 9.1 and 4.3 Hz); 7.47 (1H, dd, J 9.0 and 4.4 Hz); 7.12–7.06 (2H, m); 7.02 (1H, dd, J 9.4 and 2.5 Hz); 6.67 (1H, s); 4.30 (2H, m); 3.57 (6H, 2s); 2.68 (2H, m); 2.50 to 2.38 (4H, m); 1.90 (2H, m).

APCI-MS m/z: 509 [MH+].

EXAMPLE 106

3-(3-{5-Fluoro-3-[3-(5-fluoro-1-methyl-indol-3-yl)-5-oxo-1,5-dihydro-[1,2,4]triazol-4-yl]-indol-1-yl}-propylamino)-propionic acid trifluoro acetic acid salt The title compound obtained in Example 105 (193 mg, 0.38 mmol) was stirred in aqueous sodium hydroxide (25%, 13 mL) and ethanol (1.5 mL) at 90 for 1.5 h. Trifluoro acetic acid was added and the mixture was evaporated. The residue was purified by preparative HPLC and lyuphilised to give 171 mg (74%) of the title product.

$^1$H NMR (400 MHz, DMSO-$d_6$): δ12.80 (1H, bs); 11.94 (1H, s); 8.55 (2H, bs) 7.81 (1H, s); 7.75 (1H, dd, J 10.1 and 2.5 Hz); 7.73 (1H, dd, J 9.1 and 4.3 Hz); 7.48 (1H, dd, J 9.0 and 4.4 Hz); 7.16 to 7.07 (2H, m); 7.04 (1H, dd, J 9.3 and 2.5 Hz); 6.73 (1H, s); 4.36 (2H, m); 3.59 (3H, s); 3.12 (2H, m); 2.97 (2H, m); 2.64 (2H, m); 2.14 (2H, m).

MS-LSIMS+: m/z: 495 [MH+].

EXAMPLE 107

1-(3-Aminopropyl)-3-[3-(5-fluoro-1-methyl-indol-3-yl)-5-oxo-1,5-dihydro-[1,2,4]triazol-4-yl]-1-indole-5-carbonitrile hydrochloride The title compound was prepared by the method described in Example 66.

$^1$H NMR (400 MHz, DMSO-$d_6$): δ11.99 (1H, s); 8.05 (3H, bs) 8.01 (1H, s); 7.96 (1H, d, J 8.7 Hz); 7.91 (1H, bs); 7.75 (1H, dd, J 10.1 and 2.5 Hz); 7.65 (1H, dd, J 8.7 and 1.4 Hz); 7.48 (1H, dd, J 9.0 and 4.6 Hz); 7.10 (1H, ddd, J 11.6, 9.0 and 2.5 Hz); 6.74 (1H, s); 4.46 (2H, m); 3.60 (3H, s); 2.79 (2H, m); 2.12 (2H, m).

MS-LSIMS+: m/z: 430 [MH+].

EXAMPLE 108

2-(3-Amninopropyl)-4-[1-(3-amino-propyl)-5-fluoro-indol-3-yl]-5-(5-fluoro-1-methyl-indol-3-yl)-2,4-dihydro-[1,2,4]triazol-3-one dihydrochloride a) 4-[1-(3-Azido-propyl)-5-fluoro-indol-3-yl]-5-(5-fluoro-1-methyl-indol-3-yl )-2,4-dihydro-[1,2,4]triazol-3-one Title compound 18 (580 mg, 1.19 mmol) and sodium azide (117 mg, 1.79 mmol) was stirred in DMF (5 mL) at 70° C. for 0.5 hours. Ethyl acetate was added and the organic phase was washed with water, brine, dried and concentrated in vacuo. The solid residue was crystallized from ethyl acetate to give 460 mg (95%) of the sub-title compound.

$^1$H NMR (400 MHz, DMSO-$d_6$): δ11.92 (1H, bs)7.79 (1H, s); 7.73 to 7.67 (2H, m); 7.47 (1H, m); 7.15 to 7.01 (3H); 6.76 (1H,s); 4.33 (2H, m); 3.58 (3H, s); 2.49 (2H, m);2.05 (2H, m).

APCI-MS m/z: 449 [MH+].

b) {3-[4-[1-(3-Azido-propyl)-5-fluoro-indol-3-yl]-3-(5-fluoro-1-methyl-indol-3-yl)-5-oxo-4,5-dihydro-[1,2,4]triazol-1-yl]-propyl}-carbamic acid tert-butyl ester Sub-title compound a) (100 mg, 0.22 mmol), (3-bromopropyl)-carbamic acid tert-butyl ester (80 mg, 0.34 mmol) and potassium carbonate (61 mg, 0.44 mmol) were stirred in DMF (2 mL) at 70° C. for 2 hours. The mixture was diluted with ethyl acetate, washed with water, brine and concentrated in vacuo. Silica gel cromatography (ethyl acetate-toluene, 3:1) gave 116 mg (87%) of the sub-title compound.

$^1$H NMR (400 MHz, DMSO-$d_6$): δ7.82 (1H, s); 7.77 (1H, dd, J 9.9 and 2.5 Hz); 7.70 (1H, dd, J 8.9 and 4.3 Hz); 7.48 (1H, dd, J 9.0 and 4.4 Hz); 7.15 to 7.07 (3H); 6.90 (1H, bs); 6.76 (1H, s); 4.34 (2H, m); 3.85 (2H, m); 3.59 (3H, s); 3.31(2H, m); 3.09 (2H, m); 2.06 (2H, m); 1.94 (2H, m); 1.38 (9H, s).

APCI-MS m/z: 606.5 [MH+].

c) {3-[4-[1-(3-Amino-propyl)-5-fluoro-indol-3-yl]-3-(5-fluoro-1-methyl-indol-3-yl)-5-oxo-4,5-dihydro-[1,2,4]triazol-1-yl]-propyl}-carbamic acid tert-butyl ester Sub-title compound b) (107 mg, 0.18 mmol), triphenylphosphine (232 mg, 0.88 mmole) and water (32 μL, 1.77 mmol) were stirred in THF (4 mL) at room temperature over night. Aqueous ammonium hydroxide (25%, ~0.1 mL) was added, the mixture was stirred for 0.5 hours and concentrated in vacou. Silica gel chromatography (dichloromethane-methanol-ammonium hydroxide, 25% in water, 100:10:1) gave 66 mg (65%) of the sub-title compound.

APCI-MS m/z: 580 [MH+].

Sub-title compound c) was dissolved in acetonitrile/water (1:1, 5 mL). Hydrochloric acid (approx. 50 μL) was added and the solution was stirred at 70° C. for 0.5 hours. The mixture was concentrated in vacou, dissolved in water and lyophilized.

¹H NMR (400 MHz, DMSO-d₆): δ8.30 (3H, bs); 8.15 (3H, bs); 7.94 (1H, s); 7.84 (1H, dd, J 10.0 and 2.6 Hz); 7.79 (1H, dd, J 9.1 and 4.3 Hz); 7.50 (1H, dd, J 9.1 and 4.5 Hz); 7.16 to 7.09 (2H, m); 7.07 (1H, dd, J 9.3 and 2.5 Hz); 6.68 (1H, s); 4.42 (2H, m); 3.96 (2H, m); 3.60 (3H, s); 2.97 (2H, m); 2.78 (2H, m); 2.15 (4H, m).

APCI-MS m/z: 480 [MH+].

EXAMPLE 109

4-[1(S)-(3(S)-Diethylamino-cyclopentyl)-5-fluoro-indol-3-yl]-5-(5fluoro-1-methyl-indol-3-yl)-2,4-dihydro-[1,2,4]triazol-3-one trifluoroacetate The product from Example 3 (29.0 mg, 60.0 μmol) was dissolved in 1 mL methanol and applied on a 30 mL silica column. The free base was eluted with ammonia-saturated methylene chloride-methanol (6:1) to yield 24.6 mg (57 μmol) upon evaporation. This was dissolved in trimethylorthoformate-dimethylformamide (2 mL, 3:1), acetaldehyde (32 μl, 570 μmol) and sodium cyanoborohydride (18 mg, 285 μmol) and the resulting mixture was stirred at room temperature for 1 h. After evaporation, the residue was run through a silica column and the free base was eluted with ammonia-saturated methylene chloride-methanol (6:1). The crude product resulting from the evaporation of the eluates was subjected to purification by HPLC (C-18, 0.1% trifluoroacetic acid in methanol-water 35:65) to yield 15.7 mg (42%) of the title product.

¹H-NMR (400 MHz, CD₃OD): δ7.80 (1H, s); 7.76 (1H, dd J 2.4 and 9.9 Hz); 7.67 (1H, dd, J 4.1 and 9.0 Hz); 7.39 (1H, dd, J 4.1 and 8.7 Hz); 7.13 (1H, dt, J 2.3 and 9.0 Hz); 7.09–7.00 (2H, m); 6.73 (1H, s); 5.29 (1H, sym.m. J 7.5 Hz); 4.11–4.02 (1H, m); 3.61 (3H, s); 3.53–3.39 (1H, m); 3.25–3.12 (1H, m); 2.96–2.90 (2H, m); 2.65–2.43 (3H, m); 2.26–2.17 (1H, m); 2.07–1.98 (1H, m); 1.49–1.29 (6H, m).

APCI-MS m/z: 505.3[MH+].

EXAMPLE 110

4-[1-(3-Bromopropyl)-5-fluoro-indol-3-yl]-5-(1-H-indol-3-yl)-2,4-dihydro-[1,2,4]triazol-3-one Triphenylphosphine (0.168, 0.64 mmol) was added to a mixture of 4-[1-(3-hydroxy-propyl)-5-fluoro-indol-3-yl]-5-(1-H-indol-3-yl)-2,4-dihydro-[1,2,4]triazol-3-one (0.23 g 0.59 mmol), synthesised in accordance to the procedure for Example 1, triphenylphosphine (0.168 g, 0.64 mmol) and tetrabromomethane (0.218 g, 0.66 mmol) in dry THF (15 ml). The resulting mixture was stirred at ambient temperature. After 16 h the LCMS showed that some starting material still was left. Additional tetrabromomethane (0.198 g, 0,60 mmol) and triphenylphosphine (0.158 g, 0.60 mmol) were added and the solution was allowed to proceed for 20 h more at ambient temperature. Evaporation and silica gel chromatography (dichloromethane/methanol, gradient to 100/5) afforded 0.165 g (57%) of the title compound as a white solid.

¹H NMR (400 MHz, DMSO-d₆): δ11.87 (1H, s); 11.20 (1H, s); 8.07 (1H, d); 7.81 (1H, s); 7.70 (1H, dd); 7.37 (1H, d); 7.18–7.08 (3H, m); 7.02 (1H, dd); 4.39 (2H, t); 3.45 (2H, t); 2.34 (2H, p).

APCI-MS m/z: 456.1 [MH+].

EXAMPLE 111

4-[1-(3-Cyanopropyl)-5-fluoro-indol-3-yl]-5-(1-H-indol-3-yl)-2,4-dihydro-[1,2,4]triazol-3-one hydrochloride Potassium cyanide (0.040 g, 0.614 mmol), dissolved in a small amount of water, was added to the product of Example 110 (0.052 g, 0.114 mmol) in THF (3.0 mL) and the solution was stirred for 16 h at 50° C. Evaporation and silica gel chromatography (dichloromethane/methanol, gradient to 100/5) afforded 0.014 g (31%) of the title compound as a white solid.

¹H NMR (400 MHz, DMSO-d₆): δ11.87 (1H, s); 11.18 (1H, s); 8.07 (1H, d); 7.82 (1H, s); 7.70 (1H, dd); 7.37 (1H, d); 7.18–7.08 (3H, m); 7.01 (1H, dd); 6.67 (1H, dd); 4.33 (2H, t); 2.48 (2H, t); 2.12 (2H, p).

LCI-MS m/z: 401.2 [MH+]

EXAMPLE 112

4-[1-(3-Aminopropyl)-5-fluoro-indol-3-yl]-5-(1-H-indol-3-yl)-2,4-dihydro-[1,2,4]triazol-3-one trifluoroacetate Sodium azide (0.014 g, 0.215 mmol) was added to the product of Example 110 (0.053 g, 0.116 mmol) in THF (3.5 mL) and water (0.35 mL) to afford a solution which was heated at reflux for 6 h. Evaporation, followed by azeotropic destillation with some THF, afforded a dry residue. This was dissolved in dry pyridine (5.0 mL) together with triphenylphosphine (0.114 g, 0.435 mmol). After stirring at ambient temperature for 10 min, 25% NH₃ (aq) (1.0 mL) was added, and the resulting mixture stirred for another 16 h. Evaporation followed by silica gel chromatography (dichloromethane/methanol/25% NH₃ (aq), gradient to 30/70/2) afforded the title compound as the free base. This was dissolved in methanol together with trifluoroacetic acid (0.100 mL, 1.30 mmol). Evaporation, followed by addition of water and lyophilisation furnished 29 mg (50%) of the title compound as a white solid.

¹H NMR (400 MHz, DMSO-d₆): δ11.88 (1H, s); 11.18 (1H, s); 8.10 (1H, d);7.83 (1H, s); 7.77 (3H, bs); 7.73 (1H, dd); 7.38 (1H, d); 7.25–6.99 (3H, m); 7.03 (1H, dd); (1H, dd); 6.54 (1H,dd); 4.37 (2H, t); 2.80 (2H, m); 2.08 (2H, p).

ESI-MS m/z: 391.1 [MH+].

EXAMPLE 113

4-[1-(3-(-(4-Methyl-1-piperazinyl))-5-fluoro-indol-3-yl]-5-(1-H-indol-3-yl)-2,4-dihydro-[1,2,4]triazol-3-one dihydrochloride 1-Methyl-piperazine (0.068 g, 0.677 mmol) and the product of Example 110 (0.0615, 0.135 mmol) was heated at reflux in THF (5.0 mL) for 5 h. Evaporation and chromatography on silica (dichloromethane/methanol/25% NH₃ (aq), 100/10/1) afforded 0.037 g (50%), of the title compound as a white solid.

¹H NMR (400 MHz, DMSO-d₆): δ11.88 (1H, s); 11.27 (1H, s); 8.11 (1H, d); 7.84 (1H, s); 7.76 (1H, dd); 7.40 (1H, d); 7.17 (1H, t); 7.15–7.10 (2H, m); 7.03 (1H, dd); 6.62 (1H, dd); 4.39 (2H, m); 3.63–3.08 (9H, broad m); 2.81 (4H, bs); 2.22 (2H, broad m).

APCI-MS m/z: 474.3 [MH+].

EXAMPLE 114

4-[5-Fluoro-1-(3-hydroxypropyl)-indol-3-yl]-5-(1-iso-propyl-indol-3-yl)-2,4-dihydro-[1,2,4]triazol-3-one The title compound was synthesised using the same method as for the synthesis of the product of Example 1.

¹H NMR (400 MHz, DMSO-d₆): δ11.87 (1H, s); 8.10 (1H, d); 7.82 (1H, s); 7.68 (1H, dd); 7.49 (1H, d); 7.21 (1H, t); 7.15 (1H, t); 7.09 (1H, dt); 6.94 (1H, dd); 6.56 (1H, s); 4.67 (1H, t); 4.57 (1H, p); 4.34 (2H, t); 3.41 (2H, q); 194 (2H, p); 1.01 (6H, d).

APCI-MS mn/z: 434.1 [MH+]

EXAMPLE 115

4-(1-Methyl-1H-indol-3-yl)-5-(8-aminomethyl-6,7,8, 9-tetrahydro-pyrido[1,2a ]indol-10-yl)-2,4-dihydro-[1,2,4]triazol-3-one hydro chloride a) 8-Azidomethyl-6,7,8,9-tetrahydro-pyrido[1,2-a ]indole-10-carboxylic hydrazide Caution! The by-product of this synthesis, the hydrazin azide salt, is an explosive and should not be isolated or concentrated!

Hydrazine hydrate (0.445 mL, 9.20 mmol) was added to the product of Example 13a) (0.655 g, 2.218 mmol) in THF (10 mL). The mixture was stirred at ambient temperature for 16 hours, then partitioned between ethyl acetate (30 mL) and water (50 mL). The aqueous phase was extracted twice with ethylacetate. The pooled organic phases were evaporated to obtain 0.640 g (99%) of the sub-title compound.

$^1$H NMR (400 MHz, DMSO-$d_6$): δ8.65 (1H, s); 7.80 (1H, d); 7.40 (1H, d); 7.14 (1H, t); 7.11 (1H, t); 4.45 (2H, bs); 4.34 (1H, m); 3.90 (1H, dt); 3.52 (2H, d); 3.43 (1H, dd); 2.78 (1H, dd); 2.20–2.05 (2H, m); 1.80–1.70 (1H, m); 1.65 (1H,m).

APCI-MS m/z: 285.1 [MH+]

b) 4-(1-Methyl-1H-indol-3-yl)-5-(8-azidomethyl-6,7,8,9-tetrahydro-pyrido[1.2-a ]indol-10-yl)-2,4-dihydro-[1,2,4] triazol-3-one 1-Methyl-1-H-indole-3-carbonyl azide (0.222 g, 1.109 mmol) was stirred in dry toluene (10 mL) at 130° C. for two hours. Evaporation afforded a oil (0.189 g). To this oil was added the product of a) (0.315, 1.10 mmol) dissolved in dry DMF (10 ML) and the solution was stirred for 15 min at room temperature. Triethylamine (0.775 mL, 5.56 mmol) followed by trimethylsilyl triflate (1.000 mL, 5.53 mmol) were added and the resulting mixture was heated under stirring at 130° C. for 5 h. The solution was poured into water (150 mL). Filtration and silica gel chromatography (dichloromethane-methanol, gradient from 100/1 to 100/5) afforded 0.121 g (25% ) of the sub-title compound.

$^1$H NMR (400 MHz, DMSO-$d_6$): δ11.96 (1H, s); 7.46 (1H, s); 7.39 (1H, d); 7.29 (1H, d); 7.27 (1H, dd); 7.16 (1H, d); 7.12 (1H, t); 7.01 (1H, t); 6.94(1H, t); 6.87 (1H, t); 4.22 (1H, m); 3.80 (1H, dt); 3.70 (3H, s); 3.35 (1H, d); 3.09 (1H, m); 3.02 (1H, dd); 2.34 (1H, dd); 2.07 (1H,d); 1.91 (1H, m); 1.65 (1H,m).

APCI-MS m/z: 439.3 [MH+]

The product of b) (0.110 g, 0.251 mmol) and triphenylphosphine (0.328 g, 1.254 mmol) was stirred in pyridine (10 mL) for one hour at room temperature. Ammonia (aq, 25%) (3 mL) was added and the mixture was stirred for additional 16 h. Evaporation and silica gel chromatography (dichlorometane-methanol/25% NH$_3$ (aq), 90/10/2) afforded 0.063 g of the title compound in the form of the free base. This was dissolved in water (50 mL) together with 10 M HCl (1 mL). Lyophilisation furnished 0.069 g (67%) of the title product as a white solid.

$^1$H NMR (400 MHz, DMSO-$d_6$): δ11.99 (1H, s); 8.16 (3H, bs); 7.57 (1H, s); 7.37 (1H, d); 7.28 (1H, d); 7.24 (1H, d); 7.19 (1H, d); 7.10 (1H, t); 7.00 (1H, t); 6.96 (1H, t); 6.86 (1H, t); 4.29–4.22 (1H, m); 3.79 (1H, dt); 3.71 (3H, s); 3.20 (2H, dd); 2.83 (2H, p); 2.21 (1H, m); 2.11 (1H, m); 1.70 (1H, m).

LSIMS+ m/z: 413.3 [MH]+

The products of Example 116 through Example 133 were prepared analogously to Example 66, starting from the product of Example 45 c) and the appropriate hydrazide.

EXAMPLE 116

4-[1-(3-Aminopropyl)-5-fluoro-indol-3-yl]-5-(2-quinolinyl)-2,4-dihydro-[1,2,4]triazol-3-one dihydrochloride $^1$H NMR (400 MHz, DMSO-$d_6$): δ12.47 (1H, s); 8.41 (1H, d); 8.12 (3H, bs); 7.96 (1H, dd); 7.93 (1H, t); 7.81 (1H, s); 7.68 (1H, dd); 7.65 (1H, t); 7.56 (1H, t); 7.23 (1H, d); 7.04 (1H, dt); 6.99 (1H, dd); 4.38 (2H, t); 2.78 (2H, h); 2.09 (2H, p).

LSI-MS m/z: 403.1 [MH+]

EXAMPLE 117

4-[1-(3-Aminopropyl)-5-fluoro-indol-3-yl]-5-(2-naphtyl)-2,4-dihydro-[1,2,4]triazol-3-one hydrochloride $^1$H NMR (400 MHz, DMSO-$d_6$): δ12.24 (1H, s); 8.04 (3H, bs); 7.98 (1H, s); 7.87–7.83 (3H, m); 7.73–7.68 (2H, m); 7.55–7.48 (3H, m); 7.10–7.02 (2H, m); 4.36 (2H, t); 2.74 (2H, h); 2.06 (2H, p).

LSI-MS m/z: 402.1 [MH+]

EXAMPLE 118

4-[1-(3-Aminopropyl)-5-fluoro-indol-3-yl]-5-phenyl-2,4-dihydro-[1,2,4]triazol-3-one hydrochloride $^1$H NMR (400 MHz, DMSO-$d_6$): δ12.15 (1H, bs); 8.02 (3H, bs); 7.76 (1H, s); 7.68 (1H, dd); 7.40–7.28 (4H, m); 7.09 (1H, dt); 7.01 (1H, dd); 4.34 (2H, t); 2.70 (2H, m); 2.04 (2H, p).

LSI-MS m/z: 352.0 [MH+]

EXAMPLE 119

4-[1-(3-Amino-propyl)-5-fluoro-indol-3-yl]-5-(4-biphenyl)-2,4-dihydro-[1,2,4]triazol-3-one hydrochloride $^1$H NMR (400 MHz, DMSO-$d_6$): δ12.18 (1H, bs); 8.11 (3H, bs); 7.83 (1H, s); 7.71 (1H, dd); 7.65–7.62 (4H, m); 7.50 (1H, s); 7.49 (1H, d); 7.43 (1H, t) 7.35 (1H, t); 7.13–7.05 (2H, m); 4.37 (2H, t); 2.74 (2H, m); 2.06 (2H, 9);

LSI-MS m/z: 428.1 [MH+]

EXAMPLE 120

4-[1-(3-Aminopropyl)-5-fluoro-indol-3-yl]-5-(4-phenoxy-phenyl)-2,4-dihydro-[1,2,4]triazol-3-one hydrochloride $^1$H NMR (400 MHz, DMSO-$d_6$): δ12.11 (1H, s); 7.94 (3H, bs); 7.79 (1H, s); 7.68 (1H, dd); 7.41–7.36 (4H, m); 7.16 (1H, t); 7.10 (1H, t); 6.99 (3H, d); 6.89 (2H, d); 4.35 (2H,t);2.73 (2H, m); 2.04 (2H, p).

ESI-MS m/z: 444.1 [MH+]

EXAMPLE 121

4-[1-(3-Aminopropyl)-5-fluoro-indol-3-yl]-5-(1-ethoxy-phenyl-3-yl)-2,4-dihydro-[1,2,4]triazol-3-one trifluoroacetate $^1$H NMR (400 MHz, DMSO-$d_6$): δ12.15 (1H, s); 7.80 (2H, bs); 7.72 (1H, s); 7.66 (1H, dd); 7.18 (1H, t); 7.11 (1H, dt); 7.06 (1H, dd); 6.95–6.87 (3H, m); 4.31 (2H, t); 3.73 (2H, q); 2.76 (2H, t); 2.02 (2H, p); 1.13 (3H, t).

APCI-MS: m/z 396.1 [MH+]

EXAMPLE 122

4-[1-(3-Aminopropyl)-5-fluoro-indol-3-yl]-5-(4-phenyl-1-methyl-pyrrole-3-yl)-2,4-dihydro-[1,2,4]triazol-3-one trifluoroacetate $^1$H NMR (400 MHz, DMSO-d$_6$): δ11.82 (1H, s); 7.77 (3H, bs); 7.46 (1H, dd); 7.21–7.17 (2H, m); 7.08 (1H, tt); 7.02–6.94 (4H, m); 6.88 (1H, s); 6.83 (1H, d); 6.73 (1H, dd); 4.10 (2H, t); 3.56 (3H, s); 2.70 (2H, m); 1.90 (2H, p).

APCI-MS m/z: 431.2 [MH+]

EXAMPLE 123

4-[1-(3-Aminopropyl)-5-fluoro-indol-3-yl]-5-(5-ethyl-1-methyl-indol-3-yl)-2,4-dihydro-[1,2,4]triazol-3-one trifluoroacetate $^1$H NMR (400 MHz, DMSO-d$_6$): δ11.87 (1H, s); 7.84 (1H, s); 7.77 (1H, s); 7.75 (2H, bs); 7.72 (1H, dd); 7.33 (1H, d); 7.13 (1H, dt); 7.08 (1H, dd); 7.03 (1H, dd); 6.62 (1H, s); 4.45 (2H, t); 3.54 (3H, s); 2.77 (2H, m); 2.66 (2H, q); 2.06 (2H, p); 1.17 (3H, t).

EXAMPLE 124

4-[1-(3-Aminopropyl)-5-fluoro-indol-3-yl]-5-(5-chloro-1-methyl-indol-3-yl)-2,4-dihydro-[1,2,4]triazol-3-one trifluoroacetate $^1$H NMR (400 MHz, DMSO-d$_6$): δ11.96 (1H, s); 8.08 (1H, d); 7.82 (1H, s); 7.80 (2H, bs); 7.73 (1H, dd); 7.50 (1H, d); 7.26 (1H, dd); 7.14 (1H, dt); 7.05 (1H, dd); 6.69 (1H, s); 4.37 (2H, t); 3.58 (3H, s); 2.80 (2H, bs); 2.09 (2H, p).

APCI-MS m/z: 439.1 [MH+]

EXAMPLE 125

4-[1-(3-Aminopropyl)-5-fluoro-indol-3-yl]-5-(5-methoxy-1-methyl-indol-3-yl)-2,4-dihydro-[1,2,4]triazol-3-one trifluoroacetate $^1$H NMR (400 MHz, DMSO-d$_6$): δ11.88 (1H, s); 7.77 (1H, s); 7.74 (2H, bs); 7.72 (1H, dd); 7.48 (1H, d); 7.34 (1H, d); 7.14 (1H, dt); 7.06 (1H, dd); 6.86 (1H, dd); 6.63 (1H, s); 4.35 (2H, t); 3.68 (3H, s); 3.54 (3H, s); 2.77 (2H, m); 2.06 (2H, p).

APCI-MS m/z: 435.3 [MH+]

EXAMPLE 126

4-[1-(3-Aminopropyl)-5-fluoro-indol-3-yl]-5-(1,2-dimethyl-indol-3-yl)-2,4-dihydro-[1,2,4]triazol-3-one trifluoroacetate $^1$H NMR (400 MHz, DMSO-d$_6$): δ11.97 (1H, s); 7.66 (2H, bs); 7.55 (1H, s); 7.47 (1H, dd); 7.32 (1H, d); 7.22 (1H, d); 7.02–6.93 (2H, m); 6.90 (1H, dd); 6.84 (1H, dt); 4.15 (2H, t); 3.59 (3H, s); 2.57 (2H, m); 2.28 (3H, s); 1.85 (2H, p).

EXAMPLE 127

4-[1-(3-Aminopropyl)-5-fluoro-indol-3-yl]-5-(6-methoxy-1-methyl-indol-3-yl)-2,4-dihydro-[1,2,4]triazol-3-one trifluoroacetate $^1$H NMR (400 MHz, DMSO-d$_6$): δ11.87 (1H, s); 7.95 (1H, d); 7.81 (1H, s); 7.77 (1H, s); 7.73 (1H, dd); 7.13 (1H, dt); 7.02 (1H, dd); 6.96 (1H, dd); 6.79 (1H, dd); 6.47 (1H, s); 4.37 (2H, t); 3.79 (3H, s); 3.51 (3H, s); 2.80 (2H, m); 2.09 (2H, p).

EXAMPLE 128

4-[1-(3-Aminopropyl)-5-fluoro-indol-3-yl]-5-(1,5-dimethyl-indol-3-yl)-2,4-dihydro-[1,2,4]triazol-3-one hydrochloride $^1$H NMR (400 MHz, CD$_3$OD): δ7.85 (1H, bs); 7.65 (1H, dd); 7.62 (1H, s); 7.27 (1H, d); 7.15–7.10 (2H, m); 7.04 (1H, dd); 6.67 (1H, s); 4.44 (2H, t); 3.78–3.75 (2H, m); 3.57 (3H, s); 2.95 (2H, t); 2.43 (3H, s); 2.27–2.20 (2H, m).

EXAMPLE 129

4-[1-(3-Aminopropyl)-5-fluoro-indol-3-yl]-5-(1-propyl-indol-3-yl)-2,4-dihydro-[1,2,4]triazol-3-one hydrochloride $^1$H NMR (400 MHz, DMSO-d$_6$): δ11.91 (1H, s); 8.07 (1H, d); 7.98–7.71 (4H, m); 7.47 (1H, d); 7.21 (1H, t); 7.16–7.08 (2H, m); 6.93 (1H, d); 6.58 (1H, s); 4.37 (2H, m); 3.89 (2H, t); 2.81 (2H, hex); 2.09 (2H, m); 1.41 (2H, hex); 0.42 (3H, t).

APCI-MS m/z: 433.1 [MH+].

EXAMPLE 130

4-[1-(3-Aminopropyl)-5-fluoro-indol-3-yl]-5-[1-(2-fluoro-ethyl)-indol-3-yl]-2,4-dihydro-[1,2,4]triazol-3-one hydrochloride $^1$H NMR (400 MHz, DMSO-d$_6$): δ11.94 (1H, s); 8.10 (1H, d); 8.03 (2H, s); 7.84 (1H, s); 7.74 (1H, dd); 7.51 (1H, d); 7.23 (1H, t); 7.16 (1H, t); 7.11 (1H, dt); 6.98 (1H, dd); 6.68 (1H, s); 4.50 (1H, t); 4.40–4.37 (3H, m); 4.33 (1H, t); 4.26 (1H, t); 2.78 (2H, m); 2.10 (2H, p).

LSI-MS m/z: 437.2 [MH+].

EXAMPLE 131

4-[1-(3-Aminopropyl)-5-fluoro-indol-3-yl]-5-(1-ethylindol-3-yl)-2,4-dihydro-[1,2,4]triazol-3-one hydrochloride $^1$H NMR (400 MHz, DMSO-d$_6$): δ11.91 (1H, s); 8.07 (1H, d); 7.86 (2H, bs); 7.84 (1H, s); 7.73 (1H, dd); 7.48 (1H, d); 7.22 (1H, t); 7.16–7.10 (2H, m); 6.96 (1H, dd); 6.64 (1H, s); 4.38 (2H, t); 3.97 (2H, q); 2.80 (2H, m); 2.08 (2H, m); 1.02 (3H, t).

LSI-MS m/z: 419.2 [MH+].

EXAMPLE 132

4-[1-(3-Aminopropyl)-5-fluoro-indol-3-yl]-5-[1-(2-hydroxyethyl)-indol-3-yl]-2,4-dihydro-[1,2,4]triazol-3-one hydrochloride APCI-MS m/z: 435.3 [MH+].

EXAMPLE 133

4-[1-(3-Aminopropyl)-5-fluoro-indol-3-yl]-5-(1-benzyl-indol-3-yl)-2,4-dihydro-[1,2,4]triazol-3-one acetate $^1$H NMR (300 MHz, DMSO-d$_6$): δ11.94 (1H, s); 8.09 (1H, d); 7.96 (2H, bs); 7.86 (1H, s); 7.73 (1H, dd); 7.47 (1H, d); 7.21–7.10 (6H, m); 6.90 (1H, dd); 6.81–6.78 (2H, m); 6.71 (1H, s); 5.16 (2H, s); 4.37 (2H, t); 2.79 (2H, hex); 2.08 (2H, p).

APCI-MS m/z: 481.1 [MH+]

The products of Example 134 through Example 182 depicted in TABLE 1, were prepared analogously to Example 66, starting from the product of Example 45 c) and the appropriate hydrazide.

TABLE 1

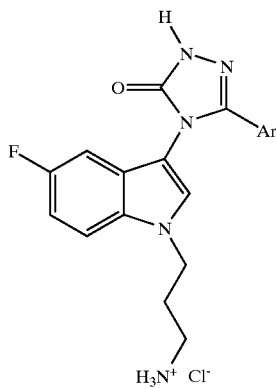

| Example no | Ar= |
|---|---|
| 134 | 2-Methyl-phenyl |
| 135 | 3-Methyl-phenyl |
| 136 | 4-Methyl-phenyl |
| 137 | 2-Nitro-phenyl |
| 138 | 3-Chloro-phenyl |
| 139 | 4-Chloro-phenyl |
| 140 | 2-Fluoro-phenyl |
| 141 | 3-Fluoro-phenyl |
| 142 | 4-Fluoro-phenyl |
| 143 | 2,4-Difluoro-phenyl |
| 144 | 3,4-Difluoro-phenyl |
| 145 | 3,4-Dichloro-phenyl |
| 146 | 3-Methoxy-phenyl |
| 147 | 4-Methoxy-phenyl |
| 148 | 3,4-Dimethoxy-phenyl |
| 149 | 3,4,5-Trimethoxy-phenyl |
| 150 | 3-Trifluoromethyl-phenyl |
| 151 | 4-Trifluoromethyl-phenyl |
| 152 | 4-Ethyl-phenyl |
| 153 | 4-tert-Butyl-phenyl |
| 154 | 3-Amino-phenyl |
| 155 | 9H-Xanthen-9-yl |
| 156 | 6H-Quinolizin-3-yl |
| 157 | 1-(3-Dimethylamino-propyl)-1H-indol-3-yl |
| 158 | 3-Dimethylaminomethyl-phenyl |
| 159 | 4-Dimethylamino-phenyl |
| 160 | 4-Ethoxy-phenyl |
| 161 | 4-Pyridinyl |
| 162 | 3-Pyridinyl |
| 163 | 2-Pyridinyl |
| 164 | 2-Furyl |
| 165 | 2-Thiopenyl |
| 166 | 1-Methyl-1H-pyrrol-2-yl |
| 167 | 5-Methyl-2H-pyrazol-3-yl |
| 168 | 6-Chloro-pyridin-3-yl |
| 169 | 2-Benzothiophenyl |
| 170 | 1-Methyl-1H-indazol-3-yl |
| 171 | 2-Methyl-2H-indazol-3-yl |
| 172 | 3-Quinolinyl |
| 173 | 4-Quinolinyl |
| 174 | 1-Isoquinolinyl |
| 175 | 3-Isoquinolinyl |
| 176 | 1H-Indol-5-yl |
| 177 | 1-Benzyl-1H-pyridin-2-on-3-yl |
| 178 | 4-Morpholin-4-ylmethyl-phenyl |
| 179 | 3-Monpholin-4-ylmethyl-phenyl |
| 180 | 2-Phenoxy-phenyl |

TABLE 1-continued

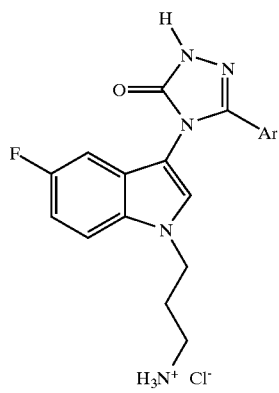

| Example no | Ar= |
|---|---|
| 181 | 1-[1-(2,2,2-Trifluoroethyl)piperidin-4-yl]-1H-indol-3-yl |
| 182 | 4-Dimethylaminomethyl-phenyl |

TABLE 2

The products of Example 183 through Example 239 depicted in TABLE 2, were prepared analogously to Example 66, starting from 3-azidocarbonyl-1-(3-dimethylamino-propyl)-5-fluoro-1H-indole and the appropriate hydrazide

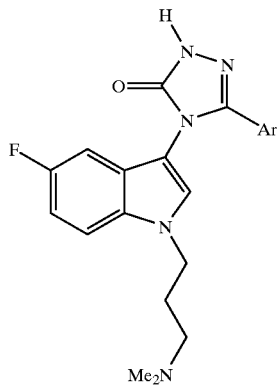

| Example no | Ar= |
|---|---|
| 183 | Phenyl |
| 184 | 2-Methyl-phenyl |
| 185 | 3-Methyl-phenyl |
| 186 | 4-Methyl-phenyl |
| 187 | 3-Bromo-phenyl |
| 188 | 4-Bromo-phenyl |
| 189 | 3-Chloro-phenyl |
| 190 | 4-Chloro-phenyl |
| 191 | 4-Fluoro-phenyl |
| 192 | 2,4-Difluoro-phenyl |
| 193 | 3,4-Difluoro-phenyl |
| 194 | 3,4-Dichloro-phenyl |
| 195 | 2-Phenoxy-phenyl |
| 196 | 3-Methoxy-phenyl |
| 197 | 4-Methoxy-phenyl |
| 198 | 3,4-Dimethoxy-phenyl |
| 199 | 3,4,5-Trimethoxy-phenyl |
| 200 | 3-Trifluoromethyl-phenyl |
| 201 | 4-Trifluoromethyl-phenyl |
| 202 | 4-Ethyl-phenyl |
| 203 | 4-tert-Butyl-phenyl |
| 204 | 3-Amino-phenyl |
| 205 | 1-Methyl-1H-indoly-3-yl |
| 206 | 9H-Xanthen-9-yl |

TABLE 2-continued

The products of Example 183 through Example 239 depicted in TABLE 2, were prepared analogously to Example 66, starting from 3-azidocarbonyl-1-(3-dimethylamino-propyl)-5-fluoro-1H-indole and the appropriate hydrazide

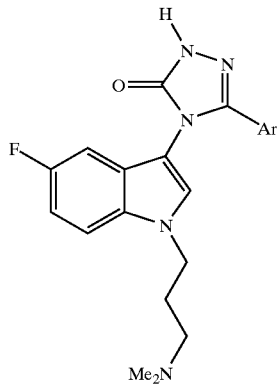

| Example no | Ar= |
|---|---|
| 207 | 6H-Quinolizin-3-yl |
| 208 | 1-Benzyl-1H-pyridin-2-on-3-yl |
| 209 | 4-Morpholin-4-ylmethyl-phenyl |
| 210 | 1-(3-Dimethylamino-propyl)-1H-indol-3-yl |
| 211 | 9H-pyridino-[3,4,b]indol-3-yl |
| 212 | 4-Dimethylamino-phenyl |
| 213 | Biphenyl-4-yl |
| 214 | 4-Phenoxy-phenyl |
| 215 | 4-Ethoxy-phenyl |
| 216 | 4-Pyridinyl |
| 217 | 3-Pyridinyl |
| 218 | 2-Pyridinyl |
| 219 | 2-Furyl |
| 220 | 2-Thiopenyl |
| 221 | 1-Methyl-1H-pyrrol-2-yl |
| 222 | 5-Methyl-2H-pyrazol-3-yl |
| 223 | 6-Chloro-pyridin-3-yl |
| 224 | 5-Bromo-pyridin-3-yl |
| 225 | 1-Naphthyl |
| 226 | 2-Naphthyl |
| 227 | 2-Benzothiophenyl |
| 228 | 3-Benzothiophenyl |
| 229 | 1-Methyl-1H-indazol-3-yl |
| 230 | 2-Methyl-2H-indazol-3-yl |
| 231 | 2-Quinolinyl |
| 232 | 3-Quinolinyl |
| 233 | 4-Quinolinyl |
| 234 | 1-Isoquinolinyl |
| 235 | 3-Isoquinolinyl |
| 236 | 1H-Indol-5-yl |
| 237 | 1H-Indol-6-yl |
| 238 | 1-[1-(2,2,2-Trifluoroethyl)piperidin-4-yl]-1H-indol-3-yl |
| 239 | 4-Dimethylaminomethyl-phenyl |

EXAMPLE 240

5-[1-(3-Aminopropyl)-5-fluoro-indol-3-yl]-4-(1-naphthyl)-2,4-dihydro-1,2,4-triazol-3-thione hydrochloride This compound was synthesised using the same procedure as in the Examples above except starting from 1-naphthylisothiocyanate.

ESI-MS m/z: 418.1 [MH+].

ABBREVIATIONS

DMF=N,N-Dimethyl formamide
MS=mass spectroscopy
NMR=nuclear magnetic resonance
THF=tetrahydrofuran
triflate=trifluoromethane sulfonate
TBS=tert-butyldimethylsilyl
TFA=trifluoroacetic acid
dba=dibenzylideneacetone

What is claimed is:

1. A compound of formula (I):

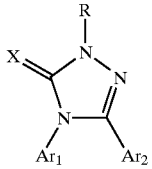

wherein: one of $Ar_1$ and $Ar_2$ is optionally substituted bicyclic heteroaryl or optionally substituted tricyclic heteroaryl and the other is optionally substituted heteroaryl or optionally substituted aryl;

X is O or, when one of $Ar_1$ and $Ar_2$ is optionally substituted bicyclic heteroaryl or optionally substituted tricyclic heteroaryl and the other is optionally substituted heteroaryl then X may also be S; and R is H, OH, $NH_2$ or $C_{1-6}$ alkyl (itself optionally substituted by amino or hydroxyl); or a salt or solvate thereof, or a solvate of a salt thereof;

provided that when X is O, R is hydrogen and one of $Ar_1$ and $Ar_2$ is phenyl or phenyl optionally mono-substituted by halogen or $C_{1-4}$ alkyl then the other is not unsubstituted benzthiazol-2-yl, a phthalimide or 1,8-naphthalimide.

2. A compound according to claim 1, wherein heteroaryl is a bicyclic system.

3. A compound according to claim 1, wherein heteroaryl contains a single heteroatom.

4. A compound according to claim 3 wherein the heteroatom is N, O or S.

5. A compound according to claim 1 wherein heteroaryl is pyridinyl, pyridin-2-onyl, thienyl, furyl, pyrrolyl, pyrazolyl, quinolinyl, isoquinolinyl, xanthen-9-yl, quinolizin-3-yl, benzothienyl, benzofuryl, indazolyl, 9H-pyrido[3,4-b]indolyl, 1H-pyrrolo[2,3-b]pyridinyl, 6,7,8,9-tetrahydro-pyrido[1,2-a]indolyl, 2,3-dihydro-1H-pyrrolo[1,2-a]indolyl or indolyl.

6. A compound as claimed in claim 1 wherein aryl is phenyl or naphthyl.

7. A compound according to claim 1, wherein bicyclic heteroaryl and heteroaryl are, independently, substituted indolyl.

8. A compound as claimed in claim 1 wherein the optional substituents on the heteroaryl and aryl groups are selected from the group comprising: halo, cyano, nitro, hydroxy, $CO_2(C_{1-4}$ alkyl), $C_{1-8}$ alkyl (optionally substituted by halo, hydroxy, cyano, $C_{1-4}$ alkoxy (optionally substituted by $NH_2$, $CO_2(C_{1-4}$ alkyl)), $NR^aR^b$, $SC(=NH)NH_2$, $C(=NH)NR^cR^d$, $N=C(R^e)NR^fR^g$, $N(R^h)C(=O)R^i$, $NHC(=NH)NH2$, heterocyclyl (optionally substituted by $C_{1-4}$ alkyl or phenyl($C_{1-4}$)alkyl), phenyl (optionally substituted by $C_{1-4}$ alkyl (itself optionally substituted by amino), $C(=NH)OR^j$, $C(=NH)NR^kR^l$), pyridinyl (optionally substituted by $C_{1-4}$ alkyl (itself optionally substituted by amino))), $C_{5-6}$ cycloalkyl (optionally substituted by hydroxy, $NR^mR^n$ or alkyl (itself optionally substituted by $NR^oR^p$)), $C_{5-6}$ cycloalkenyl (optionally substituted by $NR^qR^r$ or alkyl (itself optionally substituted by $NR^sR^t$)), heterocyclyl (optionally substituted by $C_{1-4}$ alkyl or $C_{1-4}$ haloalkyl), phenyl (optionally substituted by halo), $C_{1-6}$ alkoxy (optionally substituted by phenyl), phenoxy and amino (optionally substituted by $C_{1-4}$ alkyl); wherein $R^a$, $R^b$, $R^m$, $R^n$, $R^o$, $R^p$, $R^q$, $R^r$, $R^s$ and $R^t$ are, independently, hydrogen or $C_{1-4}$ alkyl (itself optionally substituted by hydroxy, phenyl, $CO_2H$ or $CO_2(C_{1-4}$ alkyl)); and, $R^c$, $R^d$, $R^e$, $R^f$, $R^g$, $R^h$, $R^i$, $R^j$, $R^k$ and $R^l$ are, independently, hydrogen, $C_{1-4}$ alkyl or phenyl($C_{1-4}$)alkyl; or $R^k$ and $R^l$ join to form a heterocyclic ring.

9. A compound as claimed in claim 1 wherein X is oxygen.

10. A compound as claimed in claim 1 which is a hydrochloride, hydrobromide or acetate salt.

11. A compound of formula (II) or (III):

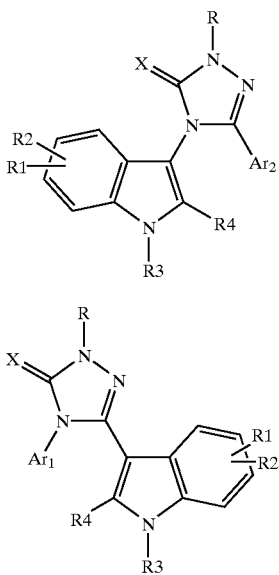

wherein: $Ar_1$ and $Ar_2$ are optionally substituted heteroaryl or optionally substituted aryl; R is hydrogen or $C_{1-3}$ alkyl; X is O or, when $Ar_1$ or $Ar_2$ is optionally substituted heteroaryl X may also be S; R1 and R2 are each independently H, $C_{1-6}$ alkyl, halogen, $C_{1-3}$ alkoxy, benzyloxy, hydroxy, cyano, fluoro substituted ($C_{1-3}$) alkyl, carboxy, carbo($C_{1-3}$)alkoxy; R3 is H, $C_{1-6}$ alkyl, benzyl, $C_{1-3}$ alkoxy substituted benzyl, hydroxy($C_{1-6}$)alkyl, hydroxy($C_{3-7}$)cycloalkyl, nitrile($C_{1-6}$) alkyl, azido($C_{1-6}$)alkyl, amino($C_{1-6}$)alkyl, amino($C_{3-7}$) cycloalkyl, aminomethyl($C_{3-7}$)cycloalkyl, amino($C_{5-7}$) cycloalkenyl, (mono- or di- $C_{1-6}$alkyl) amino($C_{1-6}$)alkyl, benzylamino($C_{1-6}$)alkyl, (mono- or di- $C_{1-6}$alkyl) amino($C_{3-7}$)cycloalkyl, (mono- or di- $C_{1-6}$alkyl) aminomethyl($C_{3-7}$) cycloalkyl, (amino($C_{1-3}$)alkylphenyl)($C_{1-3}$)alkyl, amino($C_{1-3}$)alkylphenyl, guanidino($C_{1-6}$)alkyl, amidino($C_{1-6}$)alkyl, amidinothio($C_{1-6}$)alkyl, [N,N-di-($C_{1-6}$)alkyl]amidino($C_{1-6}$) alkyl, amidino($C_{1-3}$)alkylphenyl, [N,N-mono- or di-($C_{1-6}$) alkyl]amidino($C_{1-3}$)alkylphenyl, (N-benzyl)amidino($C_{1-3}$) alkylphenyl, (4-morpholinyl)imino($C_{1-3}$)alkylphenyl, benzimic acid methyl ester($C_{1-3}$)alkyl, hydroxy($C_{1-3}$) alkylamino ($C_{1-6}$)alkyl, carboxy($C_{1-3}$)alkylamino ($C_{1-6}$) alkyl, carboxymethyl($C_{1-3}$)alkylamino ($C_{1-6}$)alkyl, amino ($C_{1-3}$)alkyloxy ($C_{2-6}$)alkyl, formamide($C_{1-6}$)alkyl, (N,N-dimethyl)imidoformamide($C_{1-6}$)alkyl, or a group of the formula —(CH$_2$)$_n$—Het in which n is an integer of 0–6, and Het is an optionally substituted 5- or 6-membered heterocyclic group; R4 is H, $C_{1-3}$ alkyl or together with R3, forms an annulated ring which may be substituted by hydroxy($C_{1-3}$) alkyl or amino ($C_{1-3}$) alkyl; or a salt or a solvate thereof, or a solvate of such a salt.

12. A compound of formula (XV):

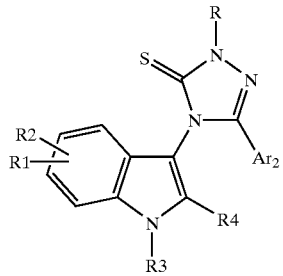

wherein R, R1, R2, R3 and R4 are as defined in claim 11 and $Ar_2$ is optionally substituted bicyclic heteroaryl or optionally substituted tricyclic heteroaryl.

13. A compound of formula (IV):

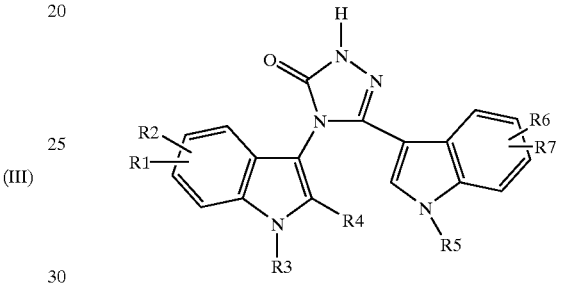

wherein R1 to R4 are as defined in claim 11; R5 is H, $C_{1-6}$ alkyl, benzyl, hydroxy($C_{1-6}$)alkyl or amino($C_{1-6}$)alkyl; and R6 and R7 are each independently H, $C_{1-3}$ alkyl, halogen, cyano, fluoro substituted $C_{1-3}$ alkyl, $C_{1-3}$ alkoxy, benzyloxy, hydroxy, cyano, carboxy or carbo($C_{1-3}$)alkoxy; or a salt or a solvate thereof, or a solvate of such a salt.

14. A pharmaceutically acceptable salt or a hydrate of a compound as claimed in claim 1 a hydrate of such a salt.

15. A pharmaceutical formulation comprising a compound as claimed in claim 1 a salt or hydrate as claimed in claim 14 as active ingredient, and a pharmaceutically acceptable adjuvant, diluent and/or carrier therefor.

16. A method of treating a mammal comprising identifying a mammal in need of treatment for an inflammatory, immunological, bronchopulmonary, cardiovascular, oncological or CNS disorder; and administering an effective amount of a compound of formula (I):

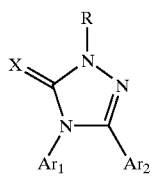

wherein
one of $Ar_1$ and $Ar_2$ is optionally substituted bicyclic heteroaryl or optionally substituted tricyclic heteroaryl and the other is optionally substituted heteroaryl or optionally substituted aryl;
X is O or S; and
R is H, OH, $NH_2$ or $C_{1-6}$ alkyl (itself optionally substituted by amino or hydroxy); or a salt, solvate or hydrate thereof, or a solvate or a hydrate of a salt thereof.

17. The method of claim 16, wherein the disorder is a PKC-mediated disease state.

* * * * *

UNITED STATES PATENT AND TRADEMARK OFFICE
CERTIFICATE OF CORRECTION

PATENT NO. : 6,492,406 B1
DATED : December 10, 2002
INVENTOR(S) : Peter Sjö, Matti Lepistö and Kostas Karabelas It is certified that error appears in the above-identified patent and that said Letters Patent is hereby corrected as shown below:

<u>Title page,</u>
Item [22], replace "PCT Filed:   Mar. 19, 2000" with -- PCT Filed:   May 19, 2000 --.
Item [56], OTHER PUBLICATIONS, "Chakravarthy et al.," replace "Substate" with -- Substrate --.
"Hiremath et al.," (seventh occurrence), replace "thier" with -- their --.
"Pereira et al. (first occurrence), replace "Five membered" with -- Five-membered --.
"Sonar et al.," replace "Synthesis Antimicrobial" with -- Synthesis and Antimicrobial --.
"*Primary Examiner*-Robert Gersil" with -- *Primary Examiner*-Robert Gerstl --.

<u>Column 76,</u>
Line 62, replace "$NR^kR^i$" with -- $NR^kR^l$ --.

<u>Column 78,</u>
Line 38, after "claim 1" insert -- or --.
Line 40, after "claim 1" insert -- or --.
Lines 40-41, after "hydrate", delete "as claimed in claim 14" and add -- thereof --.

Signed and Sealed this

Twenty-ninth Day of July, 2003

JAMES E. ROGAN
*Director of the United States Patent and Trademark Office*